(12) United States Patent
MacLaren et al.

(10) Patent No.: US 10,836,803 B2
(45) Date of Patent: Nov. 17, 2020

(54) TREATMENT OF RETINITIS PIGMENTOSA

(71) Applicant: Oxford University Innovation Limited, Oxford (GB)

(72) Inventors: Robert MacLaren, Oxford (GB); Dominik Fischer, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/505,117

(22) Filed: Jul. 8, 2019

(65) Prior Publication Data
US 2020/0002392 A1  Jan. 2, 2020

Related U.S. Application Data

(63) Continuation of application No. 15/549,627, filed as application No. PCT/GB2016/052802 on Sep. 9, 2016, now abandoned.

(30) Foreign Application Priority Data

Sep. 10, 2015 (GB) .................................. 1516066.6

(51) Int. Cl.
| | |
|---|---|
| A61K 48/00 | (2006.01) |
| C07K 14/47 | (2006.01) |
| C12N 15/86 | (2006.01) |
| C12N 9/12 | (2006.01) |

(52) U.S. Cl.
CPC ........ *C07K 14/4702* (2013.01); *A61K 48/005* (2013.01); *C12N 9/12* (2013.01); *C12N 15/86* (2013.01); *C12Y 207/11014* (2013.01); *A61K 48/00* (2013.01); *C12N 2750/14143* (2013.01); *C12N 2750/14171* (2013.01); *C12N 2800/22* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 7,943,374 B2 | 5/2011 | Hildinger | |
| 9,534,225 B2 | 1/2017 | Ye et al. | |
| 2005/0048536 A1 | 3/2005 | Rohr et al. | |
| 2012/0202769 A1 | 8/2012 | Duchaussoy et al. | |
| 2013/0210728 A1 | 8/2013 | Simo Canonge et al. | |
| 2013/0259923 A1 | 10/2013 | Bancel et al. | |
| 2015/0353938 A1 | 12/2015 | Ye et al. | |
| 2018/0273594 A1* | 9/2018 | MacLaren | C12Y 207/11014 |

FOREIGN PATENT DOCUMENTS

| | | |
|---|---|---|
| GB | 0000008801 | 5/2000 |
| JP | 2015 516143 A | 6/2015 |
| RU | 2559629 C2 | 8/2015 |
| RU | 2561585 C2 | 8/2015 |
| WO | WO 2013/063383 A2 | 5/2013 |
| WO | WO-2013/151663 A1 | 10/2013 |
| WO | WO 2013/151665 A1 | 10/2013 |
| WO | WO-2014/011210 A1 | 1/2014 |
| WO | WO 2015/160893 A1 | 10/2015 |
| WO | WO 2016/001693 A1 | 1/2016 |
| WO | WO 2016/014353 A1 | 1/2016 |
| WO | WO-2017/042584 A1 | 3/2017 |

OTHER PUBLICATIONS

Allocca et al., "Novel Adeno-Associated Virus Serotypes Efficiently Transduce Murine Photoreceptors", J. Virol. 2007; 81(20):11372-11380.
Altschul et al., "Basic Local Alignment Search Tool", J. Mol. Biol. 1990; vol. 215, pp. 403-410.
Ausubel et al., "Sequence Similarity Searching Using the BLAST Family of Programs", 1999; Chapter 18, pp. 18-1 to 18-23.
Ausubel et al., "Short Protocols in Molecular Biology", Fourth Edition, 1999; pp. 7-58 to 7-60.
Bainbridge et al., "Effect of Gene Therapy on Visual Function in Leber's Congenital Amaurosis", N. Engl. J. Med. 2008; 358:2231-9.
Beltran et al., "Gene therapy rescues photoreceptor blindness in dogs and paves the way for treating human X-linked retinitis pigmentosa," PNAS 2012; vol. 109, No. 6, pp. 2132-2137.
Benzing, T. et al., "Transition zone proteins and cilia dynamics," Nature Genetics 2011; vol. 43, No. 8, pp. 723-724.
Birnboim, H. C. et al., "A rapid alkaline extracting procedure for screening recombinant plasmid DNA", Nucleic Acids Research, Nov. 24, 1979; 7(6):1513-24.
Choi et al., "AAV Hybrid Serotypes: Improved Vectors for Gene Delivery", Curr. Gene Ther. 2005; 5:299-310.
Churchill, J. D. et al., "Mutations in the X-Linked Retinitis Pigmentosa Genes RPGR and RP2 Found in 8.5% of Families with a Provisional Diagnosis of Autosomal Dominant Retinitis Pigmentosa," Investigative Ophthalmology & Visual Science 2013; vol. 54, No. 2, pp. 1411-1416.
Coffin, J. M. et al., Retroviruses 1997; Cold Spring Harbor Laboratory Press, Eds.: J. M. Coffin, S. M. Hughes, H. E. Varmus, pp. 758-763.
Coura et al., "The state of the art of adeno-associated virus-based vectors in gene therapy", Virology Journal 2007; 4:99, (doi:10.1186/1743-422X-4-99, pp. 1-7 provided).
Cronin et al., "Functional Genomics Study of the RdCVF-/- Mouse Model", ARVO Annual Meeting 2008 Abstract: D1048; in Investigative Ophthalmology and Visual Science (2008) vol. 49: 3058 (pp. 1-2 provided).
Deng, W.-T. et al., "Stability and Safety of an AAV Vector for Treating RPGR-0RF15 X-Linked Retinitis Pigmentosa," Human Gene Therapy, vol. 26, No. 9, Jun. 15, 2015, pp. 593-602.

(Continued)

Primary Examiner — Michael D Burkhart
(74) Attorney, Agent, or Firm — Choste, Hall & Stewart LLP; Charles E. Lyon; Brian E. Reese

(57) ABSTRACT

A polynucleotide comprising a nucleotide sequence encoding the retinitis pigmentosa GTPase regulator ORF15 isoform (RPGR$^{ORF15}$), wherein the RPGR$^{ORF15}$-encoding nucleotide sequence has been codon optimised to increase fidelity of replication of the sequence.

15 Claims, 19 Drawing Sheets

Specification includes a Sequence Listing.

(56) References Cited

OTHER PUBLICATIONS

Devereux et al., "A comprehensive set of sequence analysis programs for the VAX", Nucleic Acids Res. 1984; vol. 12, No. 1, pp. 387-395.
Tatusova et al., "BLAST 2 Sequences, a new tool for comparing protein and nucleotide sequences", FEMS Microbiol. Lett. 1999; 174:247-50.
Tatusova et al., "Erratum to BLAST 2 Sequences, a new tool for comparing protein and nucleotide sequence", .FEMS Microbiol. Lett. 1999; 177:187-8.
EBI Accession No. LF573231, Oct. 29, 2016.
Genbank Gene ID 6103, Jun. 6, 2016.
Genbank Accession No. Y18065, Jan. 15, 1999.
Genbank Accession No. AF085716, Feb. 9, 1999.
Genbank Accession No. AF063497, Apr. 27, 1999.
Genbank Accession No. AY186198, Jun. 5, 2003.
Genbank Accession No. NC001863, Jan. 12, 2004.
Genbank Accession No. NC001862, Jan. 12, 2004.
Genbank Accession No. AY388617, May 25, 2004.
Genbank Accession No. AY629583, Sep. 10, 2004.
Genbank Accession No. NC001401, Mar. 30, 2006.
Genbank Accession No. NC004828, Dec. 8, 2008.
Genbank Accession No. NC001829, Jan. 28, 2010.
Genbank Accession No. NC002077, Mar. 11, 2010.
Genbank Accession No. NC005889, Jun. 23, 2010.
Genbank Accession No. NC001729, Jun. 28, 2010.
Genbank Accession No. NC006263, Jun. 28, 2010.
Hong, D.-H. et al., "Complex expression pattern of RPGR reveals a role for purine-rich exonic splicing enhancers," Investigative Ophthalmology & Visual Science (IOVS), vol. 43, No. 11, Nov. 1, 2002, pp. 3373-3382.
Hong, D.-H. et al., "A retinitis pigmentosa GTPase regulator (RPGR) deficient mouse model for X-linked retinitis pigmentosa (RP3)", Proc. Natl. Acad. Sci. USA 2000; 97:3649-3654.
Khani, S. C. et al., "AAV-Mediated Expression Targeting of ROD and cone Photoreceptors with a Human Rhodopsin Kinase Promoter," Investigative Ophthalmology & Visual Science 2007, vol. 48, No. 9, pp. 3954-3961.
Krieg et al., "An innate immune defense mechanism based on the recognition of CpG motifs in microbial DNA", The Journal of Laboratory and Clinical Medicine 1996; 128-133.
Laughlin et al., "Spliced adenovirus-associated virus RNA", Proc Natl Acad. Sci. USA 1979; 76:5567-5571.
Li, H. et al., "A mechanism of coupling RCC1 mobility to RanGTP production on the chromatin in vivo," The Journal of Cell Biology 2003; vol. 160, No. 5, pp. 635-644.
Liu, J. et al., "Rational Design and Cloning of a Stable RPGR ORF15 cDNA encoding the Full-Length Native RPGR Protein Abstract 101," Molecular Therapy 2016; vol. 24, No. 1, pp. S43-S44.

Lock et al., "Rapid, Simple, and Versatile Manufacturing of Recombinant Adeno-Associated Viral Vectors at Scale", Human Gene Therapy 2010; vol. 21; pp. 1259-1271.
Mancuso et al., "Gene Therapy for red-green colour blindness in adult primates", Nature 2009; 461:784-7 (1 additional supplemental page of methods provided).
Megaw, R. D. et al., "RPGR: Its role in photoreceptor physiology, human disease, and future therapies," Experimental Eye Research 2015, vol. 138, pp. 32-41.
Meindl, A. et al., "A gene (RPGR) with homology to the RCC1 guanine nucleotide exchange factor is mutated in X-linked retinitis pigmentosa (RP3)," Nature Genetics 1996; vol. 13, pp. 35-42.
Melamud, A. et al., "Mapping a new genetic locus for X linked retinitis pigmentosa to Xq28," J Med Genet 2006; vol. 43, No. 6, pp. e27; doi: 10.1136/jmg2005.031518, epub, 1-5 pages provided.
Nozawa, Y. et al., "Hedgehog signaling from the primary cilium to the nucleus: an emerging picture of ciliary localization, trafficking and transduction," Curr. Opin. Genetics & Development 2013; vol. 23, pp. 429-437.
Grimm, "Helper Virus-Free, Optically Controllable, and Two Plasmid-Based Production of Adeno-Associated Virus Vectors of Serotypes 1 to 6", Mol Ther 2003; 7:839-850.
Pawlyk, B. S. et al., "Photoreceptor rescue by an abbreviated human RPGR gene in a murine model of X-linked retinitis pigmentosa," Gene Therapy, vol. 23, No. 2, Sep. 8, 2015, pp. 196-204.
Sanger, F. et al., "DNA sequencing with chain-terminating inhibitors", Proc. Natl. Acad. Sci. USA 1977; 74:5463-5467.
Schmeer et al., "Pharmaceutical Grade Large-Scale Plasmid DNA Manufacturing Process", Methods in Molecular Biology, (2014), D0I10.1007/978-1, vol. 1143; pp. 219-240.
Sun, X. et al., "Loss of RPGR glutamylation underlies the pathogenic mechanism of retinal dystrophy caused by TTLL5 mutations," PNAS 2016; E2925-E2934; published ahead of print May 9, 2016. https://doi.org/10.1073/pnas.1523201113.
Tee, J. J. L. et al., "RPGR-associated retinopathy: clinical features, molecular genetics, animal models and therapeutic options," Br J Ophthalmol 2016; vol. 100, pp. 1022-1027.
Thompson, D. A. et al., Rd9 is a Naturally Occurring Mouse Model of a Common Form of Retinitis Pigmentosa Caused by Mutations in RPGR-ORF 15, PLoS One 2012; e35865, vol. 7 (May 2012), Issue 5, 1-12.
Willett et al., "Immunology of AAV-mediated gene transfer in the eye", Frontiers in Immunology 2013; 4:261; doi: 10,3389/fimmu,2013,00261 (pp. 1-8 provided).
Wu et al., "Adeno-associated Virus Serotypes: Vector Toolkit for Human Gene Therapy", Molecular Therapy 2006; 14:316-27.
Wu, Z. et al., "A long-term efficacy study of gene replacement therapy for RPGR-associated retinal degeneration", Human Molecular Genetics, 2015; 24(14):3956-3970.
International Search Report for PCT/GB2016/052802 (Treatment of Retinitis Pigmentosa, filed Sep. 9, 2016), issued by ISA/EPO, 6 pages (dated Nov. 7, 2016).
Written Opinion for PCT/GB2016/052802 (Treatment of Retinitis Pigmentosa, filed Sep. 9, 2016), issued by ISA/EPO, 8 pages (dated Nov. 7, 2016).

* cited by examiner

```
Optimized    1 ATGAGAGAGCCAGAGGAGCTGATGCCAGACAGTGGAGCAGTGTTTACATTCGGAAAATCT
Original     1 ATGAGGGAGCCGGAAGAGCTGATGCCCGATTCGGGTGCTGTGTTTACATTTGGGAAAAGT Optimized   61 AAGTTCGCTGAAAATAACCCAGGAAAGTTCTGGTTTAAAAACGACGTGCCCGTCCACCTG
Original    61 AAATTTGCTGAAAATAATCCCGGTAAATTCTGGTTTAAAAATGATGTCCCTGTACATCTT Optimized  121 TCTTGTGGCGATGAGCATAGTGCCGTGGTCACTGGGAACAATAAGCTGTACATGTTCGGG
Original   121 TCATGTGGAGATGAACATTCTGCTGTTGTTACCGGAAATAATAAACTTTACATGTTTGGC Optimized  181 TCCAACAACTGGGGACAGCTGGGGCTGGGATCCAAATCTGCTATCTCTAAGCCAACCTGC
Original   181 AGTAACAACTGGGGTCAGTTAGGATTAGGATCAAAGTCAGCCATCAGCAAGCCAACATGT Optimized  241 GTGAAGGCACTGAAACCCGAGAAGGTCAAACTGGCCGCTTGTGGCAGAAACCACACTCTG
Original   241 GTCAAAGCTCTAAAACCTGAAAAAGTGAAATTAGCTGCCTGTGGAAGGAACCACACCCTG Optimized  301 GTGAGCACCGAGGGCGGGAATGTCTATGCCACCGGAGGCAACAATGAGGGACAGCTGGGA
Original   301 GTGTCAACAGAAGGAGGCAATGTATATGCAACTGGTGGAAATAATGAAGGACAGTTGGGG Optimized  361 CTGGGGGACACTGAGGAAAGGAATACCTTTCACGTGATCTCCTTCTTTACATCTGAGCAT
Original   361 CTTGGTGACACCGAAGAAAGAAACACTTTTCATGTAATTAGCTTTTTTACATCCGAGCAT Optimized  421 AAGATCAAGCAGCTGAGCGCTGGCTCCAACACATCTGCAGCCCTGACTGAGGACGGGCGC
Original   421 AAGATTAAGCAGCTGTCTGCTGGATCTAATACTTCAGCTGCCCTAACTGAGGATGGAAGA Optimized  481 CTGTTCATGTGGGGAGATAATTCAGAGGGCCAGATTGGGCTGAAAAACGTGAGCAATGTG
Original   481 CTTTTTATGTGGGGTGACAATTCCGAAGGGCAAATTGGTTTAAAAAATGTAAGTAATGTC Optimized  541 TGCGTCCCTCAGCAGGTGACCATCGGAAAGCCAGTCAGTTGGATTTCATGTGGCTACTAT
Original   541 TGTGTCCCTCAGCAAGTGACCATTGGGAAACCTGTCTCCTGGATCTCTTGTGGATATTAC Optimized  601 CATAGCGCCTTCGTGACCACAGATGGCGAGCTGTACGTCTTTGGGGAGCCCGAAAACGGA
Original   601 CATTCAGCTTTTGTAACAACAGATGGTGAGCTATATGTGTTTGGAGAACCTGAGAATGGG Optimized  661 AAACTGGGCCTGCCTAACCAGCTGCTGGGCAATCACCGGACACCCCAGCTGGTGTCCGAG
Original   661 AAGTTAGGTCTTCCCAATCAGCTCCTGGGCAATCACAGAACACCCCAGCTGGTGTCTGAA Optimized  721 ATCCCTGAAAAAGTGATCCAGGTCGCCTGCGGGGGAGAGCATACAGTGGTCCTGACTGAG
Original   721 ATTCCGGAGAAGGTGATCCAAGTAGCCTGTGGTGGAGAGCATACTGTGGTTCTCACGGAG Optimized  781 AATGCTGTGTATACCTTCGGACTGGGCCAGTTTGGCCAGCTGGGGCTGGGAACCTTCCTG
Original   781 AATGCTGTGTATACCTTTGGGCTGGGACAATTTGGTCAGCTGGGTCTTGGCACTTTTCTT
```

FIG. 2

```
Optimized   841  TTTGAGACATCCGAACCAAAAGTGATCGAGAACATTCGCGACCAGACTATCAGCTACATT
Original    841  TTTGAAACTTCAGAACCCAAAGTCATTGAGAATATTAGGGATCAAACAATAAGTTATATT Optimized   901  TCCTGCGGAGAGAATCACACCGCACTGATCACAGACATTGGCCTGATGTATACCTTTGGC
Original    901  TCTTGTGGAGAAAATCACACAGCTTTGATAACAGATATCGGCCTTATGTATACTTTTGGA Optimized   961  GATGGACGACACGGGAAGCTGGGACTGGGACTGGAGAACTTCACTAATCATTTTATCCCC
Original    961  GATGGTCGCCACGGAAAATTAGGACTTGGACTGGAGAATTTTACCAATCACTTCATTCCT Optimized  1021  ACCCTGTGTTCTAACTTCCTGCGGTTCATCGTGAAACTGGTCGCTTGCGGCGGGTGTCAC
Original   1021  ACTTTGTGCTCTAATTTTTTGAGGTTTATAGTTAAATTGGTTGCTTGTGGTGGATGTCAC Optimized  1081  ATGGTGGTCTTCGCTGCACCTCATAGGGGCGTGGCTAAGGAGATCGAATTTGACGAGATT
Original   1081  ATGGTAGTTTTTGCTGCTCCTCATCGTGGTGTGGCAAAAGAAATTGAATTCGATGAAATA Optimized  1141  AACGATACATGCCTGAGCGTGGCAACTTTCCTGCCATACAGCTCCCTGACTTCTGGCAAT
Original   1141  AATGATACTTGCTTATCTGTGGCGACTTTTCTGCCGTATAGCAGTTTAACCTCAGGAAAT Optimized  1201  GTGCTGCAGAGAACCCTGAGTGCAAGGATGCGGAGAAGGGAGAGGGAACGCTCTCCTGAC
Original   1201  GTACTGCAGAGGACTCTATCAGCACGTATGCGGCGAAGAGAGAGGGAGAGGTCTCCAGAT Optimized  1261  AGTTTCTCAATGCGACGAACCCTGCCACCTATCGAGGGAACACTGGGACTGAGTGCCTGC
Original   1261  TCTTTTTCAATGAGGAGAACACTACCTCCAATAGAAGGGACTCTTGGCCTTTCTGCTTGT Optimized  1321  TTCCTGCCTAACTCAGTGTTTCCACGATGTAGCGAGCGGAATCTGCAGGAGTCTGTCCTG
Original   1321  TTTCTCCCCAATTCAGTCTTTCCACGATGTTCTGAGAGAAACCTCCAAGACAGTGTCTTA Optimized  1381  AGTGAGCAGGATCTGATGCAGCCAGAGGAACCCGACTACCTGCTGGATGAGATGACCAAG
Original   1381  TCTGAACAGGACCTCATGCAGCCAGAGGAACCAGATTATTTGCTAGATGAAATGACCAAA Optimized  1441  GAGGCCGAAATCGACAACTCTAGTACAGTGGAGTCCCTGGGCGAGACTACCGATATCCTG
Original   1441  GAAGCAGAGATAGATAATTCTTCAACTGTAGAAAGCCTTGGAGAAACTACTGATATCTTA Optimized  1501  AATATGACACACATTATGTCACTGAACAGCAATGAGAAGAGTCTGAAACTGTCACCAGTG
Original   1501  AACATGACACACATCATGAGCCTGAATTCCAATGAAAAGTCATTAAAATTATCACCAGTT Optimized  1561  CAGAAGCAGAAGAAACAGCAGACTATTGGCGAGCTGACTCAGGACACCGCCCTGACAGAG
Original   1561  CAGAAACAAAAGAAACAACAAACAATTGGGGAACTGACGCAGGATACAGCTCTTACTGAA Optimized  1621  AACGACGATAGCGATGAGTATGAGGAAATGTCCGAGATGAAGGAAGGCAAAGCTTGTAAG
Original   1621  AACGATGATAGTGATGAATATGAAGAAATGTCAGAAATGAAAGAAGGGAAAGCATGTAAA
```

FIG. 2 (Continued)

```
Optimized  1681  CAGCATGTCAGTCAGGGGATCTTCATGACACAGCCAGCCACAACTATTGAGGCTTTTTCA
Original   1681  CAACATGTGTCACAAGGGATTTTCATGACGCAGCCAGCTACGACTATCGAAGCATTTTCA Optimized  1741  GACGAGGAAGTGGAGATCCCCGAGGAAAAGAGGGCGCAGAAGATTCCAAGGGGAATGGA
Original   1741  GATGAGGAAGTAGAGATCCCAGACGAGAAGGAAGGAGCAGAGGATTCAAAAGGAAATGGA Optimized  1801  ATTGAGGAACAGGAGGTGGAAGCCAACGAGGAAAATGTGAAAGTCCACGGAGGCAGGAAG
Original   1801  ATAGAGGAGCAAGAGGTAGAAGCAAATGAGGAAAATGTGAAGGTGCATGGAGGAAGAAAG Optimized  1861  GAGAAAACAGAAATCCTGTCTGACGATCTGACTGACAAGGCCGAGGTGTCCGAAGGCAAG
Original   1861  GAGAAAACAGAGATCCTATCAGATGACCTTACAGACAAAGCAGAGGTGAGTGAAGGCAAG Optimized  1921  GCAAAATCTGTCGGAGAGGCAGAAGACGGACCAGAGGGACGAGGGGATGGAACCTGCGAG
Original   1921  GCAAAATCAGTGGGAGAAGCAGAGGATGGGCCTGAAGGTAGAGGGGATGGAACCTGTGAG Optimized  1981  GAAGGCTCAAGCGGGGCTGAGCATTGGCAGGACGAGGAACGAGAGAAGGGCGAAAAGGAT
Original   1981  GAAGGTAGTTCAGGAGCAGAACACTGGCAAGATGAGGAGAGGGAGAAGGGGGAGAAAGAC Optimized  2041  AAAGGCCGCGGGGAGATGGAACGACCTGGAGAGGGCGAAAAAGAGCTGGCAGAGAAGGAG
Original   2041  AAGGGTAGAGGAGAAATGGAGAGGCCAGGAGAGGCGAGAGAAGGAACTAGCAGAGAAGGAA Optimized  2101  GAATGGAAGAAAAGGGACGGCGAGGAACAGGAGCAGAAAGAAAGGGAGCAGGGCCACCAG
Original   2101  GAATGGAAGAAGAGGGATGGGGAAGAGCAGGAGCAAAAGGAGAGGGAGCAGGGCCATCAG Optimized  2161  AAGGAGCGCAACCAGGAGATGGAAGAGGGCGGCGAGGAAGAGCATGGCGAGGGAGAAGAG
Original   2161  AAGGAAAGAAACCAAGAGATGGAGGAGGGAGGGGAGGAGGAGCATGGAGAAGGAGAAGAA Optimized  2221  GAAGAGGGCGATAGAGAAGAGGAAGAGGAAAAAGAAGGCGAAGGGAAGGAGGAAGGAGAG
Original   2221  GAGGAGGGAGACAGAGAAGAGGAAGAAGAGAAGGAGGGAGAAGGGAAAGAGGAAGGAGAA Optimized  2281  GGCGAGGAAGTGGAAGGCGAGAGGGAAAAGGAGGAAGGAGAACGGAAGAAAGAGGAAAGA
Original   2281  GGGGAAGAAGTGGAGGGAGAACGTGAAAAGGAGGAAGGAGAGAGGAAAAAGGAGGAAAGA Optimized  2341  GCCGGCAAAGAGGAAAAGGGCGAGGAAGAGGGCGATCAGGGCGAAGGCGAGGAGGAAGAG
Original   2341  GCGGGGAAGGAGGAGAAAGGAGAGGAAGAAGGAGACCAAGGAGAGGGGGAAGAGGAGGAA Optimized  2401  ACCGAGGGCCGCGGGGAAGAGAAAGAGGAGGGAGGAGAGGTGGAGGGCGGAGAGGTCGAA
Original   2401  ACAGAGGGGAGAGGGGAGGAAAAGAGGAGGGAGGGGAAGTAGAGGGAGGGGAAGTAGAG Optimized  2461  GAGGGAAAGGGCGAGCGCGAAGAGGAAGAGGAAGAGGGCGAGGGCGAGGAAGAAGAGGGC
Original   2461  GAGGGGAAAGGAGAGAGGGAAGAGGAAGAGGAGGAGGGTGAGGGGGAAGAGGAGGAAGGG Optimized  2521  GAGGGGGAAGAAGAGGAGGGAGAGGGCGAAGAGGAAGAGGGGGAGGGAAAGGGCGAAGAG
Original   2521  GAGGGGGAAGAGGAGGAAGGGGAGGGGGAAGAGGAGGAAGGAGAAGGGAAAGGGGAGGAA
```

FIG. 2 (Continued)

```
Optimized  2581  GAAGGAGAGGAAGGGGAGGGAGAGGAAGAGGGGGAGGAGGGCGAGGGGGAAGGCGAGGAG
Original   2581  GAAGGGGAAGAAGGAGAAGGGGAGGAAGAAGGGGAGGAAGGAGAAGGGGAGGGGGAAGAG Optimized  2641  GAAGAAGGAGAGGGGGAAGGCGAAGAGGAAGGCGAGGGGGAAGGAGAGGAGGAAGAAGGG
Original   2641  GAGGAAGGAGAAGGGGAGGGAGAAGAGGAAGGAGAAGGGGAGGGAGAAGAGGAGGAAGGA Optimized  2701  GAAGGCGAAGGCGAAGAGGAGGGAGAAGGAGAGGGGGAGGAAGAGGAAGGAGAAGGGAAG
Original   2701  GAAGGGGAGGGAGAAGAGGAAGGAGAAGGGGAGGGAGAAGAGGAGGAAGGAGAAGGGAAA Optimized  2761  GGCGAGGAGGAAGGCGAAGAGGGAGAGGGGGAAGGCGAGGAAGAGGAAGGCGAGGGCGAA
Original   2761  GGGGAGGAGGAAGGAGAGGAAGGAGAAGGGGAGGGGGAAGAGGAGGAAGGAGAAGGGGAA Optimized  2821  GGAGAGGACGGCGAGGGCGAGGGAGAAGAGGAGGAAGGGGAATGGGAAGGCGAAGAAGAG
Original   2821  GGGGAGGATGGAGAAGGGGAGGGGGAAGAGGAGGAAGGAGAATGGGAGGGGGAAGAGGAG Optimized  2881  GAAGGCGAAGGCGAAGGCGAAGAAGAGGGCGAAGGGGAGGGCGAGGAGGGCGAAGGCGAA
Original   2881  GAAGGAGAAGGGGAGGGGGAAGAGGAAGGAGAAGGGGAAGGGGAGGAAGGAGAAGGGGAG Optimized  2941  GGGGAGGAAGAGGAAGGCGAAGGAGAAGGCGAGGAAGAAGAGGGAGAGGAGGAAGGCGAG
Original   2941  GGGGAAGAGGAGGAAGGAGAAGGGGAGGGGGAAGAGGAGGAAGGGGAAGAAGAAGGGGAG Optimized  3001  GAGGAAGGAGAGGGGGAGGAGGAGGGAGAAGGCGAGGGCGAAGAAGAAGAAGAGGGAGAA
Original   3001  GAAGAAGGAGAGGGAGAGGAAGAAGGGGAGGGAGAAGGGGAGGAAGAAGAGGAAGGGGAA Optimized  3061  GTGGAGGGCGAAGTCGAGGGGGAGGAGGGAGAAGGGGAAGGGGAGGAAGAAGAGGGCGAA
Original   3061  GTGGAAGGGGAGGTGGAAGGGGAGGAAGGAGAGGGGGAAGGAGAGGAAGAGGAAGGAGAG Optimized  3121  GAAGAAGGCGAGGAAAGAGAAAAAGAGGGAGAAGGCGAGGAAAACCGGAGAAATAGGGAA
Original   3121  GAGGAAGGAGAAGAAAGGGAAAAGCAGGGGCAAGGAGAAGAAAACAGGAGGAACAGAGAA Optimized  3181  GAGGAGGAAGAGGAAGAGGGAAAGTACCAGGAGACAGGCGAAGAGGAAAACGAGCGGCAG
Original   3181  GAGGAGGAGGAAGAAGAGGGGAAGTATCAGGAGACAGGCGAAGAAGAGAATGAAAGGCAG Optimized  3241  GATGGCGAGGAATATAAGAAAGTGAGCAAGATCAAAGGATCCGTCAAGTACGGCAAGCAC
Original   3241  GATGGAGAGGAGTACAAAAAAGTGAGCAAAATAAAAGGATCTGTGAAATATGGCAAACAT Optimized  3301  AAAACCTATCAGAAGAAAAGCGTGACCAACACACAGGGGAATGGAAAAGAGCAGAGGAGT
Original   3301  AAAACATATCAAAAAAAGTCAGTTACTAACACACAGGGCAAATGGGAAACAGCACAGGTCC Optimized  3361  AAGATGCCTGTGCAGTCAAAACGGCTGCTGAAGAATGGCCCATCTGGAAGTAAAAAATTC
Original   3361  AAAATGCCAGTCCAGTCAAAACGACTTTTAAAAAACGGGCCATCAGGTTCCAAAAAGTTC Optimized  3421  TGGAACAATGTGCTGCCCCACTATCTGGAACTGAAATAA
Original   3421  TGGAATAATGTATTACCACATTACTTGGAATTGAAGTAA
```

FIG. 2 (Continued)

```
  1                                                                      70
MREPEELMPD SGAVFTEGKS KFAENNPGKF WFKNDVPVHL SCGDEHSAVV TGNNKLYMFG SNNWGQLGLG

180
TGGNNEGQLG LGDTEERNTF HVISFFTSEH KIKQLSAGSN TSAALTEDGR LFMWGDNSEG QIGLKNVSNV
                                            confirmed 290
KLGLPNQLLG NHRTPQLVSE IPEKVIQVAC GGEHTVVLTE NAVYTFGLGQ FGQLGLGTFL FETSEPKVIE
                                 confirmed 400
LENFTNHFIP TLCSNFLRFI VKLVACGGCH MVVFAAPHRG VAKEIEFDEI NDTCLSVATF LPYSSLTSGN
                confirmed 510
FLPNSVEPRC SERNLQESVL SEQDLMQPEE PDYLLIDEMTK EAEIDNSSTV ESLGETTDIL NMTHIMSLNS 620
SEMKEGKACK QHVSQGIFMT QPATTIEAFS DEEVEIPEEK EGAEDSKGNG IEEQEVEANE ENVKVHGGRK
confirmed                                                     confirmed 730
EGSSGAEHWQ DEEREKGEKD KGRGEMERPG EGEKELAEKE EWKKRDGEEQ EQKEREQGHQ KERNQEMEEG
                                                               confirmed

840
EEGERKKEER AGKEEKGEEE GDQGEGEEEE TEGRGEEKEE GGEVEGGEVE EGKGEREEEE EEGEGEEEEG

950
EEGEGEEEE  EGEGEEEEG  EGEEEEGEGK EGEEEEGEG  GEEEEGEGE  GEEGEGEEEG GEDGEGEGEE 1,060
EEEEGEEEGE EEGEGEEEGE GEGEEEEGE VEGEVEGEEG EGEGEEEEGE EGEGERKEKEG EGEENRNRE 1,150 1,152
KTYQKKSVTN TQGNGKEQRS KMPVQSKRLL KNGPSGSGKKF WNNVLPHYLE LK
                     confirmed

FIG. 5
```

```
         80         90        100        110
SKSAISKPTC VKALKPEKVK LAACGRNHTL VSTEGGNVYA
        190        200        210        220
CVPQQVTIGK PVSWISCGYY HSAFVTTDGE LYVFGEPENG
        300        310        320        330
NIRDQTISYI SCGENHTALI TDIGLMYTFG DGRHGKLGLG
                                     confirmed
        410        420        430        440
VLQRTLSARM RRRERERSPD SFSMRRTLPP IEGTLGLSAC
                     confirmed
        520        530        540        550
NEKSLKLSPV QKQKKQQTIG ELTQDTALTE NDDSDEYEEM
        630        640        650        660
EKTEILSDDL TDKAEVSEGK AKSVGEAEDG PEGRGDGTCE
        740        750        760        770
GEEEHGEGEE EEGDREEEEE KEGEGKEEGE GEEVEGEGEK
        850        860        870        880
EGEEEEGEGE EEEGEGKGEE EGEEGEGEEE GEEEGEGEE
        960        970        980        990
EEGEWEGEEE EGEGEGEEEG EGEGEGEGEE GEEEEGEGEG
      1,070      1,080      1,090      1,100
EEEEEEGKYQ ETGEEENERQ DGEEYKKVSK IKGSVKYGKH
                     confirmed FIG. 5 (Continued)
```

DNA Concentration

Method: UV-Absorption at 260 nm

|   | Dilution | A260 | DNA Concentration |
|---|---|---|---|
| 1 | 1:50 | 0.402 | 1.005 |
| 2 | 1:50 | 0.402 | 1.004 |

$$\rho_{pDNA} = \frac{A_{260} \cdot 0.05 \cdot V_{cuv}}{V_{sample}} \; [mg \; mL^{-1}]$$

$\rho_{pDNA}$  concentration of your plasmid DNA solution [mg mL$^{-1}$]
$A_{260}$  Absorbance at a wavelength of 260 nm
$V_{cuv}$  Filling volume of the UV-cuvette (1 mL)
$V_{sample}$  Sample volume (e.g. 0.02 mL for a 1:50 dilution)
0.05  Factor (1 $A_{260}$ is equivalent to 0.05 mg mL$^{-1}$ doublestranded plasmid DNA)

Calculated averaged concentration: __1.0__ mg mL$^{-1}$

FIG. 10

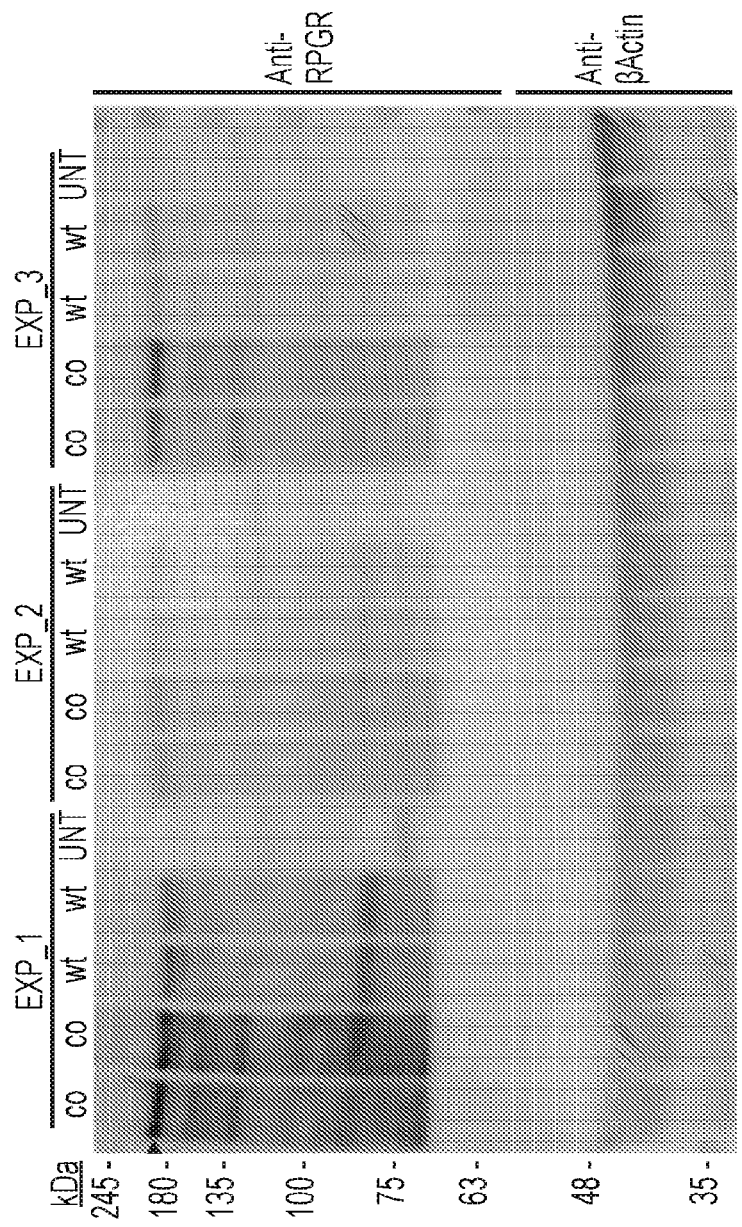
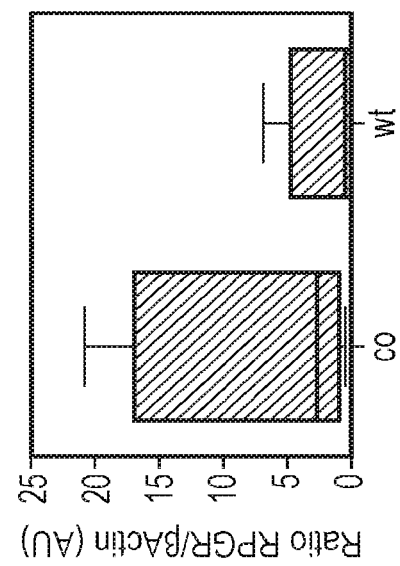
FIG. 12A
FIG. 12B

TREATMENT OF RETINITIS PIGMENTOSA

RELATED APPLICATIONS

This application is a continuation of U.S. patent application Ser. No. 15/549,627, filed Aug. 8, 2017, which is a National Stage Application, filed under 35 U.S.C. § 371, of International Application No. PCT/GB2016/052802, filed Sep. 9, 2016, which claims priority to GB 1516066.6, filed on Sep. 10, 2015, the contents of each of which are incorporated by reference herein, in their entirety and for all purposes.

REFERENCE TO SEQUENCE LISTING

This application is being filed electronically via EFS-Web and includes an electronically submitted sequence listing in .txt format. The .txt file contains a sequence listing entitled "NIGH_004C01US_SeqList_ST25.txt" created on Jul. 8, 2019 and having a size of ~40 kilobytes. The sequence listing contained in this .txt file is part of the specification and is incorporated herein by reference in its entirety.

FIELD OF THE INVENTION

The present invention relates to compounds for use in the gene therapy of eye diseases. More specifically, the invention relates to viral vectors, in particular adeno-associated viral (AAV) vectors, for use in the treatment or prevention of retinitis pigmentosa (RP), wherein the viral vectors enable delivery of the retinitis pigmentosa GTPase regulator ORF15 isoform (RPGR$^{ORF15}$) to the eye.

BACKGROUND TO THE INVENTION

Retinitis pigmentosa (RP) is a phenotypically linked group of inherited retinal dystrophies that leads to gradual reduction in vision. RP affects approximately 1 in 3000-4000 people.

Early symptoms of RP include deterioration of night and peripheral vision. As the disease progresses, detailed, central and colour vision may also be affected. The age of onset of RP symptoms is variable, but typically between 10 and 30, and the rate of deterioration varies between individuals.

RP is commonly caused by the progressive degeneration of rod photoreceptor cells. However, the retinal pigment epithelium (RPE) and cone photoreceptor cells may also degenerate during progression of the disease.

RP may be caused, for example, by mutations in one of many different genes relevant for the health and function of the eye. Of all the single gene causes of RP, the X-linked disease that results from defects in the retinitis pigmentosa GTPase regulator (RPGR) gene is the most common.

X-linked retinitis pigmentosa (XLRP) is regarded as the most severe form of retinitis pigmentosa. Subjects suffering from XLRP experience restriction of the peripheral visual field and night blindness within the first two decades of life. In addition, glare, involuntary pendular movement of the eyes, colour vision disturbances and reduced central visual acuity characterise this condition. As a result, patients typically become legally blind even before completion of their secondary education.

The RPGR gene is highly mutagenic, which increases the likelihood of disease-causing mutations being generated in vivo. However, this mutagenic nature also gives rise to problems when producing vectors encoding RPGR for use in gene therapy. Indeed, previous strategies to develop gene replacement therapies for XLRP have been hampered by such mutations: only very recently a promising research programme was delayed due to a mutation discovered in the ORF15 region of the transgene cassette. In another programme, alternative RPGR splice variants were detected by Western blot (Wu, Z. et al. (2015) Hum. Mol. Genet. 24: 3956-3970).

There is currently no approved therapy to prevent the development of RP or to improve vision following the onset of the disease. Accordingly, there remains a significant need for treatments of RP, in particular to prevent deterioration in visual function or to enable improvement in the vision of affected individuals.

SUMMARY OF THE INVENTION

The present inventors have surprisingly found that the sequence of the retinitis pigmentosa GTPase regulator ORF15 isoform (RPGR$^{ORF15}$) gene can be engineered to increase sequence stability, such as by reducing or preventing the occurrence of mutations during replication (i.e. increasing the fidelity of replication). The present inventors have also unexpectedly discovered that risks of the engineering affecting the function of the gene can be mitigated. Moreover, the engineered genes have been demonstrated by the present inventors to successfully treat animal models of retinitis pigmentosa.

Accordingly, in one aspect, the invention provides a polynucleotide comprising a nucleotide sequence encoding the retinitis pigmentosa GTPase regulator ORF15 isoform (RPGR$^{ORF15}$), wherein the RPGR$^{ORF15}$-encoding nucleotide sequence has been codon optimised to increase fidelity of replication of the sequence.

Preferably, the RPGR$^{ORF15}$-encoding nucleotide sequence of the invention has been codon optimised to reduce the generation of alternative splice variants.

Preferably, the RPGR$^{ORF15}$-encoding nucleotide sequence of the invention has been codon optimised to minimise or avoid the creation of new CpG sites in comparison to the wild type sequence. In one embodiment, the RPGR$^{ORF15}$-encoding nucleotide sequence of the invention comprises less than 220, 210, 200, 190, 170, 165, 160, 150, 140, 130, 120, 110 or 100 CpG sites.

Preferably, the RPGR$^{ORF15}$-encoding nucleotide sequence of the invention has been codon optimised by replacing some or all GGN codons with GGC codons (when the GGN codons were not originally GGC codons).

Preferably, the RPGR$^{ORF15}$-encoding nucleotide sequence of the invention has been codon optimised to minimise or avoid the introduction of new thymine nucleotides in the purine-rich (i.e. GA-rich) regions of the RPGR$^{ORF15}$-encoding nucleotide sequence, for example the ORF 15 exon region (which corresponds to nucleotides 1754-3459 of RPGR$^{ORF15}$, e.g. nucleotides 1754-3459 of SEQ ID NO: 2).

Preferably, the RPGR$^{ORF15}$-encoding nucleotide sequence of the invention has been codon optimised to reduce the number of GT sites (i.e. potential splice donor sites) in comparison to the wild type sequence. In one embodiment, the RPGR$^{ORF15}$-encoding nucleotide sequence of the invention comprises less than 120, 115, 110, 105, 100, 90, 80, 70, 60, 50, 40, 30, 20 or 10 GT sites. In a preferred embodiment, the RPGR$^{ORF15}$-encoding nucleotide sequence of the invention comprises less than 105 GT sites.

Preferably, the RPGR$^{ORF15}$-encoding nucleotide sequence of the invention has been codon optimised to avoid the creation of anomalous polyA signals (e.g. AATAAA).

In one embodiment, the RPGR$^{ORF15}$-encoding nucleotide sequence of the invention has been codon optimised to reduce the number of purine nucleotides in comparison to the wild type sequence. The wild type sequence may, for example, be the sequence of SEQ ID NO: 2.

Preferably, the number of purine nucleotides is reduced by replacing purine nucleotides with pyrimidine nucleotides.

In one embodiment, the number of purine nucleotides is reduced in purine-rich (i.e. GA-rich) regions of the RPGR$^{ORF15}$-encoding nucleotide sequence, for example the ORF 15 exon region (which corresponds to nucleotides 1754-3459 of RPGR$^{ORF15}$, e.g. nucleotides 1754-3459 of SEQ ID NO: 2).

In another embodiment, the RPGR$^{ORF15}$-encoding nucleotide sequence of the invention does not comprise purine nucleotides at positions corresponding to nucleotides 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 2121, 2167, 2169, 2190, 2193, 2208, 2229, 2259, 2283, 2298, 2323, 2343, 2346, 2361, 2373, 2382, 2388, 2403, 2409, 2410, 2412, 2448, 2457, 2472, 2476, 2478, 2505, 2520, 2547, 2574, 2622, 2634, 2661, 2673, 2706, 2712, 2763, 2775, 2796, 2811, 2817, 2832, 2838, 2871, 2886, 2892, 2898, 2910, 2922, 2931, 2937, 2958, 2970, 2997, 3033, 3039, 3069, 3075, 3117, 3129, 3156, 3166, 3235, 3246, 3273, 3285, 3306, 3321, 3369, 3399, 3405 and/or 3438 of SEQ ID NO: 2. Preferably the nucleotides at these positions correspond to those found in SEQ ID NO:3. In another embodiment, the RPGR$^{ORF15}$-encoding nucleotide sequence of the invention does not comprise purine nucleotides at at least 2, 3, 4, 5, 10, 20, 30, 40, 50, 60, 70, 80, 90 or all of these nucleotide positions. Preferably, the nucleotide sequence encodes an amino acid sequence with at least 90%, 91%, 92%, 93%, 94%, 95%, 96%, 97%, 98% or 99% identity to SEQ ID NO: 1. More preferably, the nucleotide sequence encodes the amino acid sequence of SEQ ID NO: 1.

In another embodiment, the RPGR$^{ORF15}$-encoding nucleotide sequence of the invention is derived from SEQ ID NO: 2 by replacing the purine nucleotides at positions 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 2121, 2167, 2169, 2190, 2193, 2208, 2229, 2259, 2283, 2298, 2323, 2343, 2346, 2361, 2373, 2382, 2388, 2403, 2409, 2410, 2412, 2448, 2457, 2472, 2476, 2478, 2505, 2520, 2547, 2574, 2622, 2634, 2661, 2673, 2706, 2712, 2763, 2775, 2796, 2811, 2817, 2832, 2838, 2871, 2886, 2892, 2898, 2910, 2922, 2931, 2937, 2958, 2970, 2997, 3033, 3039, 3069, 3075, 3117, 3129, 3156, 3166, 3235, 3246, 3273, 3285, 3306, 3321, 3369, 3399, 3405 and/or 3438 with pyrimidine nucleotides (e.g. thymine or cytosine). Preferably the nucleotides at these positions correspond to those found in SEQ ID NO:3. In another embodiment, the purine nucleotides have been replaced at at least 2, 3, 4, 5, 10, 20, 30, 40, 50, 60, 70, 80, 90 or all of these nucleotide positions. Preferably, the nucleotide sequence encodes an amino acid sequence with at least 90%, 91%, 92%, 93%, 94%, 95%, 96%, 97%, 98% or 99% identity to SEQ ID NO: 1. More preferably, the nucleotide sequence encodes the amino acid sequence of SEQ ID NO: 1.

According to the invention, the number of purine nucleotides may be reduced by at least 0.5%, 1%, 1.5%, 2%, 2.5%, 3%, 3.5%, 4%, 4.5% or 5% of the number of purine nucleotides in the wild type sequence (e.g. SEQ ID NO: 2).

According to the invention, the number of purine nucleotides may be reduced by 0.5-10%, 0.5-7.5%, 0.5-5%, 0.5-4.5%, 0.5-4%, 0.5-3.5%, 0.5-3%, 1-5%, 1-4.5%, 1-4%, 1-3.5% or 1-3% of the number of purine nucleotides in the wild type sequence (e.g. SEQ ID NO: 2).

In one embodiment, the RPGR$^{ORF15}$-encoding nucleotide sequence of the invention has been codon optimised to reduce the number of adenine nucleotides in comparison to the wild type sequence. The wild type sequence may, for example, be the sequence of SEQ ID NO: 2. In another embodiment, the number of adenine nucleotides has been reduced by at least 10, 20, 30, 40, 50, 60, 70, 80, 90, 100, 110, 120, 130, 140, 150, 160, 170, 180, 190 or 200. In one embodiment, adenines at positions corresponding to nucleotides 58, 114, 123, 129, 181, 213, 219, 226, 237, 285, 306, 309, 315, 324, 330, 339, 400, 444, 456, 478, 480, 594, 606, 618, 697, 744, 807, 852, 877, 888, 891, 921, 930, 960, 1042, 1050, 1116, 1140, 1183, 1194, 1197, 1221, 1249, 1257, 1273, 1276, 1281, 1290, 1293, 1357, 1372, 1413, 1446, 1452, 1464, 1474, 1482, 1519, 1542, 1584, 1608, 1653, 1674, 1692, 1734, 1761, 1776, 1788, 1803, 1824, 1854, 1881, 1893, 1902, 1909, 1929, 1960, 1987, 1992, 1998, 2020, 2047, 2049, 2062, 2067, 2076, 2167, 2169, 2190, 2208, 2229, 2259, 2298, 2323, 2361, 2373, 2382, 2403, 2410, 2412, 2448, 2457, 2472, 2476, 2622, 2661, 2673, 2712, 2775, 2811, 2832, 2886, 2910, 2931, 2958, 3033, 3117, 3129, 3156, 3166, 3235, 3246, 3273, 3306, 3321, 3369, 3405 and/or 3438 of SEQ ID NO: 2 are replaced with pyrimidine nucleotides (e.g. thymine or cytosine). Preferably the nucleotides at these positions correspond to those found in SEQ ID NO:3.

In one embodiment, the RPGR$^{ORF15}$-encoding nucleotide sequence of the invention does not comprise a purine nucleotide at at least one position, preferably at least 5, 10, 20, 30, 40, 50, 60, 70, 80, 90, 100, 110, 120, 130, 140, 150, 160, 170 or 180 positions, preferably all positions, corresponding to a position where a purine nucleotide in SEQ ID NO: 2 (wtRPGR) aligns with a pyrimidine nucleotide in SEQ ID NO: 3 (coRPGR), for example in the sequence alignment of FIG. 2 (wtRPGR, "Original"; coRPGR, "Optimized").

In another embodiment, the RPGR$^{ORF15}$-encoding nucleotide sequence of the invention does not comprise purine nucleotides at positions corresponding to nucleotides 33, 58, 59, 114, 123, 129, 181, 182, 213, 219, 226, 227, 237, 267, 285, 306, 309, 315, 324, 330, 339, 400, 401, 444, 456, 478, 480, 510, 594, 606, 618, 639, 697, 726, 744, 777, 807, 852, 877, 879, 888, 891, 921, 930, 960, 1042, 1050, 1116, 1140, 1183, 1184, 1194, 1197, 1221, 1249, 1251, 1257, 1273, 1276, 1281, 1290, 1293, 1357, 1372, 1373, 1413, 1446, 1452, 1464, 1474, 1475, 1482, 1519, 1520, 1542, 1584, 1590, 1599, 1608, 1653, 1668, 1674, 1689, 1692, 1734, 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 2121, 2167, 2169, 2190, 2193, 2208, 2229, 2259, 2283, 2298, 2323, 2343, 2346, 2361, 2373, 2382, 2388, 2403, 2409, 2410, 2412, 2448, 2457, 2472, 2476, 2478, 2505, 2520, 2547, 2574, 2622, 2634, 2661, 2673, 2706, 2712, 2763, 2775, 2796, 2811, 2817, 2832, 2838, 2871, 2886, 2892, 2898, 2910, 2922, 2931, 2937, 2958, 2970, 2997, 3033, 3039, 3069, 3075, 3117, 3129, 3156, 3166, 3235, 3246, 3273, 3285, 3306, 3321, 3369, 3399, 3405 and/or 3438 of SEQ ID NO: 2. Preferably the nucleotides at these positions correspond to those found in SEQ ID NO:3. In another embodiment, the RPGR$^{ORF15}$-encoding nucleotide sequence of the invention does not comprise purine nucleotides at at least 2, 3, 4, 5, 10, 20, 30, 40, 50, 60, 70, 80, 90, 100, 110, 120, 130, 140, 150, 160, 170, 180 or all of these nucleotide positions. Preferably, the nucleotide sequence encodes an amino acid sequence with at least 90%, 91%, 92%, 93%, 94%, 95%, 96%, 97%, 98% or 99% identity to SEQ ID NO: 1. More preferably, the nucleotide sequence encodes the amino acid sequence of SEQ ID NO: 1.

It should be noted that in this application nucleotide positions are identified by those 'corresponding' to a particular position in SEQ ID NO:2. This is not to be interpreted as meaning the sequences of the present invention must include sequences present in SEQ ID NO:2. Herein, the nucleotides of the RPGR$^{ORF15}$-encoding nucleotide sequence are numbered following a convention whereby the 5' adenine of SEQ ID NO: 2 is assigned to be nucleotide 1. Identities of individual nucleotides and positions of mutations are described herein with reference to this numbering convention. A skilled person would readily be able to determine analogous positions in homologous sequences by performing a sequence alignment to SEQ ID NO: 2. An example of such an alignment is shown in FIG. 2.

In another embodiment, the RPGR$^{ORF15}$-encoding nucleotide sequence of the invention is derived from SEQ ID NO: 2 by replacing the purine nucleotides at positions 33, 58, 59, 114, 123, 129, 181, 182, 213, 219, 226, 227, 237, 267, 285, 306, 309, 315, 324, 330, 339, 400, 401, 444, 456, 478, 480, 510, 594, 606, 618, 639, 697, 726, 744, 777, 807, 852, 877, 879, 888, 891, 921, 930, 960, 1042, 1050, 1116, 1140, 1183, 1184, 1194, 1197, 1221, 1249, 1251, 1257, 1273, 1276, 1281, 1290, 1293, 1357, 1372, 1373, 1413, 1446, 1452, 1464, 1474, 1475, 1482, 1519, 1520, 1542, 1584, 1590, 1599, 1608, 1653, 1668, 1674, 1689, 1692, 1734, 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 2121, 2167, 2169, 2190, 2193, 2208, 2229, 2259, 2283, 2298, 2323, 2343, 2346, 2361, 2373, 2382, 2388, 2403, 2409, 2410, 2412, 2448, 2457, 2472, 2476, 2478, 2505, 2520, 2547, 2574, 2622, 2634, 2661, 2673, 2706, 2712, 2763, 2775, 2796, 2811, 2817, 2832, 2838, 2871, 2886, 2892, 2898, 2910, 2922, 2931, 2937, 2958, 2970, 2997, 3033, 3039, 3069, 3075, 3117, 3129, 3156, 3166, 3235, 3246, 3273, 3285, 3306, 3321, 3369, 3399, 3405 and/or 3438 with pyrimidine nucleotides (e.g. thymine or cytosine). Preferably the nucleotides at these positions correspond to those found in SEQ ID NO:3. In another embodiment, the purine nucleotides have been replaced at at least 2, 3, 4, 5, 10, 20, 30, 40, 50, 60, 70, 80, 90, 100, 110, 120, 130, 140, 150, 160, 170, 180 or all of these nucleotide positions. Preferably the purine nucleotides have been replaced at all of these nucleotide positions. Preferably, the nucleotide sequence encodes an amino acid sequence with at least 90%, 91%, 92%, 93%, 94%, 95%, 96%, 97%, 98% or 99% identity to SEQ ID NO: 1. More preferably, the nucleotide sequence encodes the amino acid sequence of SEQ ID NO: 1.

In one embodiment, the RPGR$^{ORF15}$-encoding nucleotide sequence is such that the nucleotide corresponding to position 33 of SEQ ID NO:2 is T, the nucleotide corresponding to position 58 is T, the nucleotide corresponding to position 59 is C, the nucleotide corresponding to position 114 is C, the nucleotide corresponding to position 123 is T, the nucleotide corresponding to position 129 is C, the nucleotide corresponding to position 181 is T, the nucleotide corresponding to position 182 is C, the nucleotide corresponding to position 213 is C, the nucleotide corresponding to position 219 is T, the nucleotide corresponding to position 226 is T, the nucleotide corresponding to position 227 is C, the nucleotide corresponding to position 237 is C, the nucleotide corresponding to position 267 is C, the nucleotide corresponding to position 285 is C, the nucleotide corresponding to position 306 is C, the nucleotide corresponding to position 309 is C, the nucleotide corresponding to position 315 is C, the nucleotide corresponding to position 324 is C, the nucleotide corresponding to position 330 is C, the nucleotide corresponding to position 339 is C, the nucleotide corresponding to position 400 is T, the nucleotide corresponding to position 401 is C, the nucleotide corresponding to position 444 is C, the nucleotide corresponding to position 456 is T, the nucleotide corresponding to position 478 is C, the nucleotide corresponding to position 480 is C, the nucleotide corresponding to position 510 is C, the nucleotide corresponding to position 594 is C, the nucleotide corresponding to position 606 is C, the nucleotide corresponding to position 618 is C, the nucleotide corresponding to position 639 is C, the nucleotide corresponding to position 697 is C, the nucleotide corresponding to position 726 is T, the nucleotide corresponding to position 744 is C, the nucleotide corresponding to position 777 is T, the nucleotide corresponding to position 807 is C, the nucleotide corresponding to position 852 is C, the nucleotide corresponding to position 877 is C, the nucleotide corresponding to position 879 is C, the nucleotide corresponding to position 888 is T, the nucleotide corresponding to position 891 is C, the nucleotide corresponding to position 921 is C, the nucleotide corresponding to position 930 is C, the nucleotide corresponding to position 960 is C, the nucleotide corresponding to position 1042 is C, the nucleotide corresponding to position 1050 is C, the nucleotide corresponding to position 1116 is T, the nucleotide corresponding to position 1140 is T, the nucleotide corresponding to position 1183 is T, the nucleotide corresponding to position 1184 is C, the nucleotide corresponding to position 1194 is T, the nucleotide corresponding to position 1197 is C, the nucleotide corresponding to position 1221 is T, the nucleotide corresponding to position 1249 is C, the nucleotide corresponding to position 1251 is C, the nucleotide corresponding to position 1257 is T, the nucleotide corresponding to position 1273 is C, the nucleotide corresponding to position 1276 is C, the nucleotide corresponding to position 1281 is C, the nucleotide corresponding to position 1290 is T, the nucleotide corresponding to position 1293 is C, the nucleotide corresponding to position 1357 is C, the nucleotide corresponding to position 1372 is T, the nucleotide corresponding to position 1373 is C, the nucleotide corresponding to position 1413 is C, the nucleotide corresponding to position 1446 is C, the nucleotide corresponding to position 1452 is C, the nucleotide corresponding to position 1464 is T, the nucleotide corresponding to position 1474 is T, the nucleotide corresponding to position 1475 is C, the nucleotide corresponding to position 1482 is C, the nucleotide corresponding to position 1519 is T, the nucleotide corresponding to position 1520 is C, the nucleotide corresponding to position 1542 is T, the nucleotide corresponding to position 1584 is T, the nucleotide corresponding to position 1590 is C, the nucleotide corresponding to position 1599 is T, the nucleotide corresponding to position 1608 is C, the nucleotide corresponding to position 1653 is C, the nucleotide corresponding to position 1668 is C, the nucleotide corresponding to position 1674 is T, the nucleotide corresponding to position 1689 is C, the nucleotide corresponding to position 1692 is T, the nucleotide corresponding to position 1734 is T, the nucleotide corresponding to position 1761 is C, the nucleotide corresponding to position 1776 is C, the nucleotide corresponding to position 1788 is C, the nucleotide corresponding to position 1803 is T, the nucleotide corresponding to position 1824 is C, the nucleotide corresponding to position 1845 is C, the nucleotide corresponding to position 1854 is C, the nucleotide corresponding to position 1881 is T, the nucleotide corresponding to position 1893 is T, the nucleotide corresponding to position 1902 is C, the nucleotide corresponding to position 1909 is T, the nucleotide corresponding to position 1910 is C, the nucleotide corresponding to position 1929 is T, the nucleotide corresponding to position 1932 is C, the nucleotide corresponding to position 1960 is C, the nucleotide corresponding to position 1987 is T, the nucleotide corresponding to position 1988 is C, the nucleotide corresponding to position 1992 is C, the nucleotide corresponding to position 1998 is T, the nucleotide corresponding to position 2020 is C, the nucleotide corresponding to position 2031 is C, the nucleotide corresponding to position 2047 is C, the nucleotide corresponding to position 2049 is C, the nucleotide corresponding to position 2062 is C, the nucleotide corresponding to position 2067 is T, the nucleotide corresponding to position 2076 is C, the nucleotide corresponding to position 2121 is C, the nucleotide corresponding to position 2167 is C, the nucleotide corresponding to position 2169 is C, the nucleotide corresponding to position 2190 is C, the nucleotide corresponding to position 2193 is C, the nucleotide corresponding to position 2208 is C, the nucleotide corresponding to position 2229 is C, the nucleotide corresponding to position 2259 is C, the nucleotide corresponding to position 2283 is C, the nucleotide corresponding to position 2298 is C, the nucleotide corresponding to position 2323 is C, the nucleotide corresponding to position 2343 is C, the nucleotide corresponding to position 2346 is C, the nucleotide corresponding to position 2361 is C, the nucleotide corresponding to position 2373 is C, the nucleotide corresponding to position 2382 is C, the nucleotide corresponding to position 2388 is C, the nucleotide corresponding to position 2403 is C, the nucleotide corresponding to position 2409 is C, the nucleotide corresponding to position 2410 is C, the nucleotide corresponding to position 2412 is C, the nucleotide corresponding to position 2448 is C, the nucleotide corresponding to position 2457 is C, the nucleotide corresponding to position 2472 is C, the nucleotide corresponding to position 2476 is C, the nucleotide corresponding to position 2478 is C, the nucleotide corresponding to position 2505 is C, the nucleotide corresponding to position 2520 is C, the nucleotide corresponding to position 2547 is C, the nucleotide corresponding to position 2574 is C, the nucleotide corresponding to position 2622 is C, the nucleotide corresponding to position 2634 is C, the nucleotide corresponding to position 2661 is C, the nucleotide corresponding to position 2673 is C, the nucleotide corresponding to position 2706 is C, the nucleotide corresponding to position 2712 is C, the nucleotide corresponding to position 2763 is C, the nucleotide corresponding to position 2775 is C, the nucleotide corresponding to position 2796 is C, the nucleotide corresponding to position 2811 is C, the nucleotide corresponding to position 2817 is C, the nucleotide corresponding to position 2832 is C, the nucleotide corresponding to position 2838 is C, the nucleotide corresponding to position 2871 is C, the nucleotide corresponding to position 2886 is C, the nucleotide corresponding to position 2892 is C, the nucleotide corresponding to position 2898 is C, the nucleotide corresponding to position 2910 is C, the nucleotide corresponding to position 2922 is C, the nucleotide corresponding to position 2931 is C, the nucleotide corresponding to position 2937 is C, the nucleotide corresponding to position 2958 is C, the nucleotide corresponding to position 2970 is C, the nucleotide corresponding to position 2997 is C, the nucleotide corresponding to position 3033 is C, the nucleotide corresponding to position 3039 is C, the nucleotide corresponding to position 3069 is C, the nucleotide corresponding to position 3075 is C, the nucleotide corresponding to position 3117 is C, the nucleotide corresponding to position 3129 is C, the nucleotide corresponding to position 3156 is C, the nucleotide corresponding to position 3166 is C, the nucleotide corresponding to position 3235 is C, the nucleotide corresponding to position 3246 is C, the nucleotide corresponding to position 3273 is C, the nucleotide corresponding to position 3285 is C, the nucleotide corresponding to position 3306 is C, the nucleotide corresponding to position 3321 is C, the nucleotide corresponding to position 3369 is T, the nucleotide corresponding to position 3399 is C, the nucleotide corresponding to position 3405 is T and/or the nucleotide corresponding to position 3438 is C.

In one embodiment, the RPGR$^{ORF15}$-encoding nucleotide sequence does not comprise purine nucleotides at positions corresponding to nucleotides 1689 and/or 3438 of SEQ ID NO: 2. The nucleotide at position 1689 may be replaced with a pyrimidine, preferably a C. The adenine at position 3438 may be replaced with a pyrimidine, preferably a C.

In one embodiment, the RPGR$^{ORF15}$-encoding nucleotide sequence is derived from SEQ ID NO:2 by replacing the adenine nucleotide at position 3405 with a pyrimidine nucleotide without introducing a CpG dinucleotide.

In one embodiment, the RPGR$^{ORF15}$-encoding nucleotide sequence comprises an adenine nucleotide at the position corresponding to position 3405 of SEQ ID NO:2.

In one embodiment, the encoded RPGR$^{ORF15}$ protein is human RPGR$^{ORF15}$.

In one embodiment, the RPGR$^{ORF15}$-encoding nucleotide sequence comprises one or more nucleotides selected from: C at the position corresponding to position 30 of SEQ ID NO: 2, T at the position corresponding to position 33 of SEQ ID NO: 2, A at the position corresponding to position 966 of SEQ ID NO: 2, A at the position corresponding to position 969 of SEQ ID NO: 2, T at the position corresponding to position 1011 of SEQ ID NO:2, T at the position corresponding to position 1014 of SEQ ID NO:2, T at the position corresponding to position 1029 of SEQ ID NO:2, A at the position corresponding to position 1299 of SEQ ID NO:2, C at the position corresponding to position 1689 of SEQ ID NO:2, G at the position corresponding to position 3363 of SEQ ID NO:2, T at the position corresponding to position 3405 of SEQ ID NO:2, A at the position corresponding to position 3408 of SEQ ID NO:2, A at the position corresponding to position 3409 of SEQ ID NO:2, G at the position corresponding to position 3410 of SEQ ID NO:2, G at the position corresponding to position 3432 of SEQ ID NO:2, C at the position corresponding to position 3438 of SEQ ID NO:2 and A at the position corresponding to position 3456 of SEQ ID NO:2.

In one embodiment, the RPGR$^{ORF15}$-encoding nucleotide sequence comprises one or more nucleotides selected from: C at the position corresponding to position 30 of SEQ ID NO: 2, T at the position corresponding to position 33 of SEQ ID NO: 2, A at the position corresponding to position 48 of SEQ ID NO: 2, A at the position corresponding to position 57 of SEQ ID NO: 2, T at the position corresponding to position 60 of SEQ ID NO: 2, T at the position corresponding to position 69 of SEQ ID NO: 2, A at the position corresponding to position 72 of SEQ ID NO: 2, C at the position corresponding to position 171 of SEQ ID NO: 2, C at the position corresponding to position 189 of SEQ ID NO: 2, T at the position corresponding to position 441 of SEQ ID NO: 2, T at the position corresponding to position 537 of SEQ ID NO: 2, C at the position corresponding to position 546 of SEQ ID NO: 2, T at the position corresponding to position 786 of SEQ ID NO: 2, T at the position corresponding to position 792 of SEQ ID NO: 2, A at the position corresponding to position 966 of SEQ ID NO: 2, A at the position corresponding to position 969 of SEQ ID NO: 2, A at the position corresponding to position 990 of SEQ ID NO: 2, T at the position corresponding to position at the position corresponding to position 1029 of SEQ ID NO: 2, A at the position corresponding to position 1299 of SEQ ID NO: 2, C at the position corresponding to position 1689 of SEQ ID NO: 2, A at the position corresponding to position 3355 of SEQ ID NO: 2, G at the position corresponding to position 3357 of SEQ ID NO: 2, G at the position corresponding to position 3363 of SEQ ID NO: 2, T at the position corresponding to position 3403 of SEQ ID NO: 2, C at the position corresponding to position 3404 of SEQ ID NO: 2, T at the position corresponding to position 3405 of SEQ ID NO: 2, A at the position corresponding to position 3408 of SEQ ID NO: 2, A at the position corresponding to position 3409 of SEQ ID NO: 2, G at the position corresponding to position 3410 of SEQ ID NO: 2, G at the position corresponding to position 3432 of SEQ ID NO: 2, C at the position corresponding to position 3438 of SEQ ID NO: 2 and A at the position corresponding to position 3456 of SEQ ID NO: 2.

In one embodiment, the RPGR$^{ORF15}$-encoding nucleotide sequence of the invention comprises a sequence selected from the group consisting of:
(a) a nucleotide sequence encoding an amino acid sequence that has at least 80% identity to SEQ ID NO: 1;
(b) a nucleotide sequence that has at least 80% identity to SEQ ID NO: 3; and
(c) the nucleotide sequence of SEQ ID NO: 3,
preferably wherein the protein encoded by the nucleotide sequence substantially retains the natural function of the protein represented by SEQ ID NO: 1.

In another embodiment, the RPGR$^{ORF15}$-encoding nucleotide sequence of the invention comprises a nucleotide sequence encoding an amino acid sequence that has at least 85%, 90%, 91%, 92%, 93%, 94%, 95%, 96%, 97%, 98%, 99% or 100% identity to SEQ ID NO: 1, preferably wherein the amino acid sequence substantially retains the natural function of the protein represented by SEQ ID NO: 1.

The present invention further provides a polynucleotide comprising a nucleotide sequence encoding the retinitis pigmentosa GTPase regulator ORF15 isoform (RPGR$^{ORF15}$) or a functional variant thereof having at least 80% identity to SEQ ID NO: 1, wherein the nucleotide sequence comprises one or more, preferably all, of the nucleotides selected from: C at the position corresponding to position 30 of SEQ ID NO: 2, T at the position corresponding to position 33 of SEQ ID NO: 2, A at the position corresponding to position 966 of SEQ ID NO: 2, A at the position corresponding to position 969 of SEQ ID NO: 2, T at the position corresponding to position 1011 of SEQ ID NO:2, T at the position corresponding to position 1014 of SEQ ID NO:2, T at the position corresponding to position 1029 of SEQ ID NO:2, A at the position corresponding to position 1299 of SEQ ID NO:2, C at the position corresponding to position 1689 of SEQ ID NO:2, G at the position corresponding to position 3363 of SEQ ID NO:2, T at the position corresponding to position 3405 of SEQ ID NO:2, A at the position corresponding to position 3408 of SEQ ID NO:2, A at the position corresponding to position 3409 of SEQ ID NO:2, G at the position corresponding to position 3410 of SEQ ID NO:2, G at the position corresponding to position 3432 of SEQ ID NO:2, C at the position corresponding to position 3438 of SEQ ID NO:2 and A at the position corresponding to position 3456 of SEQ ID NO:2. The polynucleotide may comprise 2, 3, 4, 5, 6, 7, 8, 9, 10, 11, 12, 13, 14, 15, 16 or 17 of said nucleotides The invention also provides a polynucleotide comprising a nucleotide sequence encoding the retinitis pigmentosa GTPase regulator ORF15 isoform (RPGR$^{ORF15}$) or a functional variant thereof having at least 80% identity to SEQ ID NO: 1, wherein the nucleotide sequence is selected from the group consisting of:
(a) nucleotide sequence that has at least 80% identity to SEQ ID NO: 3, wherein said sequence comprises one or more, preferably all, of the nucleotides selected from: C at the position corresponding to position 30 of SEQ ID NO: 2, T at the position corresponding to position 33 of SEQ ID NO: 2, A at the position corresponding to position 48 of SEQ ID NO: 2, A at the position corresponding to position 57 of SEQ ID NO: 2, T at the position corresponding to position 60 of SEQ ID NO: 2, T at the position corresponding to position 69 of SEQ ID NO: 2, A at the position corresponding to position 72 of SEQ ID NO: 2, C at the position corresponding to position 171 of SEQ ID NO: 2, C at the position corresponding to position 189 of SEQ ID NO: 2, T at the position corresponding to position 441 of SEQ ID NO: 2, T at the position corresponding to position 537 of SEQ ID NO: 2, C at the position corresponding to position 546 of SEQ ID NO: 2, T at the position corresponding to position 786 of SEQ ID NO: 2, T at the position corresponding to position 792 of SEQ ID NO: 2, A at the position corresponding to position 966 of SEQ ID NO: 2, A at the position corresponding to position 969 of SEQ ID NO: 2, A at the position corresponding to position 990 of SEQ ID NO: 2, T at the position corresponding to position 1011 of SEQ ID NO: 2, T at the position corresponding to position 1014 of SEQ ID NO: 2, T at the position corresponding to position 1029 of SEQ ID NO: 2, A at the position corresponding to position 1299 of SEQ ID NO: 2, C at the position corresponding to position 1689 of SEQ ID NO: 2, A at the position corresponding to position 3355 of SEQ ID NO: 2, G at the position corresponding to position 3357 of SEQ ID NO: 2, G at the position corresponding to position 3363 of SEQ ID NO: 2, T at the position corresponding to position 3403 of SEQ ID NO: 2, C at the position corresponding to position 3404 of SEQ ID NO: 2, T at the position corresponding to position 3405 of SEQ ID NO: 2, A at the position corresponding to position 3408 of SEQ ID NO: 2, A at the position corresponding to position 3409 of SEQ ID NO: 2, G at the position corresponding to position 3410 of SEQ ID NO: 2, G at the position corresponding to position 3432 of SEQ ID NO: 2, C at the position corresponding to position 3438 of SEQ ID NO: 2 and A at the position corresponding to position 3456 of SEQ ID NO: 2; or (b) the nucleotide sequence of SEQ ID NO: 3. The polynucleotide may comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 of said nucleotides.

Preferably the functional variant substantially retains the natural function of the protein represented by SEQ ID NO: 1.

In one embodiment, the RPGR$^{ORF15}$-encoding nucleotide sequence of the invention comprises a nucleotide sequence that has at least 85%, 90%, 91%, 92%, 93%, 94%, 95%, 96%, 97%, 98% or 99% identity to SEQ ID NO: 3, preferably wherein the protein encoded by the nucleotide sequence substantially retains the natural function of the protein represented by SEQ ID NO: 1.

Preferably, the protein encoded by the RPGR$^{ORF15}$-encoding nucleotide sequence of the invention provides for the same or improved functioning of the cells of the retina and/or visual function as provided for by the protein represented by SEQ ID NO: 1.

In a preferred embodiment, the RPGRORF15-encoding nucleotide sequence of the invention encodes a protein of SEQ ID NO: 1.

The polynucleotide of the invention may have substantially the same or increased fidelity of replication relative to an equivalent polynucleotide comprising the human wild type RPGR$^{ORF15}$ of SEQ ID NO: 2.

The polynucleotide of the invention may have increased stability and/or be less prone to mutations occurring during cycles of polynucleotide replication relative to an equivalent polynucleotide comprising the human wild type RPGR$^{ORF15}$ of SEQ ID NO: 2.

The polynucleotide of the invention may confer higher rates of translation and/or protein expression relative to an equivalent polynucleotide comprising the human wild type RPGRORF15 of SEQ ID NO: 2.

The polynucleotide of the invention may reduce or avoid the generation of alternatively spliced variants and/or truncated proteins relative to an equivalent polynucleotide comprising the human wild type RPGR$^{ORF15}$ of SEQ ID NO: 2.

In a preferred embodiment, the RPGR$^{ORF15}$-encoding nucleotide sequence of the invention has substantially the same or increased fidelity of replication as SEQ ID NO: 3. Fidelity of replication can be measured by any of a number of methods known to the skilled person, for example the methods described herein.

In a preferred embodiment, the RPGR$^{ORF15}$-encoding nucleotide sequence of the invention comprises the nucleotide sequence of SEQ ID NO: 3.

The RPGR$^{ORF15}$-encoding nucleotide sequence may comprise fewer than 165 CpG dinucleotides and/or comprises no more than two CpG islands. CpG islands can readily be identified using routine methods, for example, using EMBOSS Cpgplot (www.ebi.ac.uk/Tools/seqstats/emboss_cpgplot/help/).

The polynucleotide of the invention may encode an RPGR$^{orf15}$ that has been shortened relative to the wild type sequence. In this regard, the codon optimization described herein is applied to the corresponding portions of the shortened sequence. Preferably, the shortened RPGR$^{orf15}$ has the ability to rescue logs of RPGR function.

The RPGR$^{orf15}$ encoding sequence of the invention may encode the shortened RPGR$^{orf15}$ disclosed in WO2016/001693.

In one embodiment, the RPGR$^{orf15}$ encoding sequence of the invention is shortened by removal of some or all of the nucleotides corresponding to positions 2485 to 2940 of SEQ ID NO:2. According to this embodiment, the RPGR$^{ORF15}$-encoding nucleotide sequence preferably does not comprise purine nucleotides at positions corresponding to nucleotides 33, 58, 59, 114, 123, 129, 181, 182, 213, 219, 226, 227, 237, 267, 285, 306, 309, 315, 324, 330, 339, 400, 401, 444, 456, 478, 480, 510, 594, 606, 618, 639, 697, 726, 744, 777, 807, 852, 877, 879, 888, 891, 921, 930, 960, 1042, 1050, 1116, 1140, 1183, 1184, 1194, 1197, 1221, 1249, 1251, 1257, 1273, 1276, 1281, 1290, 1293, 1357, 1372, 1373, 1413, 1446, 1452, 1464, 1474, 1475, 1482, 1519, 1520, 1542, 1584, 1590, 1599, 1608, 1653, 1668, 1674, 1689, 1692, 1734, 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 2121, 2167, 2169, 2190, 2193, 2208, 2229, 2259, 2283, 2298, 2323, 2343, 2346, 2361, 2373, 2382, 2388, 2403, 2409, 2410, 2412, 2448, 2457, 2472, 2476, 2478, 2958, 2970, 2997, 3033, 3039, 3069, 3075, 3117, 3129, 3156, 3166, 3235, 3246, 3273, 3285, 3306, 3321, 3369, 3399, 3405 and/or 3438 of SEQ ID NO: 2. Preferably the nucleotides at these positions correspond to those found in SEQ ID NO:3. A preferred RPGR$^{ORF15}$-encoding nucleotide sequence according to this embodiment comprises or consists of the sequence shown in SEQ ID NO:9.

The polynucleotide of the invention may comprise:
(a) a nucleotide sequence shown in SEQ ID NO:9;
(b) a nucleotide sequence comprising the sequence of SEQ ID NO:3 but with a deletion corresponding to (i) the sequence of SEQ ID NO: 10, (ii) the sequence of SEQ ID NO: 10 and up to 75 additional nucleotides flanking SEQ ID NO: 10 on one or both sides of SEQ I D NO: 10 in the sequence of SEQ ID NO: 3, or (iii) 390 or more contiguous nucleotides from within SEQ ID NO: 10; or
(c) a nucleotide sequence according to (a) or (b) but truncated at one or both of its 5' and 3' ends by up to 150 nucleotides per end.

Preferably the deletion comprises at least 400, 420 or 450 contiguous nucleotides of SEQ ID NO:10.

```
                                                             (SEQ ID NO: 9)
ATGAGAGAGCCAGAGGAGCTGATGCCAGACAGTGGAGCAGTGTTTACATTCGGAAAATCTAAGT

TCGCTGAAAATAACCCAGGAAAGTTCTGGTTTAAAAACGACGTGCCCGTCCACCTGTCTTGTGG

CGATGAGCATAGTGCCGTGGTCACTGGGAACAATAAGCTGTACATGTTCGGGTCCAACAACTGG

GGACAGCTGGGGCTGGGATCCAAATCTGCTATCTCTAAGCCAACCTGCGTGAAGGCACTGAAAC

CCGAGAAGGTCAAACTGGCCGCTTGTGGCAGAAACCACACTCTGGTGAGCACCGAGGGCGGGAA

TGTCTATGCCACCGGAGGCAACAATGAGGGACAGCTGGGACTGGGGGACACTGAGGAAAGGAAT

ACCTTTCACGTGATCTCCTTCTTTACATCTGAGCATAAGATCAAGCAGCTGAGCGCTGGCTCCA

ACACATCTGCAGCCCTGACTGAGGACGGGCGCCTGTTCATGTGGGGAGATAATTCAGAGGGCCA

GATTGGGCTGAAAAACGTGAGCAATGTGTGCGTCCCTCAGCAGGTGACCATCGGAAAGCCAGTC

AGTTGGATTTCATGTGGCTACTATCATAGCGCCTTCGTGACCACAGATGGCGAGCTGTACGTCT

TTGGGGAGCCCGAAAACGGAAAACTGGGCCTGCCTAACCAGCTGCTGGGCAATCACCGGACACC
```

-continued

```
CCAGCTGGTGTCCGAGATCCCTGAAAAAGTGATCCAGGTCGCCTGCGGGGAGAGCATACAGTG

GTCCTGACTGAGAATGCTGTGTATACCTTCGGACTGGGCCAGTTTGGCCAGCTGGGGCTGGGAA

CCTTCCTGTTTGAGACATCCGAACCAAAAGTGATCGAGAACATTCGCGACCAGACTATCAGCTA

CATTTCCTGCGGAGAGAATCACACCGCACTGATCACAGACATTGGCCTGATGTATACCTTTGGC

GATGGACGACACGGGAAGCTGGGACTGGGACTGGAGAACTTCACTAATCATTTTATCCCCACCC

TGTGTTCTAACTTCCTGCGGTTCATCGTGAAACTGGTCGCTTGCGGCGGGTGTCACATGGTGGT

CTTCGCTGCACCTCATAGGGGCGTGGCTAAGGAGATCGAATTTGACGAGATTAACGATACATGC

CTGAGCGTGGCAACTTTCCTGCCATACAGCTCCCTGACTTCTGGCAATGTGCTGCAGAGAACCC

TGAGTGCAAGGATGCGGAGAAGGGAGAGGGAACGCTCTCCTGACAGTTTCTCAATGCGACGAAC

CCTGCCACCTATCGAGGGAACACTGGGACTGAGTGCCTGCTTCCTGCCTAACTCAGTGTTTCCA

CGATGTAGCGAGCGGAATCTGCAGGAGTCTGTCCTGAGTGAGCAGGATCTGATGCAGCCAGAGG

AACCCGACTACCTGCTGGATGAGATGACCAAGGAGGCCGAAATCGACAACTCTAGTACAGTGGA

GTCCCTGGGCGAGACTACCGATATCCTGAATATGACACACATTATGTCACTGAACAGCAATGAG

AAGAGTCTGAAACTGTCACCAGTGCAGAAGCAGAAGAAACAGCAGACTATTGGCGAGCTGACTC

AGGACACCGCCCTGACAGAGAACGACGATAGCGATGAGTATGAGGAAATGTCCGAGATGAAGGA

AGGCAAAGCTTGTAAGCAGCATGTCAGTCAGGGGATCTTCATGACACAGCCAGCCACAACTATT

GAGGCTTTTTCAGACGAGGAAGTGGAGATCCCCGAGGAAAAAGAGGGCGCAGAAGATTCCAAGG

GGAATGGAATTGAGGAACAGGAGGTGGAAGCCAACGAGGAAAATGTGAAAGTCCACGGAGGCAG

GAAGGAGAAAACAGAAATCCTGTCTGACGATCTGACTGACAAGGCCGAGGTGTCCGAAGGCAAG

GCAAAATCTGTCGGAGAGGCAGAAGACGGACCAGAGGGACGAGGGGATGGAACCTGCGAGGAAG

GCTCAAGCGGGGCTGAGCATTGGCAGGACGAGGAACGAGAGAAGGGCGAAAAGGATAAAGGCCG

CGGGGAGATGGAACGACCTGGAGAGGGCGAAAAAGAGCTGGCAGAGAAGGAGGAATGGAAGAAA

AGGGACGGCGAGGAACAGGAGCAGAAAGAAAGGGAGCAGGGCCACCAGAAGGAGCGCAACCAGG

AGATGGAAGAGGGCGGCGAGGAAGAGCATGGCGAGGGAGAAGAGGAAGAGGGCGATAGAGAAGA

GGAAGAGGAAAAAGAAGGCGAAGGGAAGGAGGAAGGAGAGGGCGAGGAAGTGGAAGGCGAGAGG

GAAAAGGAGGAAGGAGAACGGAAGAAAGAGGAAAGAGCCGGCAAAGAGGAAAAGGGCGAGGAAG

AGGGCGATCAGGGCGAAGGCGAGGAGGAAGAGACCGAGGGCCGCGGGGAAGAGAAAGAGGAGGG

AGGAGAGGTGGAGGGCGGAGAGGTCGAAGAGGGAAAGGGCGAGCGCGAAGAGGGGGAGGAAGAG

GAAGGCGAAGGAGAAGGCGAGGAAGAAGAGGGAGAGGAGGAAGGCGAGGAGGAAGGAGAGGGGG

AGGAGGAGGGAGAAGGCGAGGGCGAAGAAGAAGAAGAGGGAGAAGTGGAGGGCGAAGTCGAGGG

GGAGGAGGGAGAAGGGAAGGGAGGAAGAAGAGGGCGAAGAAGAAGGCGAGGAAAGAGAAAAA

GAGGGAGAAGGCGAGGAAAACCGGAGAAATAGGGAAGAGGAGGAAGAGGAAGAGGGAAAGTACC

AGGAGACAGGCGAAGAGGAAAACGAGCGGCAGGATGGCGAGGAATATAAGAAAGTGAGCAAGAT

CAAAGGATCCGTCAAGTACGGCAAGCACAAAACCTATCAGAAGAAAAGCGTGACCAACACACAG

GGGAATGGAAAAGAGCAGAGGAGTAAGATGCCTGTGCAGTCAAAACGGCTGCTGAAGAATGGCC

CATCTGGAAGTAAAAAATTCTGGAACAATGTGCTGCCCCACTATCTGGAACTGAAATAA
```

(SEQ ID NO: 10)
```
GAAGAGGAAGAGGGCGAGGGCGAGGAAGAAGAGGGCGAGGGGGAAGAAGAGGAGGGAGAGGGCG

AAGAGGAAGAGGGGGAGGGAAAGGGCGAAGAGGAAGGAGAGGAAGGGGAGGGAGAGGAAGAGGG

GGAGGAGGGCGAGGGGGAAGGCGAGGAGGAAGAAGGAGAGGGGGAAGGCGAAGAGGAAGGCGAG

GGGGAAGGAGAGGAGGAAGAAGGGGAAGGCGAAGGCGAAGAGGAGGGAGAAGGAGAGGGGGAGG
```

-continued

```
AAGAGGAAGGAGAAGGGAAGGGCGAGGAGGAAGGCGAAGAGGGAGAGGGGAAGGCGAGGAAGA

GGAAGGCGAGGGCGAAGGAGAGGACGGCGAGGGCGAGGGAGAAGAGGAGGAAGGGGAATGGGAA

GGCGAAGAAGAGGAAGGCGAAGGCGAAGGCGAAGAAGAGGGCGAAGGGGAGGGCGAGGAGGGCG

AAGGCGAA
```

The RPGR$^{orf15}$ encoding sequence of the invention may encode the shortened RPGR$^{orf15}$ disclosed in WO2016/014353.

In one embodiment, the RPGR$^{orf15}$ encoding sequence of the invention is shortened by removal of some or all of the nucleotides corresponding to positions 2086 to 3027 of SEQ ID NO:2.

According to this embodiment, the RPGR$^{ORF15}$-encoding nucleotide sequence preferably does not comprise purine nucleotides at positions corresponding to nucleotides 33, 58, 59, 114, 123, 129, 181, 182, 213, 219, 226, 227, 237, 267, 285, 306, 309, 315, 324, 330, 339, 400, 401, 444, 456, 478, 480, 510, 594, 606, 618, 639, 697, 726, 744, 777, 807, 852, 877, 879, 888, 891, 921, 930, 960, 1042, 1050, 1116, 1140, 1183, 1184, 1194, 1197, 1221, 1249, 1251, 1257, 1273, 1276, 1281, 1290, 1293, 1357, 1372, 1373, 1413, 1446, 1452, 1464, 1474, 1475, 1482, 1519, 1520, 1542, 1584, 1590, 1599, 1608, 1653, 1668, 1674, 1689, 1692, 1734, 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 3033, 3039, 3069, 3075, 3117, 3129, 3156, 3166, 3235, 3246, 3273, 3285, 3306, 3321, 3369, 3399, 3405 and/or 3438 of SEQ ID NO: 2. Preferably the nucleotides at these positions correspond to those found in SEQ ID NO:3. A preferred RPGR$^{ORF15}$-encoding nucleotide sequence according to this embodiment comprises or consists of the sequence shown in SEQ ID NO: 11.

In one embodiment, the RPGR$^{ORF15}$-encoding nucleotide sequence comprises SEQ ID NO:3 but with a deletion corresponding to some or all of the sequence of SEQ ID NO: 12.

```
                                                       (SEQ ID NO: 11)
ATGAGAGAGCCAGAGGAGCTGATGCCAGACAGTGGAGCAGTGTTTACATTCGGAAAATCTAAGT

TCGCTGAAAATAACCCAGGAAAGTTCTGGTTTAAAAACGACGTGCCCGTCCACCTGTCTTGTGG

CGATGAGCATAGTGCCGTGGTCACTGGGAACAATAAGCTGTACATGTTCGGGTCCAACAACTGG

GGACAGCTGGGGCTGGGATCCAAATCTGCTATCTCTAAGCCAACCTGCGTGAAGGCACTGAAAC

CCGAGAAGGTCAAACTGGCCGCTTGTGGCAGAAACCACACTCTGGTGAGCACCGAGGGCGGGAA

TGTCTATGCCACCGGAGGCAACAATGAGGGACAGCTGGGGACTGGGGGACACTGAGGAAAGGAAT

ACCTTTCACGTGATCTCCTTCTTTACATCTGAGCATAAGATCAAGCAGCTGAGCGCTGGCTCCA

ACACATCTGCAGCCCTGACTGAGGACGGGCGCCTGTTCATGTGGGGAGATAATTCAGAGGGCCA

GATTGGGCTGAAAAACGTGAGCAATGTGTGCGTCCCTCAGCAGGTGACCATCGGAAAGCCAGTC

AGTTGGATTTCATGTGGCTACTATCATAGCGCCTTCGTGACCACAGATGGCGAGCTGTACGTCT

TTGGGGAGCCCGAAAACGGAAAACTGGGCCTGCCTAACCAGCTGCTGGGCAATCACCGGACACC

CCAGCTGGTGTCCGAGATCCCTGAAAAAGTGATCCAGGTCGCCTGCGGGGGAGAGCATACAGTG

GTCCTGACTGAGAATGCTGTGTATACCTTCGGACTGGGCCAGTTTGGCCAGCTGGGGCTGGGAA

CCTTCCTGTTTGAGACATCCGAACCAAAAGTGATCGAGAACATTCGCGACCAGACTATCAGCTA

CATTTCCTGCGGAGAGAATCACACCGCACTGATCACAGACATTGGCCTGATGTATACCTTTGGC

GATGGACGACACGGGAAGCTGGGACTGGGACTGGAGAACTTCACTAATCATTTTATCCCCACCC

TGTGTTCTAACTTCCTGCGGTTCATCGTGAAACTGGTCGCTTGCGGCGGGTGTCACATGGTGGT

CTTCGCTGCACCTCATAGGGGCGTGGCTAAGGAGATCGAATTTGACGAGATTAACGATACATGC

CTGAGCGTGGCAACTTTCCTGCCATACAGCTCCCTGACTTCTGGCAATGTGCTGCAGAGAACCC

TGAGTGCAAGGATGCGGAGAAGGGAGAGGGAACGCTCTCCTGACAGTTTCTCAATGCGACGAAC

CCTGCCACCTATCGAGGGAACACTGGGACTGAGTGCCTGCTTCCTGCCTAACTCAGTGTTTCCA

CGATGTAGCGAGCGGAATCTGCAGGAGTCTGTCCTGAGTGAGCAGGATCTGATGCAGCCAGAGG

AACCCGACTACCTGCTGGATGAGATGACCAAGGAGGCCGAAATCGACAACTCTAGTACAGTGGA

GTCCCTGGGCGAGACTACCGATATCCTGAATATGACACACATTATGTCACTGAACAGCAATGAG

AAGAGTCTGAAACTGTCACCAGTGCAGAAGCAGAAGAAACAGCAGACTATTGGCGAGCTGACTC
```

-continued

```
AGGACACCGCCCTGACAGAGAACGACGATAGCGATGAGTATGAGGAAATGTCCGAGATGAAGGA

AGGCAAAGCTTGTAAGCAGCATGTCAGTCAGGGGATCTTCATGACACAGCCAGCCACAACTATT

GAGGCTTTTTCAGACGAGGAAGTGGAGATCCCCGAGGAAAAAGAGGGCGCAGAAGATTCCAAGG

GGAATGGAATTGAGGAACAGGAGGTGGAAGCCAACGAGGAAAATGTGAAAGTCCACGGAGGCAG

GAAGGAGAAAACAGAAATCCTGTCTGACGATCTGACTGACAAGGCCGAGGTGTCCGAAGGCAAG

GCAAAATCTGTCGGAGAGGCAGAAGACGGACCAGAGGGACGAGGGGATGGAACCTGCGAGGAAG

GCTCAAGCGGGCTGAGCATTGGCAGGACGAGGAACGAGAGAAGGGCGAAAAGGATAAAGGCCG

CGGGGAGATGGAACGACCTGGAGAGGGCGAAAAAGAGGAAGGCGAGGGCGAAGAAGAAGAAGAG

GGAGAAGTGGAGGGCGAAGTCGAGGGGGAGGAGGGAGAAGGGGAAGGGGAGGAAGAAGAGGGCG

AAGAAGAAGGCGAGGAAAGAGAAAAGAGGGAGAAGGCGAGGAAAACCGGAGAAATAGGGAAGA

GGAGGAAGAGGAAGAGGGAAAGTACCAGGAGACAGGCGAAGAGGAAAACGAGCGGCAGGATGGC

GAGGAATATAAGAAAGTGAGCAAGATCAAAGGATCCGTCAAGTACGGCAAGCACAAAACCTATC

AGAAGAAAAGCGTGACCAACACACAGGGGAATGGAAAAGAGCAGAGGAGTAAGATGCCTGTGCA

GTCAAAACGGCTGCTGAAGAATGGCCCATCTGGAAGTAAAAAATTCTGGAACAATGTGCTGCCC

CACTATCTGGAACTGAAATAA
```

(SEQ ID NO: 12)
```
CTGGCAGAGAAGGAGGAATGGAAGAAAAGGGACGGCGAGGAACAGGAGCAGAAAGAAAGGGAGC

AGGGCCACCAGAAGGAGCGCAACCAGGAGATGGAAGAGGGCGGCGAGGAAGAGCATGGCGAGGG

AGAAGAGGAAGAGGGCGATAGAGAAGAGGAAGAGGAAAAAGAAGGCGAAGGGAAGGAGGAAGGA

GAGGGCGAGGAAGTGGAAGGCGAGAGGGAAAAGGAGGAAGGAGAACGGAAGAAAGAGGAAAGAG

CCGGCAAAGAGGAAAAGGGCGAGGAAGAGGGCGATCAGGGCGAAGGCGAGGAGGAAGAGACCGA

GGGCCGCGGGGAAGAGAAAGAGGAGGGAGGAGAGGTGGAGGGCGGAGAGGTCGAAGAGGGAAAG

GGCGAGCGCGAAGAGGAAGAGGAAGAGGGCGAGGGCGAGGAAGAAGAGGGCGAGGGGGAAGAAG

AGGAGGGAGAGGGCGAAGAGGAAGAGGGGGAGGGAAAGGGCGAAGAGGAAGGAGAGGAAGGGGA

GGGAGAGGAAGAGGGGGAGGAGGGCGAGGGGGAAGGCGAGGAGGAAGAAGGAGAGGGGGAAGGC

GAAGAGGAAGGCGAGGGGGAAGGAGAGGAGGAAGAAGGGGAAGGCGAAGGCGAAGAGGAGGGAG

AAGGAGAGGGGGAGGAAGAGGAAGGAGAAGGGAAGGGCGAGGAGGAAGGCGAAGAGGGAGAGGG

GGAAGGCGAGGAAGAGGAAGGCGAGGGCGAAGGAGAGGACGGCGAGGGCGAGGGAGAAGAGGAG

GAAGGGGAATGGGAAGGCGAAGAAGAGGAAGGCGAAGGCGAAGGCGAAGAAGAGGGCGAAGGGG

AGGGCGAGGAGGGCGAAGGCGAAGGGGAGGAAGAGGAAGGCGAAGGAGAAGGCGAGGAAGAAGA

GGGAGAGGAGGAAGGCGAGGAGGAAGGAGAGGGGGAGGAGGAGGGA
```

In another embodiment, the RPGR$^{orf15}$ encoding sequence of the invention is shortened by removal of some or all of the nucleotides corresponding to positions 2584-2961 of SEQ ID NO:2.

According to this embodiment, the RPGR$^{ORF15}$-encoding nucleotide sequence preferably does not comprise purine nucleotides at positions corresponding to nucleotides 33, 58, 59, 114, 123, 129, 181, 182, 213, 219, 226, 227, 237, 267, 285, 306, 309, 315, 324, 330, 339, 400, 401, 444, 456, 478, 480, 510, 594, 606, 618, 639, 697, 726, 744, 777, 807, 852, 877, 879, 888, 891, 921, 930, 960, 1042, 1050, 1116, 1140, 1183, 1184, 1194, 1197, 1221, 1249, 1251, 1257, 1273, 1276, 1281, 1290, 1293, 1357, 1372, 1373, 1413, 1446, 1452, 1464, 1474, 1475, 1482, 1519, 1520, 1542, 1584, 1590, 1599, 1608, 1653, 1668, 1674, 1689, 1692, 1734, 1761, 1776, 1788, 1803, 1824, 1845, 1854, 1881, 1893, 1902, 1909, 1910, 1929, 1932, 1960, 1987, 1988, 1992, 1998, 2020, 2031, 2047, 2049, 2062, 2067, 2076, 2121, 2167, 2169, 2190, 2193, 2208, 2229, 2259, 2283, 2298, 2323, 2343, 2346, 2361, 2373, 2382, 2388, 2403, 2409, 2410, 2412, 2448, 2457, 2472, 2476, 2478, 2505, 2520, 2547, 2574, 2970, 2997, 3033, 3039, 3069, 3075, 3117, 3129, 3156, 3166, 3235, 3246, 3273, 3285, 3306, 3321, 3369, 3399, 3405 and/or 3438 of SEQ ID NO: 2. Preferably the nucleotides at these positions correspond to those found in SEQ ID NO:3. A preferred RPGR$^{ORF15}$-encoding nucleotide sequence according to this embodiment comprises or consists of the sequence shown in SEQ ID NO: 13.

In one embodiment, the RPGR$^{ORF15}$-encoding nucleotide sequence comprises SEQ ID NO:3 but with a deletion corresponding to some or all of the sequence of SEQ ID NO: 14.

(SEQ ID NO: 13)
```
ATGAGAGAGCCAGAGGAGCTGATGCCAGACAGTGGAGCAGTGTTTACATTCGGAAAATCTAAGT
TCGCTGAAAATAACCCAGGAAAGTTCTGGTTTAAAAACGACGTGCCCGTCCACCTGTCTTGTGG
CGATGAGCATAGTGCCGTGGTCACTGGGAACAATAAGCTGTACATGTTCGGGTCCAACAACTGG
GGACAGCTGGGGCTGGGATCCAAATCTGCTATCTCTAAGCCAACCTGCGTGAAGGCACTGAAAC
CCGAGAAGGTCAAACTGGCCGCTTGTGGCAGAAACCACACTCTGGTGAGCACCGAGGGCGGGAA
TGTCTATGCCACCGGAGGCAACAATGAGGGACAGCTGGGACTGGGGGACACTGAGGAAAGGAAT
ACCTTTCACGTGATCTCCTTCTTTACATCTGAGCATAAGATCAAGCAGCTGAGCGCTGGCTCCA
ACACATCTGCAGCCCTGACTGAGGACGGGCGCCTGTTCATGTGGGGAGATAATTCAGAGGGCCA
GATTGGGCTGAAAAACGTGAGCAATGTGTGCGTCCCTCAGCAGGTGACCATCGGAAAGCCAGTC
AGTTGGATTTCATGTGGCTACTATCATAGCGCCTTCGTGACCACAGATGGCGAGCTGTACGTCT
TTGGGGAGCCCGAAAACGGAAAACTGGGCCTGCCTAACCAGCTGCTGGGCAATCACCGGACACC
CCAGCTGGTGTCCGAGATCCCTGAAAAAGTGATCCAGGTCGCCTGCGGGGGAGAGCATACAGTG
GTCCTGACTGAGAATGCTGTGTATACCTTCGGACTGGGCCAGTTTGGCCAGCTGGGGCTGGGAA
CCTTCCTGTTTGAGACATCCGAACCAAAAGTGATCGAGAACATTCGCGACCAGACTATCAGCTA
CATTTCCTGCGGAGAGAATCACACCGCACTGATCACAGACATTGGCCTGATGTATACCTTTGGC
GATGGACGACACGGGAAGCTGGGACTGGGACTGGAGAACTTCACTAATCATTTTATCCCCACCC
TGTGTTCTAACTTCCTGCGGTTCATCGTGAAACTGGTCGCTTGCGGCGGGTGTCACATGGTGGT
CTTCGCTGCACCTCATAGGGGCGTGGCTAAGGAGATCGAATTTGACGAGATTAACGATACATGC
CTGAGCGTGGCAACTTTCCTGCCATACAGCTCCCTGACTTCTGGCAATGTGCTGCAGAGAACCC
TGAGTGCAAGGATGCGGAGAAGGGAGAGGGAACGCTCTCCTGACAGTTTCTCAATGCGACGAAC
CCTGCCACCTATCGAGGGAACACTGGGACTGAGTGCCTGCTTCCTGCCTAACTCAGTGTTTCCA
CGATGTAGCGAGCGGAATCTGCAGGAGTCTGTCCTGAGTGAGCAGGATCTGATGCAGCCAGAGG
AACCCGACTACCTGCTGGATGAGATGACCAAGGAGGCCGAAATCGACAACTCTAGTACAGTGGA
GTCCCTGGGCGAGACTACCGATATCCTGAATATGACACACATTATGTCACTGAACAGCAATGAG
AAGAGTCTGAAACTGTCACCAGTGCAGAAGCAGAAGAAACAGCAGACTATTGGCGAGCTGACTC
AGGACACCGCCCTGACAGAGAACGACGATAGCGATGAGTATGAGGAAATGTCCGAGATGAAGGA
AGGCAAAGCTTGTAAGCAGCATGTCAGTCAGGGGATCTTCATGACACAGCCAGCCACAACTATT
GAGGCTTTTTCAGACGAGGAAGTGGAGATCCCCGAGGAAAAAGAGGGCGCAGAAGATTCCAAGG
GGAATGGAATTGAGGAACAGGAGGTGGAAGCCAACGAGGAAAATGTGAAAGTCCACGGAGGCAG
GAAGGAGAAAACAGAAATCCTGTCTGACGATCTGACTGACAAGGCCGAGGTGTCCGAAGGCAAG
GCAAAATCTGTCGGAGAGGCAGAAGACGGACCAGAGGGACGAGGGGATGGAACCTGCGAGGAAG
GCTCAAGCGGGGCTGAGCATTGGCAGGACGAGGAACGAGAGAAGGGCGAAAAGGATAAAGGCCG
CGGGGAGATGGAACGACCTGGAGAGGGCGAAAAAGAGCTGGCAGAGAAGGAGGAATGGAAGAAA
AGGGACGGCGAGGAACAGGAGCAGAAAGAAAGGGAGCAGGGCCACCAGAAGGAGCGCAACCAGG
AGATGGAAGAGGGCGGCGAGGAAGAGCATGGCGAGGGAGAAGAGGAAGAGGGCGATAGAGAAGA
GGAAGAGGAAAAGAAGGCGAAGGAAGGAGGAAGGAGAGGGCGAGGAAGTGGAAGGCGAGAGG
GAAAAGGAGGAAGGAGAACGGAAGAAAGAGGAAAGAGCCGGCAAAGAGGAAAAGGGCGAGGAAG
```

```
                              -continued
AGGGCGATCAGGGCGAAGGCGAGGAGGAAGAGACCGAGGGCCGCGGGGAAGAGAAAGAGGAGGG

AGGAGAGGTGGAGGGCGGAGAGGTCGAAGAGGGAAAGGGCGAGCGCGAAGAGGAAGAGGAAGAG

GGCGAGGGCGAGGAAGAAGAGGGCGAGGGGGAAGAAGAGGAGGGAGAGGGCGAAGAGGAAGAGG

GGGAGGGAAAGGGCGAAGAGGAAGGAGAAGGCGAGGAAGAAGAGGGAGAGGAGGAAGGCGAGGA

GGAAGGAGAGGGGAGGAGGAGGGAGAAGGCGAGGGCGAAGAAGAAGAAGAGGGAGAAGTGGAG

GGCGAAGTCGAGGGGGAGGAGGGAGAAGGGGAAGGGGAGGAAGAAGAGGGCGAAGAAGAAGGCG

AGGAAAGAGAAAAGAGGGAGAAGGCGAGGAAAACCGGAGAAATAGGGAAGAGGAGGAAGAGGA

AGAGGGAAAGTACCAGGAGACAGGCGAAGAGGAAAACGAGCGGCAGGATGGCGAGGAATATAAG

AAAGTGAGCAAGATCAAAGGATCCGTCAAGTACGGCAAGCACAAAACCTATCAGAAGAAAAGCG

TGACCAACACACAGGGGAATGGAAAAGAGCAGAGGAGTAAGATGCCTGTGCAGTCAAAACGGCT

GCTGAAGAATGGCCCATCTGGAAGTAAAAAATTCTGGAACAATGTGCTGCCCCACTATCTGGAA

CTGAAATAA
                                                        (SEQ ID NO: 14)
GGAGAGGAAGGGGAGGGAGAGGAAGAGGGGGAGGAGGGCGAGGGGGAAGGCGAGGAGGAAGAAG

GAGAGGGGGAAGGCGAAGAGGAAGGCGAGGGGGAAGGAGAGGAGGAAGAAGGGGAAGGCGAAGG

CGAAGAGGAGGGAGAAGGAGAGGGGAGGAAGAGGAAGGAGAAGGGAAGGGCGAGGAGGAAGGC

GAAGAGGGAGAGGGGAAGGCGAGGAAGAGGAAGGCGAGGGCGAAGGAGAGGACGGCGAGGGCG

AGGGAGAAGAGGAGGAAGGGGAATGGGAAGGCGAAGAAGAGGAAGGCGAAGGCGAAGGCGAAGA

AGAGGGCGAAGGGGAGGGCGAGGAGGGCGAAGGCGAAGGGGAGGAAGAGGAAGGCGAA
```

The RPGR$^{ORF15}$-encoding nucleotide sequence of the invention may be operably linked to a polynucleotide comprising a promoter element capable of driving expression of RPGR$^{ORF15}$ or a functional variant thereof in human rod and cone photoreceptor cells.

The RPGR$^{ORF15}$-encoding nucleotide sequence of the invention may be operably linked to the rhodopsin kinase (GRK1) promoter, preferably the human GRK1 promoter.

Preferably, aside from the promoter, no additional enhancer elements are used to control expression of RPGR$^{ORF15}$. Thus, in one embodiment, the nucleotide sequence of the invention does not comprise an enhancer element. In one embodiment, the nucleotide sequence does not comprise a woodchuck hepatitis postregulatory element (WPRE) element.

In another aspect, the invention provides a viral vector comprising the polynucleotide of the invention.

In one embodiment, the viral vector is an adeno-associated viral (AAV), retroviral, lentiviral or adenoviral vector.

In a preferred embodiment, the viral vector is in the form of a viral particle.

In a preferred embodiment, the viral vector is an AAV vector.

The AAV vector may be of any serotype (e.g. comprise any AAV serotype genome and/or capsid protein), provided that the vector is capable of infecting or transducing cells of the eye.

In one embodiment, the AAV vector comprises an AAV serotype 1, 2, 3, 4, 5, 6, 7, 8, 9, 10, or 11 genome. In another embodiment, the AAV vector comprises an AAV serotype 2, 4, 5 or 8 genome. Preferably, the AAV vector comprises an AAV serotype 2 genome.

In one embodiment, the AAV vector particle comprises an AAV serotype 1, 2, 3, 4, 5, 6, 7, 8, 9, 10, or 11 capsid protein. In another embodiment, the AAV vector particle comprises an AAV serotype 2, 4, 5 or 8 capsid protein. Preferably, the AAV vector particle comprises an AAV serotype 8 capsid protein. The AAV serotype 8 capsid protein may, for example, be a AAV8/Y733F mutant capsid protein.

In one embodiment, the AAV vector particle comprises an AAV2 genome and AAV2 capsid proteins (AAV2/2); an AAV2 genome and AAV5 capsid proteins (AAV2/5); or an AAV2 genome and AAV8 capsid proteins (AAV2/8). Preferably, the AAV vector particle comprises an AAV2 genome and AAV8 capsid proteins (AAV2/8).

The AAV vector particle of the invention may be a chimeric, shuffled or capsid-modified derivative of one or more naturally occurring AAVs. In particular, the AAV vector particle may comprise capsid protein sequences from different serotypes, clades, clones or isolates of AAV within the same vector (i.e. a pseudotyped vector). Thus, in one embodiment the AAV vector is in the form of a pseudotyped AAV vector particle.

In another aspect, the invention provides a viral vector production system comprising a set of polynucleotides encoding the components required for production of the viral vector, wherein the viral vector genome comprises the polynucleotide of the invention.

In one embodiment, the viral vector is an adeno-associated viral (AAV), retroviral, lentiviral or adenoviral vector. Preferably, the viral vector is an AAV vector.

In another aspect, the invention provides a DNA construct for use in the viral vector production system of the invention comprising the polynucleotide of the invention.

In another aspect, the invention provides a viral vector production cell comprising the polynucleotide, viral vector production system or DNA construct of the invention. The viral vector production cell may, for example, be a HEK293, HEK293T, Sf9, C12 or HeLa cell. Preferably, the viral vector production cell is a HEK293 or HEK293T cell.

In another aspect, the invention provides a process for producing a viral vector comprising introducing the polynucleotide of the invention into a cell and culturing the cell under conditions suitable for the production of the viral vector.

In another aspect, the invention provides a viral vector obtainable using the viral vector production cell of the invention or by the process of the invention.

In another aspect, the invention provides a cell transfected with the polynucleotide of the invention or transduced by the viral vector of the invention.

In another aspect, the invention provides a pharmaceutical composition comprising the polynucleotide, viral vector or cell of the invention in combination with a pharmaceutically acceptable carrier, diluent or excipient.

In another aspect, the invention provides the polynucleotide or viral vector of the invention for use in treating or preventing retinitis pigmentosa. The invention also provides the polynucleotide or viral vector of the invention for use in reducing photoreceptor cell death in a subject suffering from or at risk of developing retinitis pigmentosa.

In one embodiment, the retinitis pigmentosa is X-linked retinitis pigmentosa.

In one embodiment, the polynucleotide or viral vector is administered to the eye of a subject by subretinal, direct retinal or intravitreal injection. Preferably, the polynucleotide or viral vector is administered to the eye of a subject by subretinal injection. The subretinal injection may be performed using the two-step subretinal injection method described herein.

The subretinal injection preferably comprises the steps:
(a) administering a solution to the subject by subretinal injection in an amount effective to at least partially detach the retina to form a subretinal bleb, wherein the solution does not comprise the polynucleotide or viral vector; and
(b) administering a medicament composition by subretinal injection into the bleb formed by step (a), wherein the medicament comprises the polynucleotide or viral vector.

In one embodiment, the AAV vector is administered to a subject in a single dose.

The AAV vector may, for example, be in a suspension at a concentration of about $1\text{-}2\times10^9$, $1\text{-}2\times10^{10}$, $1\text{-}2\times10^{11}$, $1\text{-}2\times10^{12}$ or $1\text{-}2\times10^{13}$ genome particles (gp) per mL. Thus a dose of AAV vector of about $2\times10^{10}$ gp may, for example, be administered by injecting about a 10 μL dose of AAV vector at a concentration of about $2\times10^{12}$ gp per mL. The skilled person is readily able to adjust the dose, volume and concentration of the AAV vector as necessary.

The volume of the AAV vector administered may be, for example, about 1-500 μL, for example about 10-500, 50-500, 100-500, 200-500, 300-500, 400-500, 50-250, 100-250, 200-250, 50-150, 1-100 or 1-10 μL. The volume may be, for example, about 1, 2, 5, 10, 50, 100, 150, 200, 250, 300, 350, 400, 450 or 500 μL. Preferably, the volume of the AAV vector composition injected is about 100 μL.

In one embodiment, the AAV vector is administered at a dosage of at least $2\times10^7$, $2\times10^{08}$, $2\times10^9$, $2\times10^{10}$, $2\times10^{11}$ or $2\times10^{12}$ gp per eye. In another embodiment, the AAV vector is administered at a dosage of about $1\text{-}2\times10^7$, $1\text{-}2\times10^8$, $1\text{-}2\times10^9$, $1\text{-}2\times10^{10}$, $1\text{-}2\times10^{11}$ or $1\text{-}2\times10^{12}$ gp per eye. Preferably, the AAV vector is administered at a dosage of about $2\times10^{11}$ gp per eye, preferably by subretinal injection.

In one embodiment, photoreceptor cell degeneration due to retinitis pigmentosa is substantially prevented for the lifetime of the subject. The photoreceptor cells may comprise cone cells and/or rod cells, preferably cone and rod cells. In another embodiment, less than about 90%, 80%, 70%, 60%, 50%, 40%, 30%, 20%, 15%, 10%, 9%, 8%, 7%, 6%, 5%, 4%, 3%, 2% or 1% of the number of photoreceptor cells (e.g. cone cells and/or rod cells) present in the treated eye at the time of administration of the polynucleotide or viral (e.g. AAV) vector subsequently degenerate due to retinitis pigmentosa over the lifetime of the subject. Preferably, the surviving cells remain functional.

In one embodiment, visual function is substantially restored or maintained in the treated eye. Visual function (e.g. as determined by a test of visual function described herein) may, for example, be restored to about the same level in an affected eye as existed before the onset of retinitis pigmentosa. Alternatively, visual function may, for example, be maintained at about the same level in a healthy subject at risk of developing retinitis pigmentosa, or in a subject already suffering from retinitis pigmentosa (e.g. substantially no deterioration or further deterioration of visual function occurs as a result of retinitis pigmentosa following the administration of the polynucleotide or viral (e.g. AAV) vector of the invention).

If left untreated, most or all rod cells may degenerate (e.g. die) over time as a result of retinitis pigmentosa. Cone cells may also degenerate during progression of the disease.

In another aspect, the invention provides a method of treating or preventing retinitis pigmentosa comprising administering the polynucleotide or viral vector of the invention to a subject in need thereof. The invention also provides a method of reducing photoreceptor cell death in a subject suffering from or at risk of developing retinitis pigmentosa comprising administering the polynucleotide or viral vector of the invention to the subject.

The mode (e.g. method and dosage) and effect of administration, and the subject to be treated may be as described herein.

The invention further provides the use of the polynucleotide or viral vector of the invention for reducing or avoiding the generation of alternatively spliced variants and/or truncated $RPGR^{ORF15}$ proteins relative to a vector or polynucleotide comprising the wild type $RPGR^{ORF15}$ gene.

The invention further provides the use of the polynucleotide or viral vector of the invention for increasing the stability and/or fidelity of replication of a nucleotide sequence comprising the $RPGR^{ORF15}$ gene relative to a nucleotide sequence comprising the wild type $RPGR^{ORF15}$ gene.

The invention further provides the use of the polynucleotide or viral vector of the invention for effecting higher rates of translation and/or protein expression of $RPGR^{ORF15}$ protein relative a vector or polynucleotide comprising the wild type $RPGR^{ORF15}$ gene.

The invention further provides the use of the polynucleotide or viral vector of the invention for increasing the yield of an $RPGR^{ORF15}$-encoding nucleotide sequence relative to a nucleotide sequence comprising the wild type $RPGR^{ORF15}$ gene.

DESCRIPTION OF THE DRAWINGS

The patent or application file contains at least one drawing executed in color. Copies of this patent or patent application publication with color drawing(s) will be provided by the Office upon request and payment of the necessary fee.

Comparison of the human, mouse and dog genome sequences of RPGR.

FIG. 2

Comparison of the codon optimised (top, SEQ ID NO: 3) and wild type (bottom, SEQ ID NO: 2) RPGR$^{ORF15}$ sequences. The differences in the primary sequences are highlighted in red and underlined.

FIGS. 3A-3G

Comparison of cloning efficiency and sequence fidelity between wild type (FIG. 3A, FIG. 3B) and codon optimised (FIG. 3C, FIG. 3D) RPGR sequences in a standard cloning vector.

Comparison of plasmid yields from minipreparations (FIG. 3E) and megapreparations (FIG. 3G), and comparison of sample purity (FIG. 3F) between the same sequences.

FIGS. 4A-4B

Figure 4A:
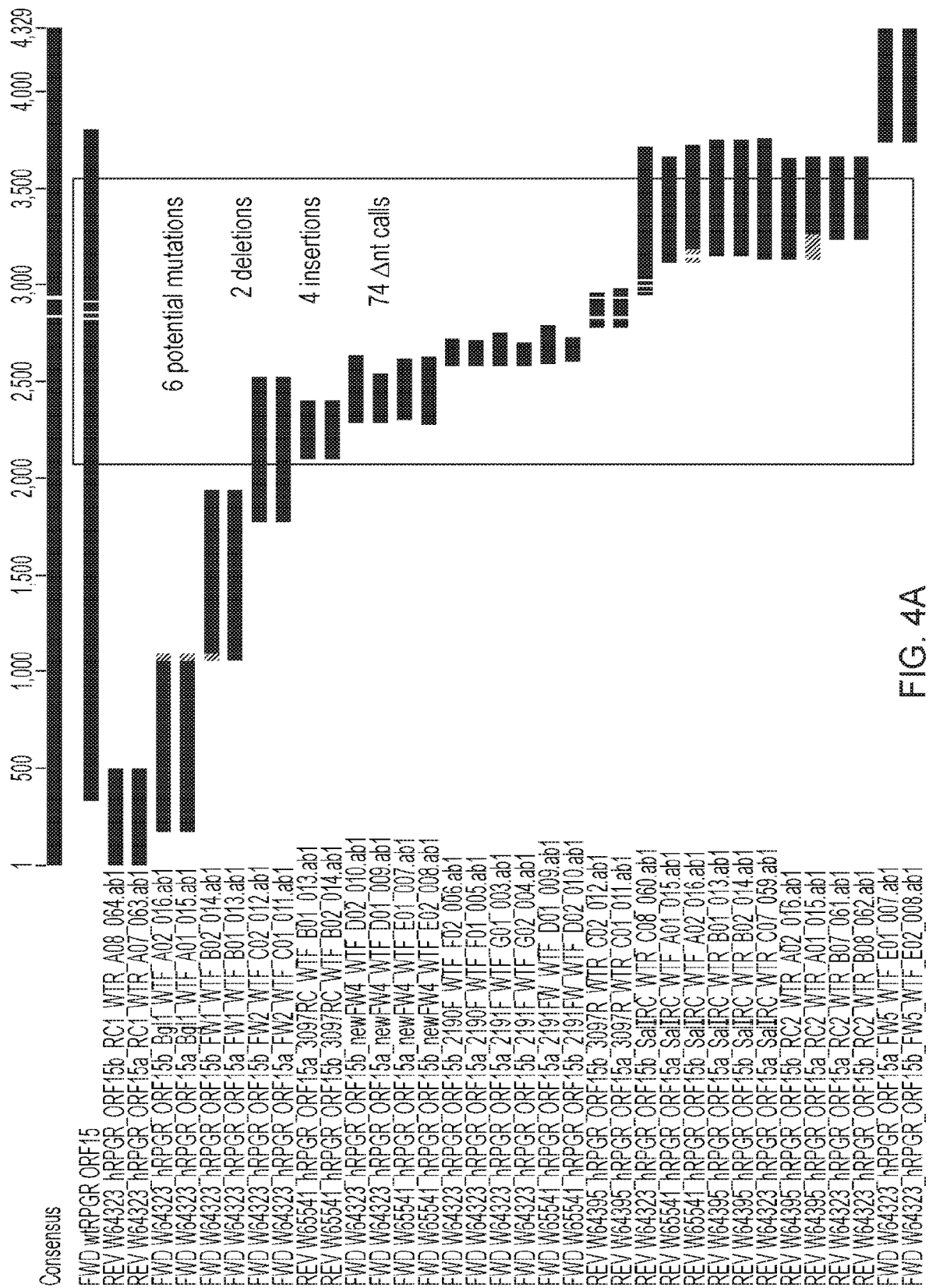
Figure 4B:
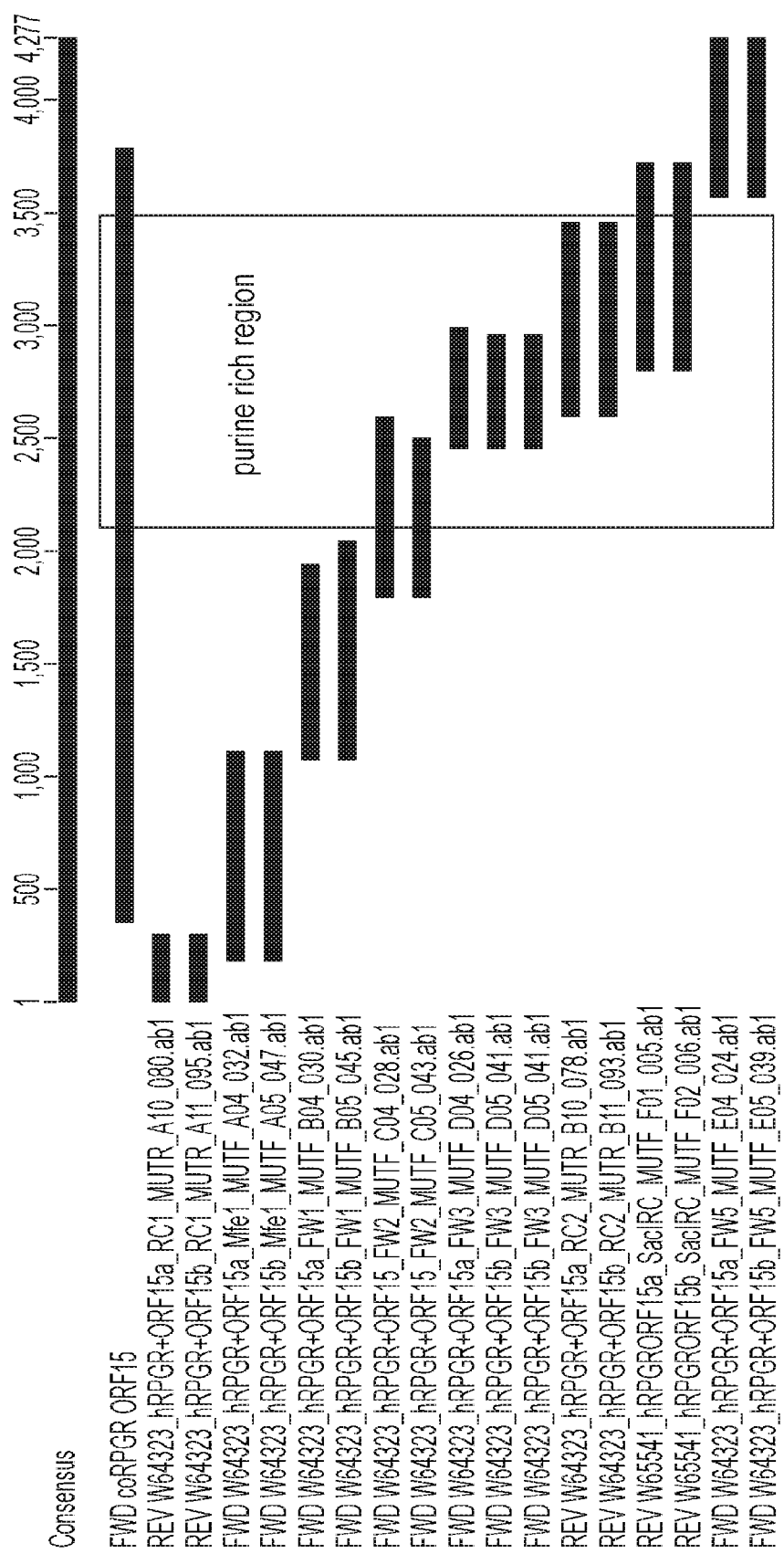

Comparison of sequence fidelity between wild type (FIG. 4A) and codon optimised (FIG. 4B) RPGR sequences in a standard cloning vector.

FIG. 5

Liquid chromatography with tandem mass spectrometry (LC/MS-MS) of the protein product of the codon optimised RPGR sequence identified approximately 80% of the amino acids of SEQ ID NO: 1 (amino acids which could not be confirmed are marked red).

FIG. 6

Western blots confirming identical molecular masses (220 kDa) of wild type and codon optimised RPGR-derived (wtRPGR and coRPGR, respectively) peptides (top panel).

A plot of the difference in Western blot signal intensity indicates approximately 4-fold higher RPGR protein production from the coRPGR sequence (bottom panel).

FIGS. 7A-7D

Overview of the treatment effect using AAV. coRPGR in a mouse model with a naturally occurring mutation in RPGR (C57BL/6$^{Rd9/Boc}$).

Figure 7:
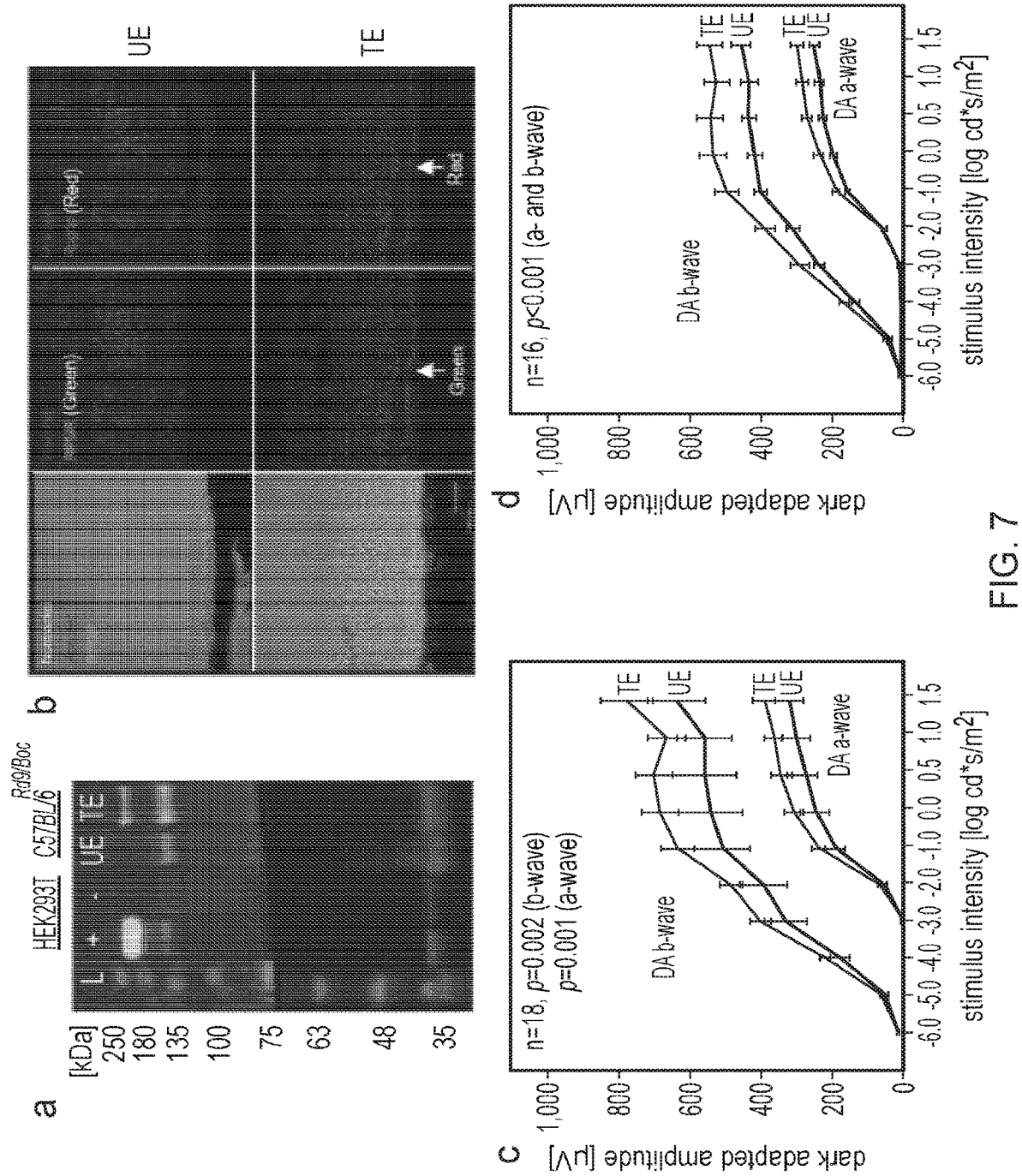

Western blot on whole retinal lysate 6 months after treatment shows the RPGR protein product at approximately 200 kDa in the treated eye (TE), but not in the untreated eye (UE) of C57BL/6$^{Rd9/Boc}$ mice (FIG. 7A). L, protein ladder; +, positive control (HEK293T cell protein lysate transfected with coRPGR expression plasmid); −, negative control (untransfected HEK293T cell protein lysate). Immunohistochemistry of unfixed cryosections 6 months after treatment (FIG. 7B). Top panel demonstrates lack of RPGR staining (green) in the untreated eye. In the treated eye (bottom), RPGR staining can be seen to co-localise to the ciliary protein Rpgrip (red). Scale bar=20 μm.

Dark adapted (DA) ERG single flash intensity series 3 (FIG. 7C) and 6 (FIG. 7D) months after treatment. Red traces of the mean are from the treated eye (TE), black traces are from the untreated eye (UE). Whiskers display 95% confidence interval.

FIG. 8

Plasmid Identity and Structural Stability, plasmid prepared from the RCB of pAAV.RK.coRPGR. Endonuclease restriction digest fragment sizes for plasmid DNA generated from the RCB for pAAV.RK.coRPGR. Expected pattern with restriction enzyme XmnI: 11+11+161+211+2681+4006 bp; SmaI: 11+11+161+211+2681+4006 bp (the 11 bp fragments pass through the agarose gel and are not visualised).
Marker 1 kbp ladder (PlasmidFactory, Item no. MSM-865-50), 300 ng
Lane 1 DNA RCB1729-151023, undigested, 250 ng
Lane 2 DNA RCB1729-151023, undigested, 250 ng
Lane 3 DNA RCB1729-151023, digested with XmnI, 250 ng
Lane 4 DNA RCB1729-151023, digested with SmaI, 250 ng

FIG. 9

Plasmid Identity and Structural Stability, for the 100 mg plasmid preparation of pAAV.RK.coRPGR. Endonuclease restriction digest fragment sizes for plasmid pAAV.RK.RPGR. Expected pattern with restriction enzyme XmnI: 11+11+161+211+2681+4006 bp (the 11 bp fragments pass through the agarose gel and are not visualised).
Marker 1 kbp ladder (PlasmidFactory, Item no. MSM-865-50), 300 ng
Lane 1 pAAV.RK.coRPGR, 250 ng
Lane 2 pAAV.RK.coRPGR, 250 ng
Marker 1 kbp ladder (PlasmidFactory, Item no. MSM-865-50), 300 ng
Lane 3 pAAV.RK.coRPGR, XmaI digestion, 250 ng
Lane 4 pAAV.RK.co.RPGR, XmaI digestion, 250 ng
Marker 1 kbp ladder (PlasmidFactory, Item no. MSM-865-50), 300 ng

FIG. 10

Plasmid DNA concentration by A260, for the 100 mg plasmid preparation of pAAV.RK.coRPGR. Calculated averaged concentration: 1.0 mg mL$^{-1}$

FIG. 11

DNA Purity. Method: UV-Scan between 220 nm and 320 nm. Determination of plasmid purity by UV between 220 nm and 320 nm, for the 100 mg plasmid preparation of pAAV.RK.coRPGR.

FIGS. 12A and 12B

Western blot analysis of RPGR$^{ORF15}$ expression in HEK293 cells. (FIG. 12A) RPGR$^{ORF15}$ (black arrow) expression was detected in cells transfected with either CAG.coRPGR$^{ORF15}$ (co) or CAG.wtRPGR$^{ORF15}$ (wt) compared to untransfected samples (UNT) in three independent experiments. (FIG. 12B) Boxplot shows the quantitation of RPGR$^{ORF15}$ expression levels by densitometry, expressed in arbitrary units (AU), after normalizing for the endogenous control (βActin).

Figure 13A:
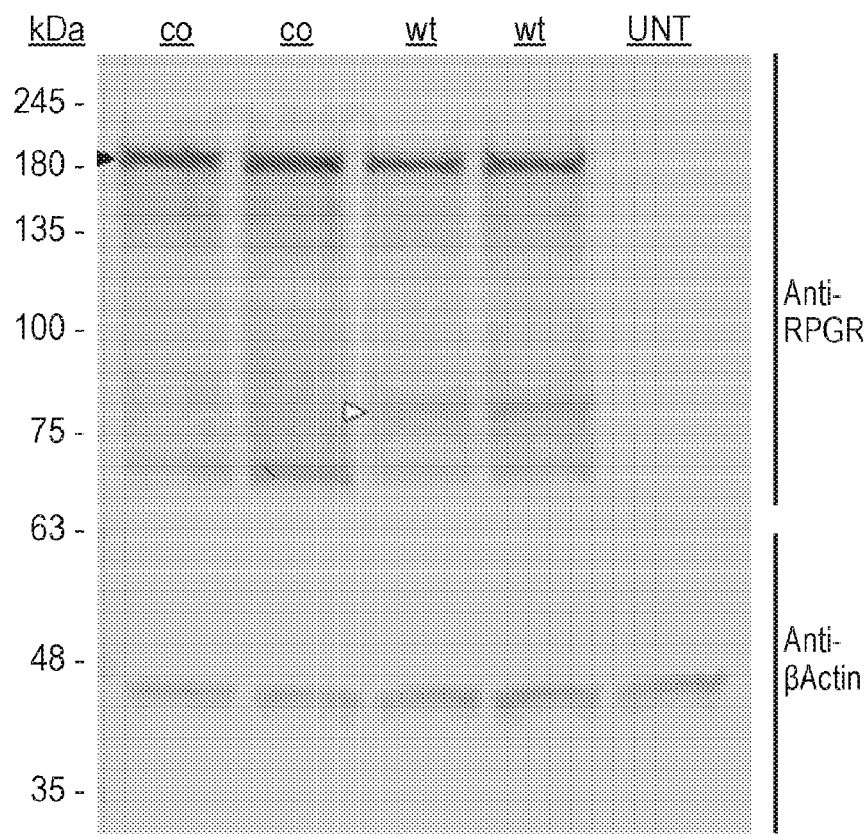
Figure 13B:
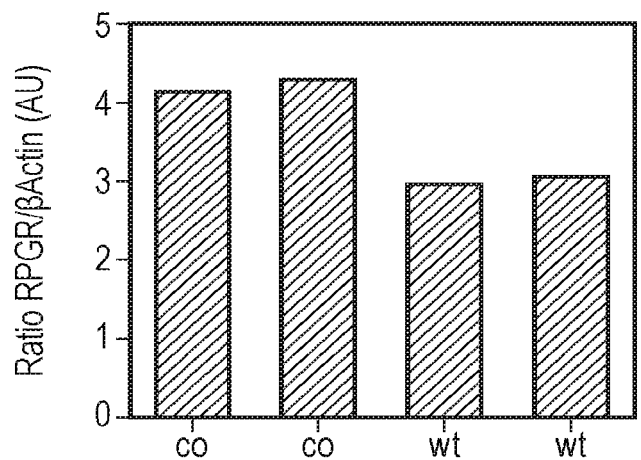

FIGS. 13A and 13B

Western blot analysis of RPGR$^{ORF15}$ expression in HEK293T cells. (FIG. 13A) RPGR$^{ORF15}$ (black arrow) expression was detected in cells transfected with either CAG.coRPGR$^{ORF15}$ (co) or CAG.wtRPGR$^{ORF15}$ (wt) compared to untransfected samples (UNT). A truncated protein (white arrow) was detected in cells transfected with the wt sequence. (FIG. 13B) Bar graph shows the quantitation of RPGR$^{ORF15}$ expression level by densitometry after normalizing for the endogenous control (βActin) in each sample.

DETAILED DESCRIPTION OF THE INVENTION

Various preferred features and embodiments of the invention will now be described by way of non-limiting examples.

The practice of the invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D.

M. and Dahlberg, J. E. (1992) Methods in Enzymology: DNA Structures Part A: Synthesis and Physical Analysis of DNA, Academic Press. Each of these general texts is herein incorporated by reference.

In one aspect, the invention provides a polynucleotide comprising a nucleotide sequence encoding the retinitis pigmentosa GTPase regulator ORF15 isoform (RPGR$^{ORF15}$), wherein the RPGR$^{ORF15}$-encoding nucleotide sequence has been codon optimised to increase fidelity of replication of the sequence.

Retinitis Pigmentosa GTPase Regulator (RPGR)

Retinitis pigmentosa GTPase regulator (RPGR) likely acts as a guanine-nucleotide releasing factor and is essential for normal vision.

Studies have suggested that RPGR plays a role in the generation of cilia, possibly through involvement in microtubule organisation and regulation of transport. Cilia are finger-like projections from the surface of a cell, which may be involved in a number of biological activities, including signalling and cell movement. Cilia are also necessary for a range of sensory perceptions, including hearing, smell and vision, and they are crucial photoreceptor cell organelles.

A number of RPGR protein isoforms are expressed from the RPGR gene. The isoform comprising the ORF15 exon is of particular relevance to the present invention and is sometimes referred to as ORF15. This isoform is referred to herein as RPGR$^{ORF15}$. RPGR$^{ORF15}$ is expressed predominantly in the retina, in particular in the photoreceptor cells, while other isoforms are expressed elsewhere and are probably also involved in cilia formation and/or function.

An example amino acid sequence of human wild type RPGR$^{ORF15}$ is:

(SEQ ID NO: 1)
MREPEELMPDSGAVFTFGKSKFAENNPGKFWFKNDVPVHLSCGDEHSAVVTGNNKLYMFG

SNNWGQLGLGSKSAISKPTCVKALKPEKVKLAACGRNHTLVSTEGGNVYATGGNNEGQLG

LGDTEERNTFHVISFFTSEHKIKQLSAGSNTSAALTEDGRLFMWGDNSEGQIGLKNVSNV

CVPQQVTIGKPVSWISCGYYHSAFVTTDGELYVFGEPENGKLGLPNQLLGNHRTPQLVSE

IPEKVIQVACGGEHTVVLTENAVYTFGLGQFGQLGLGTFLFETSEPKVIENIRDQTISYI

SCGENHTALITDIGLMYTFGDGRHGKLGLGLENFTNHFIPTLCSNFLRFIVKLVACGGCH

MVVFAAPHRGVAKEIEFDEINDTCLSVATFLPYSSLTSGNVLQRTLSARMRRRERERSPD

SFSMRRTLPPIEGTLGLSACFLPNSVFPRCSERNLQESVLSEQDLMQPEEPDYLLDEMTK

EAEIDNSSTVESLGETTDILNMTHIMSLNSNEKSLKLSPVQKQKKQQTIGELTQDTALTE

NDDSDEYEEMSEMKEGKACKQHVSQGIFMTQPATTIEAFSDEEVEIPEEKEGAEDSKGNG

IEEQEVEANEENVKVHGGRKEKTEILSDDLTDKAEVSEGKAKSVGEAEDGPEGRGDGTCE

EGSSGAEHWQDEEREKGEKDKGRGEMERPGEGEKELAEKEEWKKRDGEEQEQKEREQGHQ

KERNQEMEEGGEEEHGEGEEEEGDREEEEEKEGEGKEEGEGEEVEGEREKEEGERKKEER

AGKEEKGEEEGDQGEGEEEETEGRGEEKEEGGEVEGGEVEEGKGEREEEEEEGEGEEEEG

EGEEEEGEGEEEEGEGKGEEEGEGEGEEEGEEGEGEGEEEEGEGEGEEEGEGEGEEEEG

EGEGEEEGEGEGEEEEGEGKGEEEGEGEGEEEEGEGEGEDGEGEGEEEEGEWEGEEE

EGEGEGEEEGEGEGEEGEGEGEEEEGEGEGEEEEGEEGEEGEGEEEEGEGEGEEEEGE

VEGEVEGEEGEGEGEEEEGEEEGEEREKEGEGEENRRNREEEEEEEGKYQETGEEENERQ

DGEEYKKVSKIKGSVKYGKHKTYQKKSVTNTQGNGKEQRSKMPVQSKRLLKNGPSGSKKF

WNNVLPHYLELK

In one embodiment, the nucleotide sequence encoding human wild type RPGR$^{ORF15}$ is:

(SEQ ID NO: 2)
ATGAGGGAGCCGGAAGAGCTGATGCCCGATTCGGGTGCTGTGTTTACATTTGGGAAAAGTAA

ATTTGCTGAAAATAATCCCGGTAAATTCTGGTTTAAAAATGATGTCCCTGTACATCTTTCAT

GTGGAGATGAACATTCTGCTGTTGTTACCGGAAATAATAAACTTTACATGTTTGGCAGTAAC

AACTGGGGTCAGTTAGGATTAGGATCAAAGTCAGCCATCAGCAAGCCAACATGTGTCAAAGC

TCTAAAACCTGAAAAAGTGAAATTAGCTGCCTGTGGAAGGAACCACACCCTGGTGTCAACAG

AAGGAGGCAATGTATATGCAACTGGTGGAAATAATGAAGGACAGTTGGGGCTTGGTGACACC

GAAGAAAGAAACACTTTTCATGTAATTAGCTTTTTTACATCCGAGCATAAGATTAAGCAGCT

```
GTCTGCTGGATCTAATACTTCAGCTGCCCTAACTGAGGATGGAAGACTTTTTATGTGGGTG

ACAATTCCGAAGGGCAAATTGGTTTAAAAAATGTAAGTAATGTCTGTGTCCCTCAGCAAGTG

ACCATTGGGAAACCTGTCTCCTGGATCTCTTGTGGATATTACCATTCAGCTTTTGTAACAAC

AGATGGTGAGCTATATGTGTTTGGAGAACCTGAGAATGGGAAGTTAGGTCTTCCCAATCAGC

TCCTGGGCAATCACAGAACACCCCAGCTGGTGTCTGAAATTCCGGAGAAGGTGATCCAAGTA

GCCTGTGGTGGAGAGCATACTGTGGTTCTCACGGAGAATGCTGTGTATACCTTTGGGCTGGG

ACAATTTGGTCAGCTGGGTCTTGGCACTTTTCTTTTTGAAACTTCAGAACCCAAAGTCATTG

AGAATATTAGGGATCAAACAATAAGTTATATTTCTTGTGGAGAAAATCACACAGCTTTGATA

ACAGATATCGGCCTTATGTATACTTTTGGAGATGGTCGCCACGGAAAATTAGGACTTGGACT

GGAGAATTTTACCAATCACTTCATTCCTACTTTGTGCTCTAATTTTTTGAGGTTTATAGTTA

AATTGGTTGCTTGTGGTGGATGTCACATGGTAGTTTTTGCTGCTCCTCATCGTGGTGTGGCA

AAAGAAATTGAATTCGATGAAATAAATGATACTTGCTTATCTGTGGCGACTTTTCTGCCGTA

TAGCAGTTTAACCTCAGGAAATGTACTGCAGAGGACTCTATCAGCACGTATGCGGCGAAGAG

AGAGGGAGAGGTCTCCAGATTCTTTTTCAATGAGGAGAACACTACCTCCAATAGAAGGGACT

CTTGGCCTTTCTGCTTGTTTTCTCCCCAATTCAGTCTTTCCACGATGTTCTGAGAGAAACCT

CCAAGAGAGTGTCTTATCTGAACAGGACCTCATGCAGCCAGAGGAACCAGATTATTTGCTAG

ATGAAATGACCAAAGAAGCAGAGATAGATAATTCTTCAACTGTAGAAAGCCTTGGAGAAACT

ACTGATATCTTAAACATGACACACATCATGAGCCTGAATTCCAATGAAAAGTCATTAAAATT

ATCACCAGTTCAGAAACAAAAGAAACAACAAACAATTGGGGAACTGACGCAGGATACAGCTC

TTACTGAAAACGATGATAGTGATGAATATGAAGAAATGTCAGAAATGAAAGAAGGGAAAGCA

TGTAAACAACATGTGTCACAAGGGATTTTCATGACGCAGCCAGCTACGACTATCGAAGCATT

TTCAGATGAGGAAGTAGAGATCCCAGAGGAGAAGGAAGGAGCAGAGGATTCAAAAGGAAATG

GAATAGAGGAGCAAGAGGTAGAAGCAAATGAGGAAAATGTGAAGGTGCATGGAGGAAGAAAG

GAGAAAACAGAGATCCTATCAGATGACCTTACAGACAAAGCAGAGGTGAGTGAAGGCAAGGC

AAAATCAGTGGGAGAAGCAGAGGATGGGCCTGAAGGTAGAGGGGATGGAACCTGTGAGGAAG

GTAGTTCAGGAGCAGAACACTGGCAAGATGAGGAGAGGGAGAAGGGGAGAAAGACAAGGGT

AGAGGAGAAATGGAGAGGCCAGGAGAGGGAGAGAAGGAACTAGCAGAGAAGGAAGAATGGAA

GAAGAGGGATGGGAAGAGCAGGAGCAAAAGGAGAGGGAGCAGGGCCATCAGAAGGAAAGAA

ACCAAGAGATGGAGGAGGGAGGGGAGGAGGAGCATGGAGAAGGAGAAGAAGAGGAGGGAGAC

AGAGAAGAGGAAGAAGAGAAGGAGGGAGAAGGGAAAGAGGAAGGAGAAGGGGAAGAAGTGGA

GGGAGAACGTGAAAAGGAGGAAGGAGAGAGGAAAAAGGAGGAAAGAGCGGGGAAGGAGGAGA

AAGGAGAGGAAGAAGGAGACCAAGGAGAGGGGGAAGAGGAGGAAACAGAGGGGAGAGGGGAG

GAAAAGAGGAGGGAGGGGAAGTAGAGGGAGGGGAAGTAGAGGAGGGAAAGGAGAGAGGGA

AGAGGAAGAGGAGGAGGGTGAGGGGGAAGAGGAGGAAGGGGAGGGGGAAGAGGAGGAAGGGG

AGGGGGAAGAGGAGGAAGGAGAAGGGAAAGGGAGGAAGAAGGGAAGAAGGAGAAGGGGAG

GAAGAAGGGAGGAAGGAGAAGGGAGGGGGAAGAGGAGGAAGGAGAAGGGGAGGGAGAAGA

GGAAGGAGAAGGGAGGGAGAAGAGGAGGAAGGAGAAGGGGAGGGAGAAGAGGAAGGAGAAG

GGAGGGAGAAGAGGAGGAAGGAGAAGGGAGGAGGAAGGAGAGGAAGGAGAAGGG

GAGGGGGAAGAGGAGGAAGGAGAAGGGGAAGGGGAGGATGGAGAAGGGGAGGGGAAGAGGA

GGAAGGAGAATGGAGGGGGAAGAGGAGGAAGGAGAAGGGGAGGGGGAAGAGGAAGGAGAAG
```

-continued

```
GGGAAGGGGAGGAAGGAGAAGGGGAGGGGGAAGAGGAGGAAGGAGAAGGGGAGGGGGAAGAG

GAGGAAGGGGAAGAAGAAGGGGAGGAAGAAGGAGAGGGAGAGGAAGAAGGGGAGGGAGAAGG

GGAGGAAGAAGAGGAAGGGGAAGTGGAAGGGGAGGTGGAAGGGGAGGAAGGAGAGGGGAAG

GAGAGGAAGAGGAAGGAGAGGAGGAAGGAGAAGAAAGGGAAAAGGAGGGGGAAGGAGAAGAA

AACAGGAGGAACAGAGAAGAGGAGGAGGAAGAAGAGGGGAAGTATCAGGAGACAGGCGAAGA

AGAGAATGAAAGGCAGGATGGAGAGGAGTACAAAAAAGTGAGCAAAATAAAAGGATCTGTGA

AATATGGCAAACATAAAACATATCAAAAAAAGTCAGTTACTAACACACAGGGAAATGGGAAA

GAGCAGAGGTCCAAAATGCCAGTCCAGTCAAAACGACTTTTAAAAAACGGGCCATCAGGTTC

CAAAAAGTTCTGGAATAATGTATTACCACATTACTTGGAATTGAAGTAA
```

More than 300 mutations in the RPGR gene have been linked to X-linked retinitis pigmentosa (XLRP). Moreover, RPGR mutations are observed in approximately 70% of XLRP cases. Most XLRP-associated RPGR mutations occur in the ORF15 exon (which corresponds to nucleotides 1754-3459 of RPGR$^{ORF15}$, e.g. nucleotides 1754-3459 of SEQ ID NO: 2) and usually result in a truncated, dysfunctional protein. Mutation in RPGR likely disrupt the normal function of photoreceptor cilia, however it is unclear how this gives rise to the gradual loss of photoreceptors and resulting vision problems that are characteristic of the disease.

RPGR is a common cause of RP due to a highly mutagenic region in the purine rich region of exon 15 of the RPGR gene. Similar problems were expected to occur in AAV vector cloning if the wild-type RPGR nucleotide sequence was used for this purpose. To solve this problem we used codon-optimisation to add pyrimidine nucleotides to break up the repetitive GA sequences in exon 15 of the RPGR gene and to avoid other potential splice sites in the wt cDNA that may be responsible for a large proportion of truncated RPGR variants reported (Wu et al., Human Molecular Genetics 2015: 24(14); 3956-70). The coRPGR of the present invention was designed to avoid CpG sequences, cryptic splice sites and anomalous poly A signals.

Codon Optimisation

The RPGR$^{ORF15}$-encoding nucleotide sequence of the invention has been codon optimised with respect to the wild type gene sequence, for example the nucleotide sequence of SEQ ID NO: 2.

The codon optimised RPGR gene of the present invention made using the optimization strategy disclosed herein is therefore more stable than the wild type cDNA sequence, thereby avoiding the problems associated with wtRPGR which may generate alternatively spliced variants and truncated proteins if the wtRPGR is reintroduced into the transcriptional machinery through gene therapy (Wu et al., Human Molecular Genetics 2015: 24(14); 3956-70).

Codon optimisation takes advantage of redundancies in the genetic code to enable a nucleotide sequence to be altered while maintaining the same amino acid sequence of the encoded protein.

Typically, codon optimisation is carried out to facilitate an increase or decrease in the expression of an encoded protein. This is effected by tailoring codon usage in a nucleotide sequence to that of a specific cell type, thus taking advantage of cellular codon bias corresponding to a bias in the relative abundance of particular tRNAs in the cell type. By altering the codons in the nucleotide sequence so that they are tailored to match the relative abundance of corresponding tRNAs, it is possible to increase expression. Conversely, it is possible to decrease expression by selecting codons for which the corresponding tRNAs are known to be rare in the particular cell type.

However, the codon optimisation of the invention is not particularly targeted at influencing cellular expression levels. Instead, the invention has taken advantage of the redundancy in the genetic code to engineer the mutation-prone wild type nucleotide sequence of RPGR$^{ORF15}$ (e.g. SEQ ID NO: 2) to provide a sequence that demonstrates increased fidelity of replication (i.e. is less prone to mutations occurring during cycles of polynucleotide replication, e.g. during cloning processes or during the natural cell cycle) in comparison to the wild type sequence (e.g. SEQ ID NO: 2).

Furthermore, the present inventors having shown that: (i) it is possible to avoid alternate splice variants with the codon optimised sequence, which have been seen with non-codon optimised human cDNA RPGR constructs; and (ii) levels of protein expression from the codon optimised sequence are higher than those of the wild type sequence, thus making the construct more efficient for general translation (while not wishing to be bound by theory, this may be due to a reduction in the number of the repetitive GAN codons which use up the cellular pool of glutamate and glycine tRNAs).

The wild type ORF15 region contains far fewer T and C nucleotides than would be predicted in the genome. For instance, the 750 base pair sequence between positions 2410 and 3160 contains no C nucleotides at all in the wild type sequence. This leads to many repeating sequences that may recombine incorrectly during cloning and vector production. Since most codons start with G at position 1 in this region, the addition of C nucleotides to position 3 of the preceding codon has been done with consideration of limiting the number of CpG dinucleotides in the codon optimization strategy of the present invention. This is because too many of these dinucleotides may identify the transgene DNA as being unnatural, which may make it prone to methylation-based silencing of the C nucleotide. For instance, in the 750 base pair sequence between positions 2410 and 3160 of SEQ ID NO: 3, a total of 45 C nucleotides have been added through the codon optimisation process, resulting in 45 CpG dinucleotides (6.00%). This compares favourably to the predicted wild type frequency of these dinucleotides (6.25%).

A further reason limiting CpG dinucleotides while optimizing the codon sequence of RPGR$^{ORF15}$ is that eukaryotic cells have evolutionary conserved mechanisms of innate immunity, which serve them (or rather the surrounding cells) as defense mechanisms against e.g. viral infections (Willett et al., Frontiers in immunology 2013; 4:261). Unmethylated CpG islands can be identified as viral DNA from host cells, thereby triggering pathways (Toll-/Nod-/RIG 1-like receptor signaling etc.) potentially leading to programmed cell death (Krieg et al. The Journal of laboratory and clinical medicine 1996; 128: 128-133).

Yet further, unmethylated CpG dinucleotides can stimulate an immune response triggering inflammation.

Furthermore, the C codon optimisation has been applied where possible to the four-fold degenerate codon 'GGN', encoding glycine. This is because any subsequent methylation of the C nucleotide of the CpG dinucleotide within the transgene and subsequent deamination to thymine (T), even if it did occur, would not change the RPGR protein sequence because GGC and GGT both encode glycine.

Insertion of T nucleotides within the GA rich region of RPGR has also been limited in the nucleotide sequence of the invention to avoid creating anomalous polyA signals (e.g. AATAAA) and possible splice donor sites (GT) in the codon optimization process of the present invention. Avoiding splice donor sites is a consideration as this region contains many splice acceptor (AG) sequences with repeating G pyrimidine bases and potential A nucleotide branch points in the 5' direction. The codon optimisation pattern was extensively modelled in silico to determine the optimal modification to reduce the GA repeats and also to reduce the risk of anomalous splicing and creation of premature polyA signals. The codon optimised gene of the present invention made using the optimization strategy disclosed herein is therefore more stable than the wild type cDNA sequence, which may generate alternatively spliced variants and truncated proteins when reintroduced into the transcriptional machinery through gene therapy (Wu et al., Human Molecular Genetics 2015: 24(14); 3956-70). The codon optimized gene of the present invention thereby avoids the disease causing problems associated with wtRPGR.

The principles that have been developed and proven by the present inventors can be adapted and applied to create variants of SEQ ID NO: 3 that display similar advantageous characteristics. Accordingly, the invention should not be viewed as limited to the specific sequence of SEQ ID NO: 3.

Fidelity of replication can be measured by any of a number of methods known to the skilled person.

For example, an $RPGR^{ORF15}$-encoding nucleotide sequence may be PCR-amplified and ligated into a standard cloning vector. The ligation product may then be transformed into a cell line (e.g. standard a E. coli strain) and a number of the resulting transformant colonies may be analysed to determine the nucleotide sequence of the $RPGR^{ORF15}$ gene comprised therein. Sequencing results may be compared between different $RPGR^{ORF15}$-encoding nucleotide sequences (for example, including, a reference expected sequence) to determine the fraction of tested colonies that comprised mutated and non-mutated sequences.

In one embodiment, less than 9, for example less than 8, 7, 6, 5, 4, 3 or 2, mutations are present in the $RPGR^{ORF15}$-encoding nucleotide sequence when a polynucleotide comprising the sequence (e.g. a polynucleotide isolated from a cell colony, such as an E. coli colony, such as by isolation of a plasmid comprising the sequence from the colony) is analysed by polynucleotide sequencing, for example using the Sanger sequencing method. Preferably, 0 mutations are present when the $RPGR^{ORF15}$-encoding nucleotide sequence is sequenced.

In another embodiment, less than 25%, for example less than 20%, 15%, 10%, 9%, 8%, 7%, 6%, 5%, 4%, 3%, 2% or 1%, of tested clones (i.e. polynucleotides comprising an $RPGR^{ORF15}$-encoding nucleotide sequence of the invention isolated from a cell colony, such as plasmids isolated from an E. coli colony) comprise an $RPGR^{ORF15}$-encoding nucleotide sequence comprising at least one mutation, for example when 4, 5, 6, 7, 8, 9, 10, 20, 30, 40, 50, 100, 200, 300, 400 or 500 clones are analysed. Preferably, 0% of the tested clones comprise an RPGRORF 5-encoding nucleotide sequence comprising at least one mutation.

In one embodiment, the $RPGR^{ORF15}$-encoding nucleotide sequence of the invention has been codon optimised to reduce the number of purine nucleotides in comparison to the wild type sequence (e.g. SEQ ID NO: 2).

Adenine and guanine are the two purine nucleotides that are found in the wild type $RPGR^{ORF15}$-encoding nucleotide sequence.

In one embodiment, the number of purine nucleotides is reduced in purine-rich (i.e. GA-rich) regions of the $RPGR^{ORF15}$-encoding nucleotide sequence, for example the ORF 15 exon region.

In one embodiment, the number of purine nucleotides is reduced by at least 0.5%, 1%, 1.5%, 2%, 2.5%, 3%, 3.5%, 4%, 4.5% or 5% of the number of purine nucleotides in the wild type sequence (e.g. SEQ ID NO: 2).

In another embodiment, the number of purine nucleotides is reduced by 0.5-10%, 0.5-7.5%, 0.5-5%, 0.5-4.5%, 0.5-4%, 0.5-3.5%, 0.5-3%, 1-5%, 1-4.5%, 1-4%, 1-3.5% or 1-3% of the number of purine nucleotides in the wild type sequence (e.g. SEQ ID NO: 2).

An example codon-optimised sequence of $RPGR^{ORF15}$ of the invention is:

```
                                                        (SEQ ID NO: 3)
ATGAGAGAGCCAGAGGAGCTGATGCCAGACAGTGGAGCAGTGTTTACATTCGGAAAATCTAA

GTTCGCTGAAAATAACCCAGGAAAGTTCTGGTTTAAAAACGACGTGCCCGTCCACCTGTCTT

GTGGCGATGAGCATAGTGCCGTGGTCACTGGGAACAATAAGCTGTACATGTTCGGGTCCAAC

AACTGGGGACAGCTGGGGCTGGGATCCAAATCTGCTATCTCTAAGCCAACCTGCGTGAAGGC

ACTGAAACCCGAGAAGGTCAAACTGGCCGCTTGTGGCAGAAACCACACTCTGGTGAGCACCG

AGGGCGGGAATGTCTATGCCACCGGAGGCAACAATGAGGGACAGCTGGGACTGGGGGACACT

GAGGAAAGGAATACCTTTCACGTGATCTCCTTCTTTACATCTGAGCATAAGATCAAGCAGCT

GAGCGCTGGCTCCAACACATCTGCAGCCCTGACTGAGGACGGGCGCCTGTTCATGTGGGGAG

ATAATTCAGAGGGCCAGATTGGGCTGAAAAACGTGAGCAATGTGTGCGTCCCTCAGCAGGTG
```

-continued
```
ACCATCGGAAAGCCAGTCAGTTGGATTTCATGTGGCTACTATCATAGCGCCTTCGTGACCAC

AGATGGCGAGCTGTACGTCTTTGGGGAGCCCGAAAACGGAAAACTGGGCCTGCCTAACCAGC

TGCTGGGCAATCACCGGACACCCCAGCTGGTGTCCGAGATCCCTGAAAAAGTGATCCAGGTC

GCCTGCGGGGAGAGCATACAGTGGTCCTGACTGAGAATGCTGTGTATACCTTCGGACTGGG

CCAGTTTGGCCAGCTGGGGCTGGGAACCTTCCTGTTTGAGACATCCGAACCAAAAGTGATCG

AGAACATTCGCGACCAGACTATCAGCTACATTTCCTGCGGAGAGAATCACACCGCACTGATC

ACAGACATTGGCCTGATGTATACCTTTGGCGATGGACGACACGGGAAGCTGGGACTGGGACT

GGAGAACTTCACTAATCATTTTATCCCCACCCTGTGTTCTAACTTCCTGCGGTTCATCGTGA

AACTGGTCGCTTGCGGCGGGTGTCACATGGTGGTCTTCGCTGCACCTCATAGGGCGTGGCT

AAGGAGATCGAATTTGACGAGATTAACGATACATGCCTGAGCGTGGCAACTTTCCTGCCATA

CAGCTCCCTGACTTCTGGCAATGTGCTGCAGAGAACCCTGAGTGCAAGGATGCGGAGAAGGG

AGAGGGAACGCTCTCCTGACAGTTTCTCAATGCGACGAACCCTGCCACCTATCGAGGGAACA

CTGGGACTGAGTGCCTGCTTCCTGCCTAACTCAGTGTTTCCACGATGTAGCGAGCGGAATCT

GCAGGAGTCTGTCCTGAGTGAGCAGGATCTGATGCAGCCAGAGGAACCCGACTACCTGCTGG

ATGAGATGACCAAGGAGGCCGAAATCGACAACTCTAGTACAGTGGAGTCCCTGGGCGAGACT

ACCGATATCCTGAATATGACACACATTATGTCACTGAACAGCAATGAGAAGAGTCTGAAACT

GTCACCAGTGCAGAAGCAGAAGAAACAGCAGACTATTGGCGAGCTGACTCAGGACACCGCCC

TGACAGAGAACGACGATAGCGATGAGTATGAGGAAATGTCCGAGATGAAGGAAGGCAAAGCT

TGTAAGCAGCATGTCAGTCAGGGGATCTTCATGACACAGCCAGCCACAACTATTGAGGCTTT

TTCAGACGAGGAAGTGGAGATCCCCGAGGAAAAAGAGGGCGCAGAAGATTCCAAGGGGAATG

GAATTGAGGAACAGGAGGTGGAAGCCAACGAGGAAAATGTGAAAGTCCACGGAGGCAGGAAG

GAGAAAACAGAAATCCTGTCTGACGATCTGACTGACAAGGCCGAGGTGTCCGAAGGCAAGGC

AAAATCTGTCGGAGAGGCAGAAGACGGACCAGAGGGACGAGGGGATGGAACCTGCGAGGAAG

GCTCAAGCGGGGCTGAGCATTGGCAGGACGAGGAACGAGAGAAGGGCGAAAAGGATAAAGGC

CGCGGGGAGATGGAACGACCTGGAGAGGGCGAAAAAGAGCTGGCAGAGAAGGAGGAATGGAA

GAAAAGGGACGGCGAGGAACAGGAGCAGAAAGAAAGGGAGCAGGGCCACCAGAAGGAGCGCA

ACCAGGAGATGGAAGAGGGCGGCGAGGAAGAGCATGGCGAGGGAGAAGAGGAAGAGGGCGAT

AGAGAAGAGGAAGAGGAAAAAGAAGGCGAAGGGAAGGAGGAAGGAGAGGGCGAGGAAGTGGA

AGGCGAGAGGGAAAGGAGGAAGGAGAACGGAAGAAAGAGGAAAGAGCCGGCAAAGAGGAAA

AGGGCGAGGAAGAGGGCGATCAGGGCGAAGGCGAGGAGGAAGAGACCGAGGGCCGCGGGGAA

GAGAAAGAGGAGGGAGGAGAGGTGGAGGGCGGAGAGGTCGAAGAGGGAAAGGGCGAGCGCGA

AGAGGAAGAGGAAGAGGGCGAGGGCGAGGAAGAAGAGGGCGAGGGGGAAGAAGAGGAGGGAG

AGGGCGAAGAGGAAGAGGGGGAGGGAAAGGCGAAGAGGAAGGAGAGGAAGGGGAGGGAGAG

GAAGAGGGGAGGAGGGCGAGGGGAAGGCGAGGAGGAAGAAGGAGAGGGGAAGGCGAAGA

GGAAGGCGAGGGGAAGGAGAGGAGGAAGAAGGGAAGGCGAAGGCGAAGAGGAGGGAGAAG

GAGAGGGGAGGAAGAGGAAGGAGAAGGGAAGGCGAGGAGGAAGGCGAAGAGGGAGAGGGG

GAAGGCGAGGAAGAGGAAGGCGAGGGCGAAGGAGAGGACGGCGAGGGCGAGGGAGAAGAGGA

GGAAGGGGAATGGAAGGCGAAGAAGAGGAAGGCGAAGGCGAAGGCGAAGAAGAGGGCGAAG

GGGAGGGCGAGGAGGGCGAAGGCGAAGGGGAGGAAGAGGAAGGCGAAGGAGAAGGCGAGGAA

GAAGAGGGAGAGGAGGAAGGCGAGGAGGAAGGAGAGGGGGAGGAGGAGGGAGAAGGCGAGGG

CGAAGAAGAAGAAGAGGGAGAAGTGGAGGGCGAAGTCGAGGGGGAGGAGGGAGAAGGGGAAG
```

-continued

```
GGGAGGAAGAAGAGGGCGAAGAAGAAGGCGAGGAAAGAGAAAAAGAGGGAGAAGGCGAGGAA

AACCGGAGAAATAGGGAAGAGGAGGAAGAGGAAGAGGGAAAAGTACCAGGAGACAGGCGAGA

GGAAAACGAGCGGCAGGATGGCGAGGAATATAAGAAAGTGAGCAAGATCAAAGGATCCGTCA

AGTACGGCAAGCACAAAACCTATCAGAAGAAAAGCGTGACCAACACACAGGGGAATGGAAAA

GAGCAGAGGAGTAAGATGCCTGTGCAGTCAAAACGGCTGCTGAAGAATGGCCCATCTGGAAG

TAAAAAATTCTGGAACAATGTGCTGCCCCACTATCTGGAACTGAAATAA
```

In another embodiment, the RPGR$^{ORF15}$-encoding nucleotide sequence of the invention comprises a sequence selected from the group consisting of:
(a) a nucleotide sequence encoding an amino acid sequence that has at least 80% identity to SEQ ID NO: 1;
(b) a nucleotide sequence that has at least 80% identity to SEQ ID NO: 3; and
(c) the nucleotide sequence of SEQ ID NO: 3,
preferably wherein the protein encoded by the nucleotide sequence substantially retains the natural function of the protein represented by SEQ ID NO: 1.

In another embodiment, the RPGR$^{ORF15}$-encoding nucleotide sequence of the invention comprises a nucleotide sequence encoding an amino acid sequence that has at least 85%, 90%, 91%, 92%, 93%, 94%, 95%, 96%, 97%, 98%, 99% or 100% identity to SEQ ID NO: 1, preferably wherein the amino acid sequence substantially retains the natural function of the protein represented by SEQ ID NO: 1.

In another embodiment, the RPGR$^{ORF15}$-encoding nucleotide sequence of the invention comprises a nucleotide sequence that has at least 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identity to SEQ ID NO: 3, preferably wherein the protein encoded by the nucleotide sequence substantially retains the natural function of the protein represented by SEQ ID NO: 1.

In a preferred embodiment, the RPGR$^{ORF15}$-encoding nucleotide sequence of the invention comprises the nucleotide sequence of SEQ ID NO: 3.

Preferably, the RPGR$^{ORF15}$-encoding nucleotide sequence of the invention encodes a protein which assists in providing similar or higher prevention of:
(a) the clinical appearance of the retinal pigment changes that are associated with RP;
(b) photoreceptor (e.g. cone cell, preferably cone and rod cell) cell death; and/or
(c) deterioration in visual function
in a subject suffering from or at risk of developing retinitis pigmentosa compared to the protein of SEQ ID NO: 1.

As used herein, the nucleotide symbol "N" indicates any nucleotide may be present at that position (e.g. G, A, T or C), following the 1UPAC-IUB convention.

Retinitis Pigmentosa

Retinitis pigmentosa (RP) is a phenotypically linked group of inherited retinal dystrophies, which is commonly caused by the progressive degeneration of rod photoreceptor cells. The retinal pigment epithelium (RPE) and cone photoreceptor cells may also degenerate during progression of the disease.

X-linked retinitis pigmentosa (XLRP), a form of the disease inherited in an X chromosome-linked pattern (i.e. genes associated with the disease are located on the X chromosome), is regarded as the most severe form of retinitis pigmentosa.

RP is characterised in clinical appearance by changes in the pigment of the retina, which may be accompanied by arteriolar attenuation and optic nerve atrophy. Changes in the retina may result from dispersion and aggregation of the retinal pigment. This may give rise to an appearance ranging from granular or mottled to distinctive focal aggregates resembling bone spicules. Black or dark brown star-shaped concentrations of pigment may appear. Furthermore, pigmentation limited to one quadrant of the retina, abnormalities which appear to be radiating out from the disc and changes associated with severe vasculopathy may be observed.

The treatment or prevention of RP described herein may reduce or prevent the appearance of the RP phenotype described above. It may result in protection of the photoreceptor cells, such as the cone cells, from degeneration. Preferably, the treatment protects both cone and rod cells from degeneration.

Numbers of rods and cones can be estimated by the skilled person in the clinic using techniques such as adaptive optics, autofluorescence and optical coherence tomography (OCT) scans.

Preferably, the treatment of RP enables maintenance or improvement in visual function.

Visualisation of the appearance of a retina and assessment of visual function may be readily carried out by the skilled person. For example, visual function tests that might be carried out by the skilled person include best corrected visual acuity, visual field testing, micro perimetry, colour vision, dark adaptometry, electroretinography and cone flicker fusion tests. As used herein, "maintenance or improvement in visual function" is to be understood as the maintenance of substantially the same level or an improvement in the level of vision as assessed by one or more such test of visual function, when the vision in a treated eye is compared before and after the methods of the invention have been performed.

Structure of the Eye

The medicaments disclosed herein may be delivered to a mammalian, preferably human eye in relation to the treatment or prevention of retinitis pigmentosa (RP).

The person skilled in the treatment of diseases of the eye will have a detailed and thorough understanding of the structure of the eye. However, the following structures of particular relevance to the invention are described.

Retina

The retina is the multi-layered membrane, which lines the inner posterior chamber of the eye and senses an image of the visual world which is communicated to the brain via the optic nerve. In order from the inside to the outside of the eye, the retina comprises the layers of the neurosensory retina and retinal pigment epithelium, with the choroid lying outside the retinal pigment epithelium.

Neurosensory Retina and Photoreceptor Cells

The neurosensory retina harbours the photoreceptor cells that directly sense light. It comprises the following layers: internal limiting membrane (ILM); nerve fibre layer; ganglion cell layer; inner plexiform layer; inner nuclear layer; outer plexiform layer; outer nuclear layer (nuclei of the photoreceptors); external limiting membrane (ELM); and photoreceptors (inner and outer segments) of the rods and cones.

The skilled person will have a detailed understanding of photoreceptor cells. Briefly, photoreceptor cells are specialised neurons located in the retina that convert light into biological signals. Photoreceptor cells comprise rod and cone cells, which are distributed differently across the retina.

Rod cells are distributed mainly across the outer parts of the retina. They are highly sensitive and provide for vision at low light levels. There are on average about 125 million rod cells in a normal human retina.

Cone cells are found across the retina, but are particular highly concentrated in the fovea, a pit in the neurosensory retina that is responsible for central high resolution vision. Cone cells are less sensitive than rod cells. There are on average about 6-7 million cone cells in a normal human retina.

Retinal Pigment Epithelium

The retinal pigment epithelium (RPE) is a pigmented layer of cells located immediately to the outside of the neurosensory retina. The RPE performs a number of functions, including transport of nutrients and other substances to the photoreceptor cells, and absorption of scattered light to improve vision.

Choroid

The choroid is the vascular layer situated between the RPE and the outer sclera of the eye. The vasculature of the choroid enables provision of oxygen and nutrients to the retina.

Vectors

A vector is a tool that allows or facilitates the transfer of an entity from one environment to another. In accordance with the invention, and by way of example, some vectors used in recombinant nucleic acid techniques allow entities, such as a segment of nucleic acid (e.g. a heterologous DNA segment, such as a heterologous cDNA segment), to be transferred into a target cell. The vector may serve the purpose of maintaining the heterologous nucleic acid (e.g. DNA or RNA) within the cell, facilitating the replication of the vector comprising a segment of nucleic acid or facilitating the expression of the protein encoded by a segment of nucleic acid.

Vectors may be non-viral or viral. Examples of vectors used in recombinant nucleic acid techniques include, but are not limited to, plasmids, chromosomes, artificial chromosomes and viruses. The vector may also be, for example, a naked nucleic acid (e.g. DNA or RNA). In its simplest form, the vector may itself be a nucleotide of interest.

In one aspect, the invention provides a vector comprising the polynucleotide of the invention.

The vectors used in the invention may be, for example, plasmid or viral vectors and may include a promoter for the expression of a polynucleotide and optionally a regulator of the promoter.

Viral Vectors

In a preferred embodiment, the vector of the invention is a viral vector. Preferably, the viral vector is in the form of a viral vector particle.

The viral vector may be, for example, an adeno-associated viral (AAV), retroviral, lentiviral or adenoviral vector.

The skilled person is readily able to select a suitable virus for a required purpose as a vector in the invention, for example based on the size and type of the transgene to be delivered and the type of target cell. Furthermore, methods of preparing and modifying viral vectors and viral vector particles, such as those derived from AAV, retroviruses, lentiviruses or adenoviruses, are well known in the art and can be readily adapted by the skilled person to the required purpose.

Adeno-associated Viral (AAV) Vectors

In a preferred embodiment, the vector of the invention is an adeno-associated viral (AAV) vector. Preferably, the AAV vector is in the form of an AAV particle.

The AAV vector may comprise an AAV genome or a derivative thereof.

An AAV genome is a polynucleotide sequence, which encodes functions needed for production of an AAV particle. These functions include those operating in the replication and packaging cycle of AAV in a host cell, including encapsidation of the AAV genome into an AAV particle. Naturally occurring AAVs are replication-deficient and rely on the provision of helper functions in trans for completion of a replication and packaging cycle. Accordingly, the AAV genome of the vector of the invention is typically replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype, isolate or clade of AAV. Thus, the AAV genome may be the full genome of a naturally occurring AAV. As is known to the skilled person, AAVs occurring in nature may be classified according to various biological systems.

Commonly, AAVs are referred to in terms of their serotype. A serotype corresponds to a variant subspecies of AAV which, owing to its profile of expression of capsid surface antigens, has a distinctive reactivity which can be used to distinguish it from other variant subspecies. Typically, a virus having a particular AAV serotype does not efficiently cross-react with neutralising antibodies specific for any other AAV serotype.

AAV serotypes include AAV1, AAV2, AAV3, AAV4, AAV5, AAV6, AAV7, AAV8, AAV9, AAV10 and AAV11, and also recombinant serotypes, such as Rec2 and Rec3, recently identified from primate brain. Any of these AAV serotypes may be used in the invention. Thus, in one embodiment of the invention, the AAV vector particle is an AAV1, AAV2, AAV3, AAV4, AAV5, AAV6, AAV7, AAV8, AAV9, AAV10, AAV11, Rec2 or Rec3 AAV vector particle.

Reviews of AAV serotypes may be found in Choi et al. (2005) Curr. Gene Ther. 5: 299-310 and Wu et al. (2006) Molecular Therapy 14: 316-27. The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV may also be referred to in terms of clades or clones. This refers to the phylogenetic relationship of naturally derived AAVs, and typically to a phylogenetic group of AAVs which can be traced back to a common ancestor, and includes all descendants thereof. Additionally, AAVs may be referred to in terms of a specific isolate, i.e. a genetic isolate of a specific AAV found in nature. The term genetic isolate describes a population of AAVs which has undergone limited genetic mixing with other naturally occurring AAVs, thereby defining a recognisably distinct population at a genetic level.

The skilled person can select an appropriate serotype, clade, clone or isolate of AAV for use in the invention on the basis of their common general knowledge. For instance, the AAV5 capsid has been shown to transduce primate cone photoreceptors efficiently as evidenced by the successful correction of an inherited colour vision defect (Mancuso et al. (2009) Nature 461: 784-7).

The AAV serotype determines the tissue specificity of infection (or tropism) of an AAV virus. Accordingly, preferred AAV serotypes for use in AAVs administered to patients in accordance with the invention are those which have natural tropism for or a high efficiency of infection of target cells within the eye. In one embodiment, AAV serotypes for use in the invention are those which infect cells of the neurosensory retina, retinal pigment epithelium and/or choroid.

Typically, the AAV genome of a naturally derived serotype, isolate or clade of AAV comprises at least one inverted terminal repeat sequence (ITR). An ITR sequence acts in cis to provide a functional origin of replication and allows for integration and excision of the vector from the genome of a cell. In preferred embodiments, one or more ITR sequences flank the nucleotide sequence encoding the RPGR$^{ORF15}$. The AAV genome typically also comprises packaging genes, such as rep and/or cap genes which encode packaging functions for an AAV particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV particle. Capsid variants are discussed below.

A promoter will be operably linked to each of the packaging genes. Specific examples of such promoters include the p5, p19 and p40 promoters (Laughlin et al. (1979) Proc. Natl. Acad. Sci. USA 76: 5567-5571). For example, the p5 and p19 promoters are generally used to express the rep gene, while the p40 promoter is generally used to express the cap gene.

As discussed above, the AAV genome used in the vector of the invention may therefore be the full genome of a naturally occurring AAV. For example, a vector comprising a full AAV genome may be used to prepare an AAV vector or vector particle in vitro. However, while such a vector may in principle be administered to patients, this will rarely be done in practice. Preferably the AAV genome will be derivatised for the purpose of administration to patients. Such derivatisation is standard in the art and the invention encompasses the use of any known derivative of an AAV genome, and derivatives which could be generated by applying techniques known in the art. Derivatisation of the AAV genome and of the AAV capsid are reviewed in Coura and Nardi (2007) Virology Journal 4: 99, and in Choi et al. and Wu et al., referenced above.

Derivatives of an AAV genome include any truncated or modified forms of an AAV genome which allow for expression of a transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences, i.e. a self-complementary AAV genome. This allows for bypass of DNA replication in the target cell, and so enables accelerated transgene expression.

The one or more ITRs will preferably flank the nucleotide sequence encoding the RPGR$^{ORF15}$ at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

The following portions could therefore be removed in a derivative of the invention: one inverted terminal repeat (ITR) sequence, the replication (rep) and capsid (cap) genes. However, in some embodiments, derivatives may additionally include one or more rep and/or cap genes or other viral sequences of an AAV genome. Naturally occurring AAV integrates with a high frequency at a specific site on human chromosome 19, and shows a negligible frequency of random integration, such that retention of an integrative capacity in the vector may be tolerated in a therapeutic setting.

Where a derivative comprises capsid proteins i.e. VP1, VP2 and/or VP3, the derivative may be a chimeric, shuffled or capsid-modified derivative of one or more naturally occurring AAVs. In particular, the invention encompasses the provision of capsid protein sequences from different serotypes, clades, clones, or isolates of AAV within the same vector (i.e. a pseudotyped vector).

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are co-transfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al. (2008) ARVO Abstract: D1048). The unrelated protein may also be one which assists purification of the viral particle as part of the production process, i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al., referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention may take the form of a nucleotide sequence comprising an AAV genome or derivative thereof and a sequence encoding the RPGR$^{ORF15}$ transgene or a variant thereof.

The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral capsid. The AAV particle also includes chemically modified forms bearing ligands adsorbed to the capsid surface. For example, such ligands may include antibodies for targeting a particular cell surface receptor.

Thus, for example, the AAV particles of the invention include those with an AAV2 genome and AAV2 capsid proteins (AAV2/2), those with an AAV2 genome and AAV5 capsid proteins (AAV2/5) and those with an AAV2 genome and AAV8 capsid proteins (AAV2/8).

Retroviral and Lentiviral Vectors

In another embodiment of the invention, the viral vector is a retroviral vector.

Retroviruses and lentiviruses have been adapted for use as gene therapy vectors for a wide range of purposes.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) Retroviruses, pp. 758-763, Cold Spring Harbor Laboratory Press, Eds: J. M. Coffin, S. M. Hughes, H. E. Varmus.

The retroviral vector used in the invention may be derived from or may be derivable from any suitable retrovirus. A large number of different retroviruses have been identified and the skilled person is well able to select a suitable retrovirus for a particular purpose. Examples include: murine leukaemia virus (MLV), human T-cell leukaemia virus (HTLV), mouse mammary tumour virus (MMTV), Rous sarcoma virus (RSV), Fujinami sarcoma virus (FuSV), Moloney murine leukaemia virus (MoMLV), FBR murine osteosarcoma virus (FBR MSV), Moloney murine sarcoma virus (Mo-MSV), Abelson murine leukaemia virus (A-MLV), Avian myelocytomatosis virus-29 (MC29) and Avian erythroblastosis virus (AEV). A detailed list of retroviruses may be found in Coffin, J. M. et al. (1997) Retroviruses, pp. 758-763, Cold Spring Harbor Laboratory Press, Eds: J. M. Coffin, S. M. Hughes, H. E. Varmus.

In another embodiment of the invention, the viral vector is a lentiviral vector.

Lentiviral vectors are part of the larger group of retroviral vectors. A detailed list of lentiviruses may be found in Coffin, J. M. et al. (1997) Retroviruses, pp. 758-763, Cold Spring Harbor Laboratory Press, Eds: J. M. Coffin, S. M. Hughes, H. E. Varmus. In brief, lentiviruses can be divided into primate and non-primate groups. Examples of primate lentiviruses include but are not limited to: the human immunodeficiency virus (HIV), the causative agent of human auto-immunodeficiency syndrome (AIDS); and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

Adenoviral Vectors

In another embodiment of the invention, the viral vector is an adenoviral vector.

The adenovirus is a double-stranded, linear DNA virus that does not go through an RNA intermediate. There are over 50 different human serotypes of adenovirus divided into 6 subgroups based on the genetic sequence homology. The natural targets of adenovirus are the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses have been used as vectors for gene therapy and for expression of heterologous genes. The large (36 kb) genome can accommodate up to 8 kb of foreign insert DNA and is able to replicate efficiently in complementing cell lines to produce very high titres of up to $10^{12}$. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, they function episomally (independently from the host genome) as a linear genome in the host nucleus. Hence the use of recombinant adenovirus alleviates the problems associated with random integration into the host genome.

Promoters and Regulatory Sequences

The vector of the invention may also include elements allowing for the expression of the RPGR$^{ORF15}$ transgene in vitro or in vivo. These may be referred to as expression control sequences. Thus, the vector typically comprises expression control sequences (e.g. comprising a promoter sequence) operably linked to the nucleotide sequence encoding the transgene.

Any suitable promoter may be used, the selection of which may be readily made by the skilled person. The promoter sequence may be constitutively active (i.e. operational in any host cell background), or alternatively may be active only in a specific host cell environment, thus allowing for targeted expression of the transgene in a particular cell type (e.g. a tissue-specific promoter). The promoter may show inducible expression in response to presence of another factor, for example a factor present in a host cell. In any event, where the vector is administered for therapy, it is preferred that the promoter should be functional in the target cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters include the chicken beta-actin (CBA) promoter, optionally in combination with a cytomegalovirus (CMV) enhancer element. An example promoter for use in the invention is a hybrid CBA/CAG promoter, for example the promoter used in the rAVE expression cassette (GeneDetect.com). A further example promoter for use in the invention has the sequence:

```
                                                         (SEQ ID NO: 4)
ATTGACGTCAATAATGACGTATGTTCCCATAGTAACGCCAATAGGGACTTTCCATTGACGTCAATGGGTGGAGT

ATTTACGGTAAACTGCCCACTTGGCAGTACATCAAGTGTATCATATGCCAAGTACGCCCCCTATTGACGTCAAT

GACGGTAAATGGCCCGCCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTCCCCATCTCCCCCCCCT

CCCCACCCCCAATTTTGTATTTATTTATTTTTTAATTATTTTGTGCAGCGATGGGGCGGGGGGGGGGGGGGG

CGCGCGCCAGGCGGGGCGGGGCGGGCGAGGGCGGGCGGGCGAGGCGGAGAGGTGCGGCGGCAGCCAATCA

GAGCGGCGCGCTCCGAAAGTTTCCTTTTATGGCGAGGCGGCGGCGGCGGCGGCCCTATAAAAAGCGAAGCGCGC

GGCGGGCGGGAGTCGCTGCGCGCTGCCTTCGCCCCGTGCCCCGCTCCGCCGCCGCCTCGCGCCGCCCGCCCCGG

CTCTGACTGACCGCGTTACTCCCACAGGTGAGCGGGCGGGACGGCCCTTCTCCTCCGGGCTGTAATTAGCGCTT

GGTTTAATGACGGCTTGTTTCTTTTCTGTGGCTGCGTGAAAGCCTTGAGGGGCTCCGGGAGGGCCCTTTGTGCG

GGGGGAGCGGCTCGGGGCTGTCCGCGGGGGACGGCTGCCTTCGGGGGGGACGGGGCAGGGCGGGGTTCGGCTT

CTGGCGTGTGACCGGCGGCTCTAGAGCCTCTGCTAACCATGTTCATGCCTTCTTCTTTTTCCTACAGCTCCTGG

GCAACGTGCTGGTTATTGTGCTGTCTCATCATTTTGGCAAAGAATT
```

Examples of promoters based on human sequences that would induce retina-specific gene expression include rhodopsin kinase for rods and cones (Allocca et al. (2007) J. Virol. 81: 11372-80), PR2.1 for cones only (Mancuso et al. (2009) Nature 461: 784-7) and/or RPE65 for the retinal pigment epithelium (Bainbridge et al. (2008) N. Engl. J. Med. 358: 2231-9). In some embodiments, the RPGR$^{ORF15}$-encoding polynucleotide is operably linked to the, preferably human, rhodopsin kinase (GRK1) promoter, which may comprise the nucleotide sequence of SEQ ID NO: 7, or a functional variant having at least 90 or 95% identity thereto.

```
                                              (SEQ ID NO: 7)
GGGCCCCAGAAGCCTGGTGGTTGTTTGTCCTTCTCAGGGGAAAAGTGAGG

CGGCCCCTTGGAGGAAGGGGCCGGGCAGAATGATCTAATCGGATTCCAAG

CAGCTCAGGGGATTGTCTTTTTCTAGCACCTTCTTGCCACTCCTAAGCGT

CCTCCGTGACCCCGGCTGGGATTTAGCCTGGTGCTGTGTCAGCCCCGGG
```

In other embodiments the promoter element to which the RPGR$^{ORF15}$-encoding polynucleotide is operably linked is the, preferably human, interphotoreceptor retinoid-binding protein (IRBP) promoter, which may comprise the nucleic acid sequence of SEQ ID NO: 8 or a functional variant having at least 90 or 95% identity thereto.

(SEQ ID NO: 8)
agcacagtgtctggcatgtagcaggaactaaaataatggcagtgattaat gttatgatatgcagacacaacacagcaagataagatgcaatgtaccttct gggtcaaaccacc ctggccactcctccccgatacccagggttgatgtgct tgaattagacaggattaaaggcttactggagctggaagccttgccccaac tcaggagtttagccccagaccttctgtccaccagc Preferably, aside from the promoter, no additional regulatory elements are used to control expression of RPGR$^{ORF15}$.

However, the vector of the invention may also comprise one or more additional regulatory sequences which may act pre- or post-transcriptionally. The regulatory sequence may be part of the native transgene locus or may be a heterologous regulatory sequence. The vector of the invention may comprise portions of the 5'-UTR or 3'-UTR from the native transgene transcript.

Regulatory sequences are any sequences which facilitate expression of the transgene, i.e. act to increase expression of a transcript, improve nuclear export of mRNA or enhance its stability. Such regulatory sequences include for example enhancer elements, postregulatory elements and polyadenylation sites. A preferred polyadenylation site is the Bovine Growth Hormone poly-A signal which may be as shown below:

(SEQ ID NO: 5)
TCGCTGATCAGCCTCGACTGTGCCTTCTAGTTGCCAGCCATCTGTTGTTT

GCCCCTCCCCCGTGCCTTCCTTGACCCTGGAAGGTGCCACTCCCACTGTC

CTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGG

AAGACAATAGCAGGCATGCTGGGGATGCGGTGGGCTCTATGGCTTCTGAG

GCGGAAAGAACCAGCTGGGG

In the context of the vector of the invention, such regulatory sequences will be cis-acting. However, the invention also encompasses the use of trans-acting regulatory sequences located on additional genetic constructs.

A preferred post-regulatory element for use in a vector of the invention is the woodchuck hepatitis postregulatory element (WPRE) or a variant thereof. An example sequence of the WPRE is shown below:

(SEQ ID NO: 6)
ATCAACCTCTGGATTACAAAATTTGTGAAAGATTGACTGGTATTCTTAAC

TATGTTGCTCCTTTTACGCTATGTGGATACGCTGCTTTAATGCCTTTGTA

TCATGCTATTGCTTCCCGTATGGCTTTCATTTTCTCCTCCTTGTATAAAT

CCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCAT

TGCCACCACCTGTCAGCTCCTTTCCGGGACTTTCGCTTTCCCCCTCCCTA

TTGCCACGGCGGAACTCATCGCCGCCTGCCTTGCCCGCTGCTGGACAGGG

GCTCGGCTGTTGGGCACTGACAATTCCGTGGTGTTGTCGGGGAAATCATC

GTCCTTTCCTTGGCTGCTCGCCTGTGTTGCCACCTGGATTCTGCGCGGGA

CGTCCTTCTGCTACGTCCCTTCGGCCCTCAATCCAGCGGACCTTCCTTCC

CGCGGCCTGCTGCCGGCTCTGCGGCCTCTTCCGCGTCTTCGCCTTCGCCC

TCAGACGAGTCGGATCTCCCTTTGGGCCGCCTCCCCGC

The invention encompasses the use of any variant sequence of the WPRE which increases expression of the transgene compared to a vector without a WPRE. Preferably, variant sequences display at least 70% identity to SEQ ID NO: 6 over its entire sequence, more preferably 75%, 80%, 85%, 90% and more preferably at least 95%, 96% 97%, 98% or 99% identity to SEQ ID NO: 6 over its entire sequence.

Another regulatory sequence which may be used in a vector of the invention is a scaffold-attachment region (SAR). Additional regulatory sequences may be readily selected by the skilled person.

Method of Administration

In one embodiment of the invention, the viral (e.g. AAV) vector is administered to the eye of a subject by subretinal, direct retinal or intravitreal injection.

The skilled person will be familiar with and well able to carry out individual subretinal, direct retinal or intravitreal injections.

Preferably, the viral (e.g. AAV) vector is administered by subretinal injection.

Subretinal Injection

Subretinal injections are injections into the subretinal space, i.e. underneath the neurosensory retina. During a subretinal injection, the injected material is directed into, and creates a space between, the photoreceptor cell and retinal pigment epithelial (RPE) layers.

When the injection is carried out through a small retinotomy, a retinal detachment may be created. The detached, raised layer of the retina that is generated by the injected material is referred to as a "bleb".

The hole created by the subretinal injection must be sufficiently small that the injected solution does not significantly reflux back into the vitreous cavity after administration. Such reflux would be particularly problematic when a medicament is injected, because the effects of the medicament would be directed away from the target zone. Preferably, the injection creates a self-sealing entry point in the neurosensory retina, i.e. once the injection needle is removed, the hole created by the needle reseals such that very little or substantially no injected material is released through the hole.

To facilitate this process, specialist subretinal injection needles are commercially available (e.g. DORC 41G Teflon subretinal injection needle, Dutch Ophthalmic Research Center International BV, Zuidland, The Netherlands). These are needles designed to carry out subretinal injections.

Unless damage to the retina occurs during the injection, and as long as a sufficiently small needle is used, substantially all injected material remains localised between the detached neurosensory retina and the RPE at the site of the localised retinal detachment (i.e. does not reflux into the vitreous cavity). Indeed, the typical persistence of the bleb over a short time frame indicates that there is usually little escape of the injected material into the vitreous. The bleb may dissipate over a longer time frame as the injected material is absorbed.

Visualisations of the eye, in particular the retina, for example using optical coherence tomography, may be made pre-operatively.

Two-step Subretinal Injection

The vector of the invention may be delivered with increased accuracy and safety by using a two-step method in which a localised retinal detachment is created by the subretinal injection of a first solution. The first solution does not comprise the vector. A second subretinal injection is then used to deliver the medicament comprising the vector into the subretinal fluid of the bleb created by the first subretinal injection. Because the injection delivering the medicament is not being used to detach the retina, a specific volume of solution may be injected in this second step.

In one embodiment of the invention, the viral (e.g. AAV) vector is delivered by:
(a) administering a solution to the subject by subretinal injection in an amount effective to at least partially detach the retina to form a subretinal bleb, wherein the solution does not comprise the vector; and
(b) administering a medicament composition by subretinal injection into the bleb formed by step (a), wherein the medicament comprises the vector.

The volume of solution injected in step (a) to at least partially detach the retina may be, for example, about 10-1000 μL, for example about 50-1000, 100-1000, 250-1000, 500-1000, 10-500, 50-500, 100-500, 250-500 μL. The volume may be, for example, about 10, 50, 100, 200, 300, 400, 500, 600, 700, 800, 900 or 1000 μL.

The volume of the medicament composition injected in step (b) may be, for example, about 10-500 μL, for example about 50-500, 100-500, 200-500, 300-500, 400-500, 50-250, 100-250, 200-250 or 50-150 μL. The volume may be, for example, about 10, 50, 100, 150, 200, 250, 300, 350, 400, 450 or 500 μL. Preferably, the volume of the medicament composition injected in step (b) is 100 μL. Larger volumes may increase the risk of stretching the retina, while smaller volumes may be difficult to see.

The solution that does not comprise the medicament (i.e. the "first solution" of step (a)) may be similarly formulated to the solution that does comprise the medicament, as described below. A preferred solution that does not comprise the medicament is balanced saline solution (BSS) or a similar buffer solution matched to the pH and osmolality of the subretinal space.

Visualising the Retina During Surgery

Under certain circumstances, for example during end-stage retinal degenerations, identifying the retina is difficult because it is thin, transparent and difficult to see against the disrupted and heavily pigmented epithelium on which it sits. The use of a blue vital dye (e.g. Brilliant Peel®, Geuder; MembraneBlue-Dual®, Dorc) may facilitate the identification of the retinal hole made for the retinal detachment procedure (i.e. step (a) in the two-step subretinal injection method of the invention) so that the medicament can be administered through the same hole without the risk of reflux back into the vitreous cavity.

The use of the blue vital dye also identifies any regions of the retina where there is a thickened internal limiting membrane or epiretinal membrane, as injection through either of these structures would hinder clean access into the subretinal space. Furthermore, contraction of either of these structures in the immediate post-operative period could lead to stretching of the retinal entry hole, which could lead to reflux of the medicament into the vitreous cavity.

Pharmaceutical Compositions and Injected Solutions

The medicaments, for example vectors, of the invention may be formulated into pharmaceutical compositions. These compositions may comprise, in addition to the medicament, a pharmaceutically acceptable carrier, diluent, excipient, buffer, stabiliser or other materials well known in the art. Such materials should be non-toxic and should not interfere with the efficacy of the active ingredient. The precise nature of the carrier or other material may be determined by the skilled person according to the route of administration, e.g. subretinal, direct retinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution, or glycols such as ethylene glycol, propylene glycol or polyethylene glycol may be included. In some cases, a surfactant, such as pluronic acid (PF68) 0.001% may be used.

For injection at the site of affliction, the active ingredient may be in the form of an aqueous solution which is pyrogen-free, and has suitable pH, isotonicity and stability. The skilled person is well able to prepare suitable solutions using, for example, isotonic vehicles such as Sodium Chloride Injection, Ringer's Injection or Lactated Ringer's Injection. Preservatives, stabilisers, buffers, antioxidants and/or other additives may be included as required.

For delayed release, the medicament may be included in a pharmaceutical composition which is formulated for slow release, such as in microcapsules formed from biocompatible polymers or in liposomal carrier systems according to methods known in the art.

Method of Treatment

It is to be appreciated that all references herein to treatment include curative, palliative and prophylactic treatment; although in the context of the invention references to preventing are more commonly associated with prophylactic treatment. Treatment may also include arresting progression in the severity of a disease.

The treatment of mammals, particularly humans, is preferred. However, both human and veterinary treatments are within the scope of the invention.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85%, 90%, 99.1%, 99.2%, 99.3%, 99.4%, 99.5%, 99.6%, 99.7%, 99.8% or 99.9% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" of full length RPGR$^{ORF15}$ are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

All publications mentioned in the above specification are herein incorporated by reference. Various modifications and variations of the described products, systems, uses, processes and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

EXAMPLES

Example 1

Example 1A

Mouse Model Systems for X-linked Retinitis Pigmentosa

Figure 1:
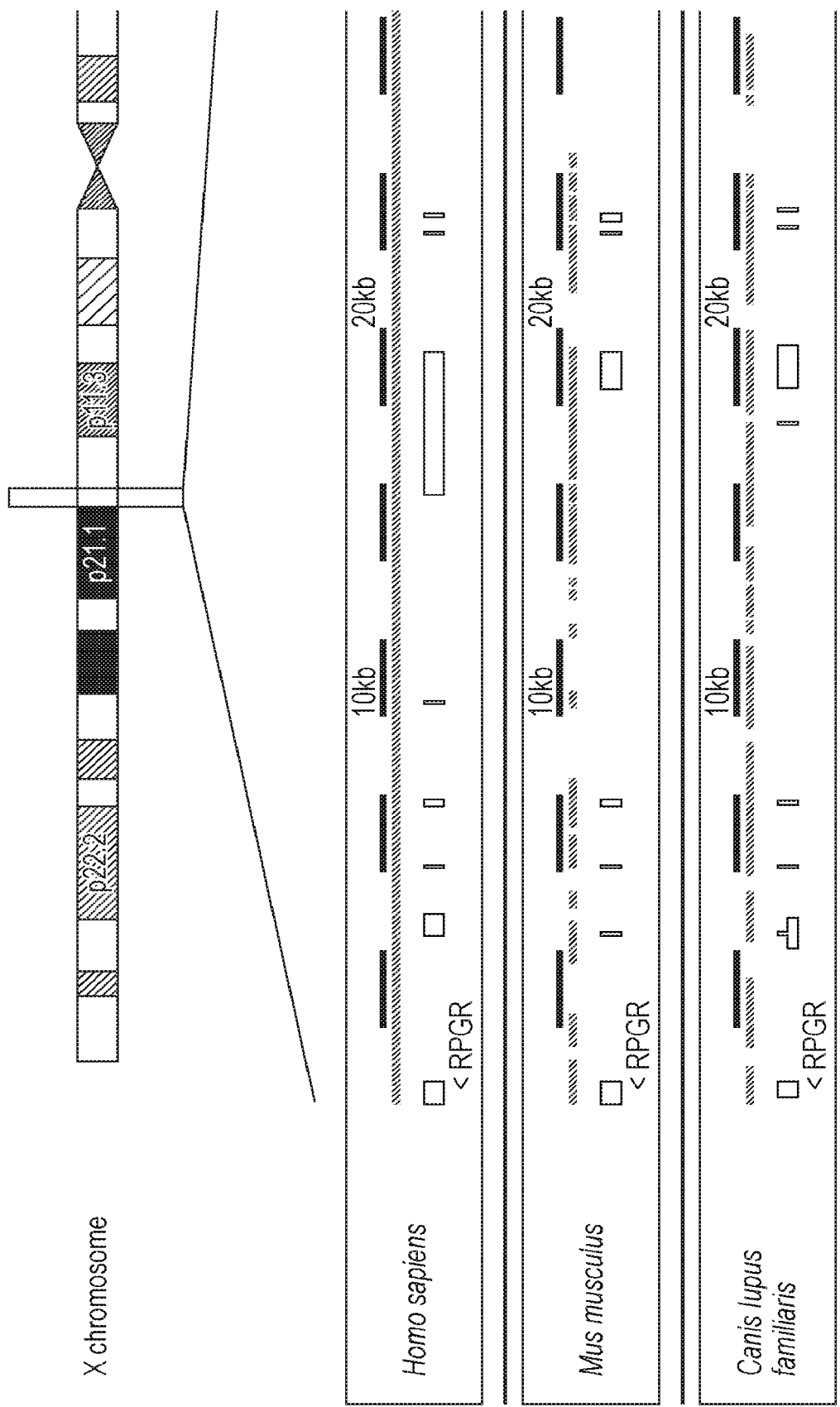
FIG. 1
Figure 1:
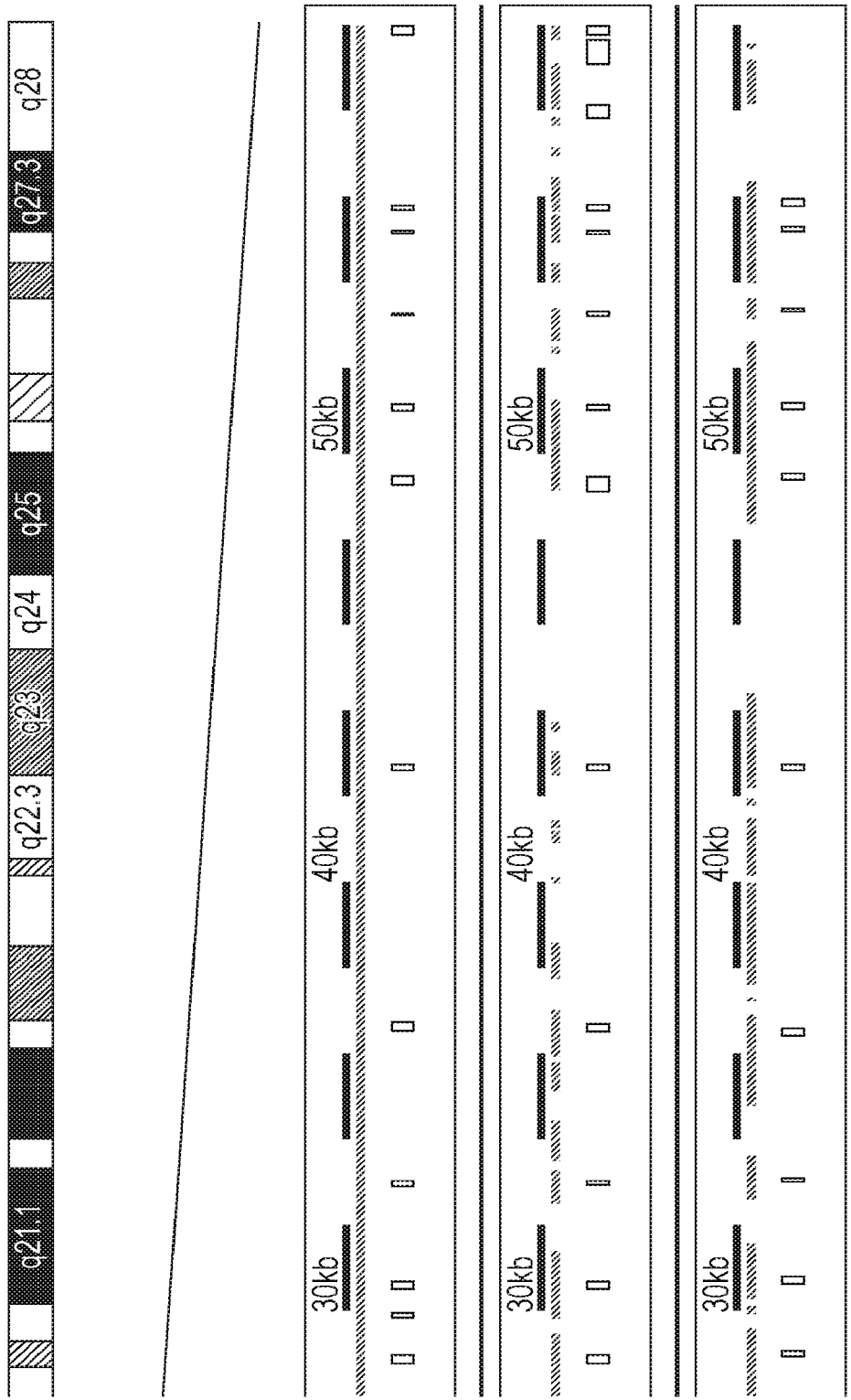

Certain species, for example mice and dogs, have genes that are homologous to human RPGR (compare the yellow exonic sequences shown in FIG. 1). Such species may therefore serve as potential models for X-linked retinitis pigmentosa caused by mutations in human RPGR.

Two mouse models were obtained to test the safety and efficacy of the therapeutic vector in this study. Both have alterations in the homologous gene Rpgr.
1. The Rpgr '1' strain: this strain was engineered by targeted disruption of parts of exon 4 though part of exon 6 by a sequence containing genes encoding β-galactosidase and a neomycin resistance marker (Hong D. H. et al. (2000) Proc. Natl. Acad. Sci. USA 97: 3649-3654).
2. The Rd9 strain: this strain features a naturally occurring insertional mutation of 32 bp which leads to a frame-shift (Thompson D. A. et al. (2012) PLoS One 7: e35865).

Both Rpgr$^{-/-}$ and Rd9 mouse models lack Rpgr protein expression, but only feature a very mild phenotype (Thompson D. A. et al. (2012) PLoS One 7: e35865).

Example 1B

Codon Optimisation of RPGR

RPGR Codon Optimisation

A synthetic RPGR$^{ORF15}$ sequence was prepared using codon optimisation (coRPGR, "Optimized"; SEQ ID NO: 3) to stabilise the highly mutagenic purine-rich region (FIG. 2).
Characterisation of the Codon Optimised RPGR Gene Cloning efficiency and sequence fidelity were compared between the wild type and codon optimised sequences in a standard cloning vector (FIG. 3A-D).

Figure 3:
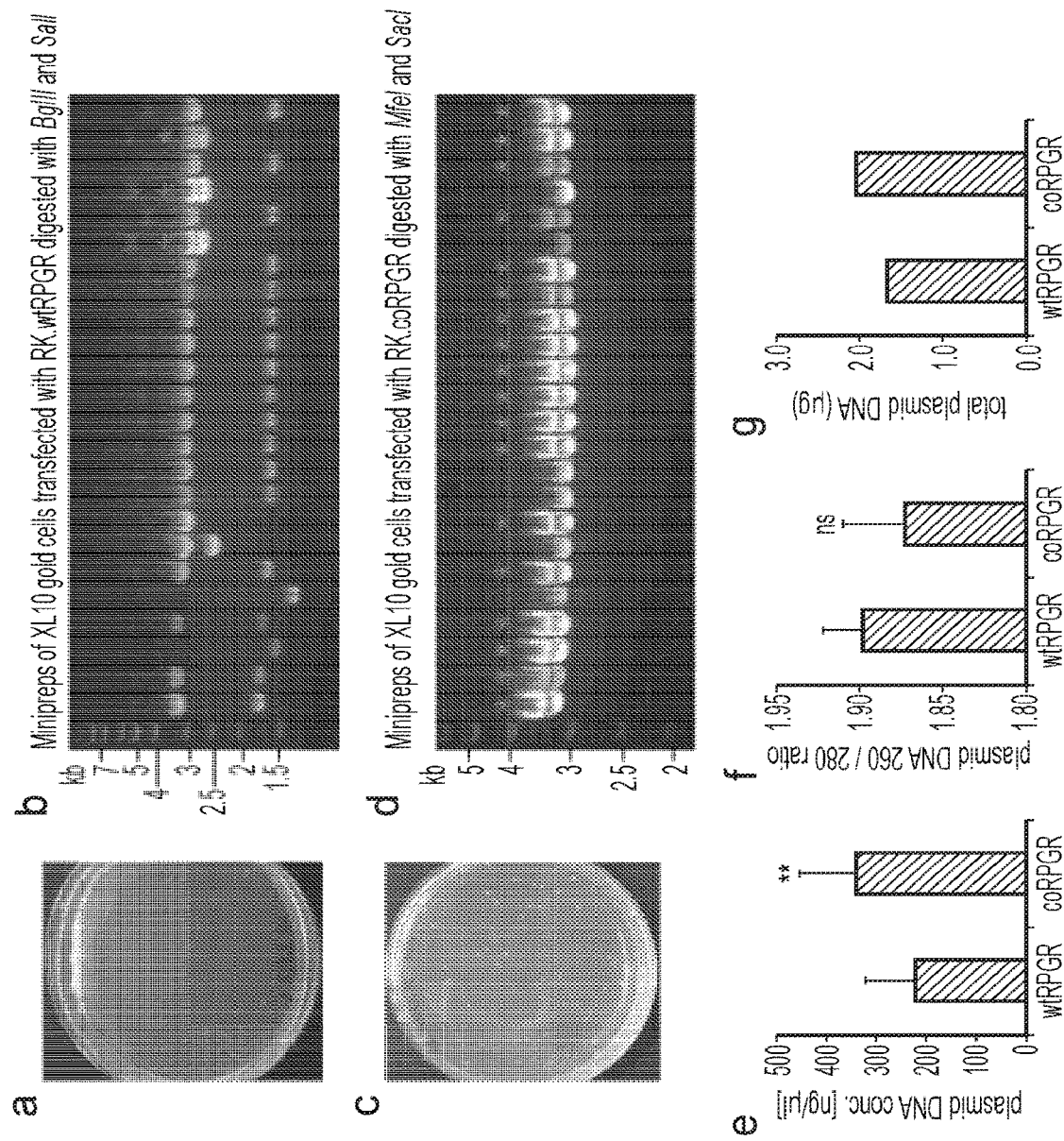

Using a restriction digest analysis, only 3 out of 24 clones were found to successfully feature the wild type sequence (wtRPGR; FIG. 3B, successful clones highlighted with asterisks). In contrast, 18 out of 24 clones successfully featured the correct codon optimised sequence (coRPGR; FIG. 3D).

Plasmid yields from minipreparations were found to be higher using the coRPGR sequence than the wtRPGR (FIG. 3E), even though a similar level of sample purity was maintained (FIG. 3F). In support of this finding, total plasmid yield from megapreparations (FIG. 3G) was also higher when using the coRPGR sequence.
Analysis of the Frequency of RPGR Mutations During Cloning Sanger-sequencing of the resulting clones was found to be easier and associated with a better overall signal-to-noise ratio when using the coRPGR sequence as ambiguous base calls were found to be less likely (FIG. 4).

Due to multiple G-runs and the purine-rich nature of wtRPGR, 34 individual sequencing reactions had to be performed to cover approximately 4 kb of DNA sequence. In the ORF15 region, 6 potential mutations (2 deletions and 4 insertions) were found, as well as 74 ambiguous base calls with the potential of further point mutations.

In contrast, coRPGR was easier to sequence and a clean confirmation (at least 2×) of its sequence was achieved with only 17 reactions.
Quantitative Analysis of Sequence Fidelity Four independently produced plasmid megapreparations of wtRPGR$^{ORF15}$ and coRPGR$^{ORF15}$ each were sequenced in an ISO 9001 certified, GLP accredited laboratory (Source Bioscience, UK) as a commercial contractor using Sanger sequencing, the gold standard for validating DNA sequences (Sanger F et al. (1977) Proc. Natl. Acad. Sci. USA 74: 5463-5467).

Alignment of the sequencing data with published reference data (NCBI Gene ID: 6103) revealed an average of 20 mutations (mostly single nucleotide deletions, insertions and point mutations) in the wtRPGR$^{ORF15}$ sequencing data, but none in coRPGR$^{ORF15}$.

|  | wtRPGR$^{ORF15}$ | coRPGR$^{ORF15}$ |
| --- | --- | --- |
| deletions mean [mean (range)] | 1.5 (0-4) | nil |
| insertions mean [mean (range)] | 0.5 (0-1) | nil |
| Point mutations [mean (range)] | 17.8 (9-33) | nil |
| Total mean [mean (range)] | 19.75 (9-36) | nil |

This analysis clearly demonstrates much greater sequence stability in the codon optimised RPGR sequence.

Analysis of the coRPGR Transgene Product Protein

Liquid chromatography with tandem mass spectrometry (LC/MS-MS) was performed to confirm the protein sequence of the coRPGR transgene product (FIG. 5).

Approximately 80% of the RPGR amino acids were directly identified. Only part of the highly glutamic acid-rich and repetitive region towards the C-terminus of the protein escaped the peptide analysis (FIG. 5, sequence in red). This was due to a lack of specific motifs to create oligomers for the spectrometry. However, the perfect match of the C-terminal sequence suggests the full length protein without any frame shifts was produced.

Figure 6:
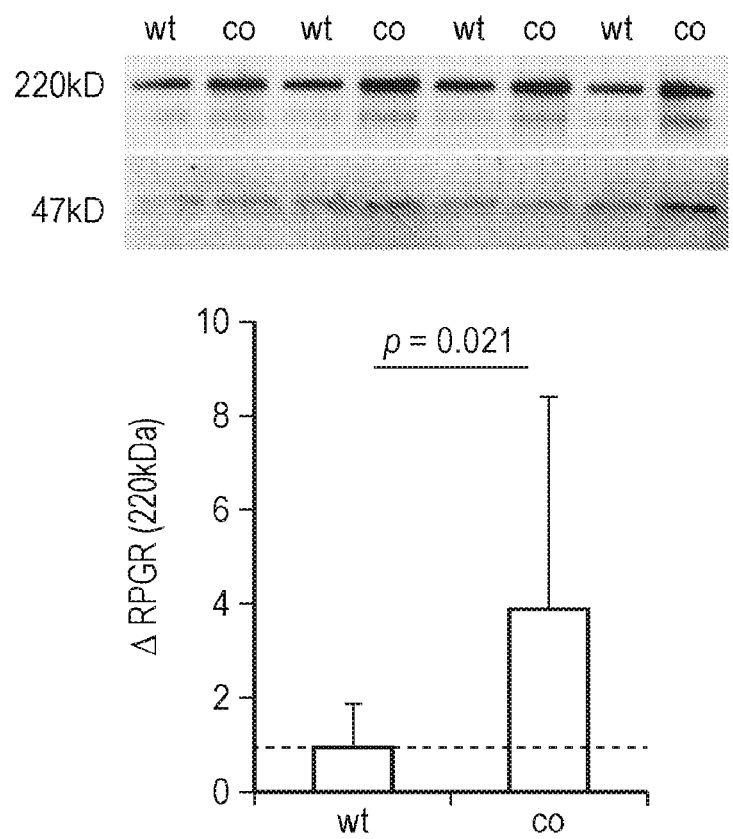

In addition, Western analysis indicated identical molecular masses of the wtRPGR and coRPGR-derived peptides from transfected cells (FIG. 6). This supports the conclusion that there are no differences (e.g. insertions or deletions) that have been introduced by the codon optimisation approach.

The Western analysis also clearly shows that codon optimisation enables higher rates of translation and protein production (FIG. 6).

Conclusion

Overall, the codon-optimised $RPGR^{ORF15}$ (coRPGR) sequence demonstrated superior sequence fidelity and increased expression levels compared to the wild type sequence and thus was considered likely to improve the therapeutic potential of XLRP gene replacement therapy.

Example 1C

AAV-Mediated In Vivo Delivery of Codon Optimised RPGR

The coRPGR sequence was packaged into an AAV2/8 vector, which was used to introduce RPGR into the photoreceptor cells of mice lacking RPGR expression (the Rd9 and Rpgr_/~mouse strains). In more detail, the transgene cassette featured a rhodopsin kinase promoter and Kozak consensus sequence upstream of the coRPGR polynucleotide sequence, and a polyA sequence from the bovine growth hormone downstream of the coding sequence.

coRPGR Leads to RPGR Protein Expression in Rd9 and $Rpgr^{-/-}$ Mice

Western blot analyses showed that treatment of Rd9 and $Rpgr^{-/-}$ mice with an AAV. coRPGR vector leads to RPGR protein expression (FIG. 7A). Furthermore, immunohistochemical staining for RPGR was performed on treated and untreated eyes from Rd9 and $Rpgr^{-/-}$ mice and demonstrated correct localisation of the protein product (FIG. 7B).

Gene Augmentation with coRPGR Leads to a Therapeutic Effect in Rd9 and $Rpgr^{-/-}$ Mice Both Rd9 and $Rpgr^{-/-}$ mouse models were subjected to gene therapy in one eye only and electroretinography (ERG) was used to objectively assess function in the treated versus untreated eyes.

Studies of a- and b-wave amplitudes of single flash intensity series after dark adaptation (FIG. 7C, FIG. 7D) show statistically significant amplitudes ($p<0.05$) in treated compared to untreated groups at two time points after treatment.

In conclusion, the above data, which is described in more detail in Examples 4 and 5, show that a codon optimised sequence of human RPGR produces wild type RPGR protein with the predicted size and amino acid sequence. Additionally, codon optimisation leads to higher sequence fidelity and expression levels. When applied by means of replacement gene therapy in models with an inherent lack of Rpgr protein expression, the coRPGR sequence provides for expression of RPGR. Moreover, the RPGR localises to the physiological site of action in the connecting cilium and is able to improve retinal structure (inner and outer segment length) and function as shown by ERG studies.

Example 2 pAAV.RK.coRPGR Plasmid Manufacture at Industrial Scale

Example 2a

Production of Bacterial Cell Bank for Plasmid Encoding Codon Optimised RPGR Sequence A K-12 *Escherichia coli* bacterial strain, XL10Gold, with the genotype Tet'D(mcrA)183 D(mcrCB-hsdSMR-mrr) 173 endA 1 supE44 thi-1 recA 1 gyrA96 relA1 lac Hte [F' proAB lacI$^q$ZDM15 Tn10 (Tet$^r$) Amy Cam$^r$] was transformed with the plasmid pAAV.RK.coRPGR and plated out on agar plates supplemented with ampicillin to select single colonies containing the plasmid DNA with the codon optimised RPGR sequence. A single colony was selected, inoculated into culture medium and expanded in small scale liquid culture. Once the cells were in mid log growth phase they were harvested and resuspended in cryopreservation media containing glycerol before approximately fifty 1.5 mL aliquots were dispensed into 1.8 mL cryovials and frozen at −80° C. to produce the bacterial cell bank, RCB pAAV.RK.coRPGR *E. coli* XL10Gold.

Figure 8:
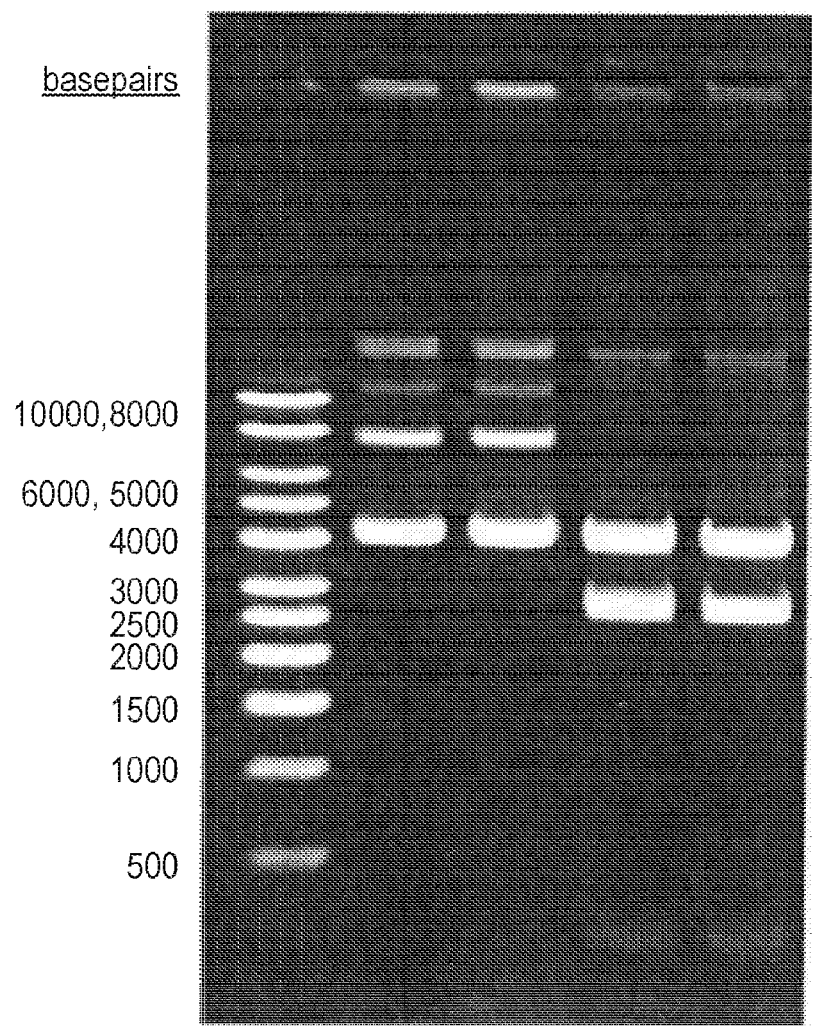
Figure 9:
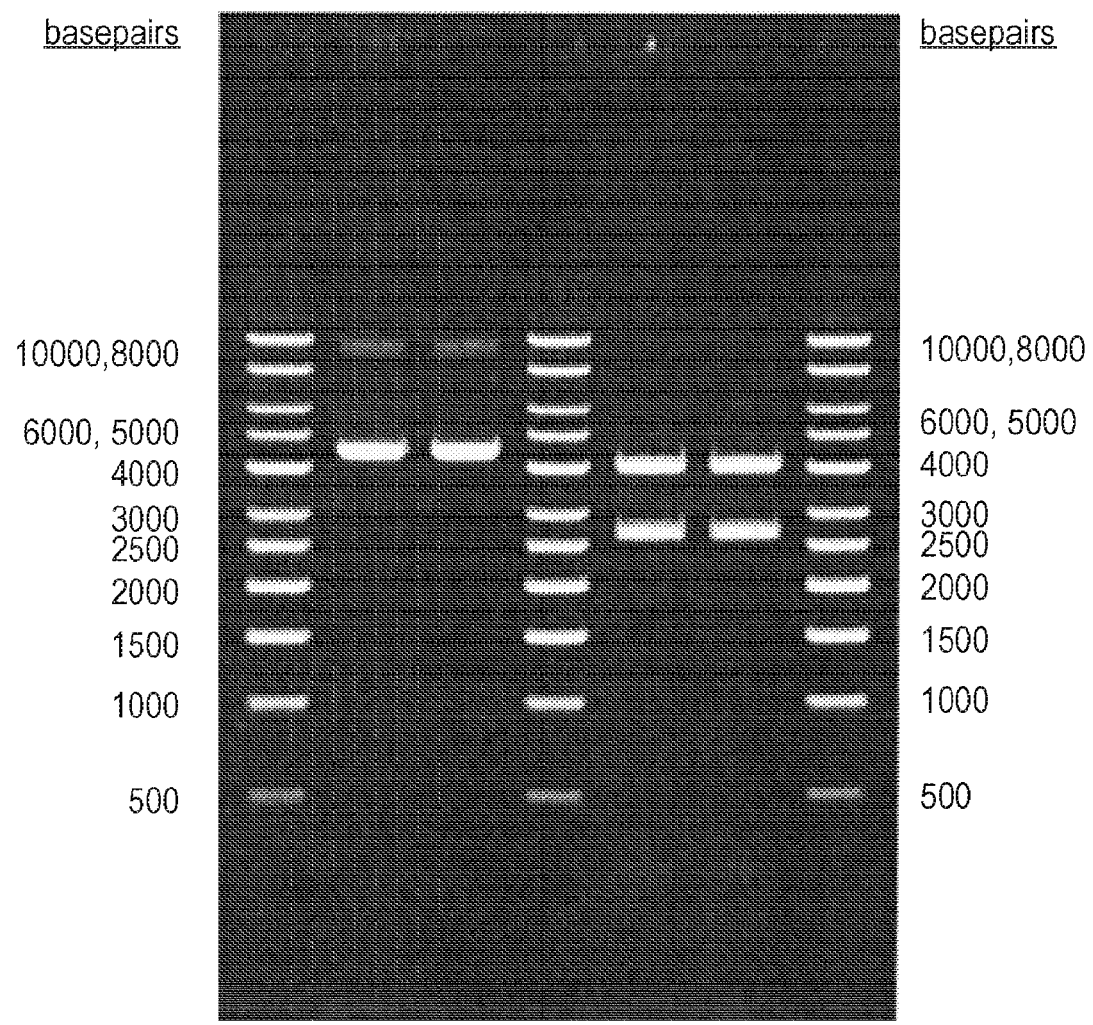

The cell bank was thawed and plasmid DNA prepared by a miniprep extraction (Birnboim H. C. and Doly J. 1979; A rapid alkaline extraction procedure for screening recombinant plasmid DNA in 1979 Nov. 24; 7(6):1513-23) and tested for plasmid identity and structural stability by XmnI and SmaI endonuclease restriction digest and subsequent analysis by 0.8% agarose gel electrophoresis and 0.5 mg/mL ethidium bromide staining (FIG. 8). FIG. 8 clearly shows the expected restriction digest fragment pattern from a stable and structurally intact pAAV.RK.coRPGR plasmid, demonstrating stable maintenance and reproduction of the plasmid DNA during cell bank culture expansion and production.

The cell bank was also assessed for plasmid yield following broth culture in shake flasks and produced 598 µg of plasmid DNA per gram of wet cell mass. A high plasmid yield of the correct plasmid was obtained.

There was also no evidence of plasmid loss when segregational stability was tested by replica plating of colonies onto antibiotic-containing and antibiotic-free agar plates. Results showed 100% plasmid retention.

Plasmid DNA from the cell bank was sequenced using Sanger (Sanger F et al. (1977) Proc. Natl. Acad. Sci. USA 74: 5463-5467) sequencing, the resultant sequence analysis showed that the codon optimised RPGR sequence was retained with 100% fidelity when compared to the theoretical reference sequence of the codon optimised RPGR sequence. Again there was no evidence of instability.

RCB pAAV.RK.coRPGR *E. coli* XL10Gold was also tested for bacterial purity (absence of bacterial contamination was demonstrated) and for the absence of lytic and lysogenic bacteriophages (none detected). The species identity of RCB pAAV.RK.coRPGR *E. coli* XL10Gold was also confirmed by biochemical identification using the API-20E test (BioMerieux).

Conclusion

Codon optimisation of the RPGR gene has led to an improvement in the stability of the RPGR gene resulting in the ability to generate an industrially useful bacterial cell bank which showed 100% sequence fidelity with the reference codon optimised sequence, 100% plasmid segregational stability and good plasmid yield.

Example 2b

Production of High Quality Plasmid Encoding Codon Optimised RPGR Sequence at Industrial Scale High Quality plasmid DNA was manufactured and purified (Schmeer et al. (2014) Pharmaceutical Grade Large-Scale Plasmid DNA Manufacturing Process: 219-242), from the E. coli XL10Gold bacterial cell bank RCB pAAV.RK.coRPGR generated in example 2a as briefly described. A single vial of the bacterial cell bank was thawed and expanded and cultured at an industrial scale, the bacterial cell mass was then harvested by centrifugation. The plasmid DNA was extracted from the bacterial biomass by alkaline bacterial cell lysis, the resultant soluble plasmid DNA was separated from insoluble protein and complexed genomic DNA by centrifugation and filtration. The plasmid DNA was further purified by a multi-step chromatography process. The fully purified plasmid DNA was finally formulated in formulation buffer by precipitation and tangential flow filtration and membrane filtration to generate 100 mg of highly purified plasmid DNA at 1.0 mg/mL in 10 mM Tris+1 mM EDTA, pH8.0 (FIG. 10) and was of sufficient purity (FIG. 11) for use in further manufacturing processes for the production of rAAV vectors.

Figure 11:
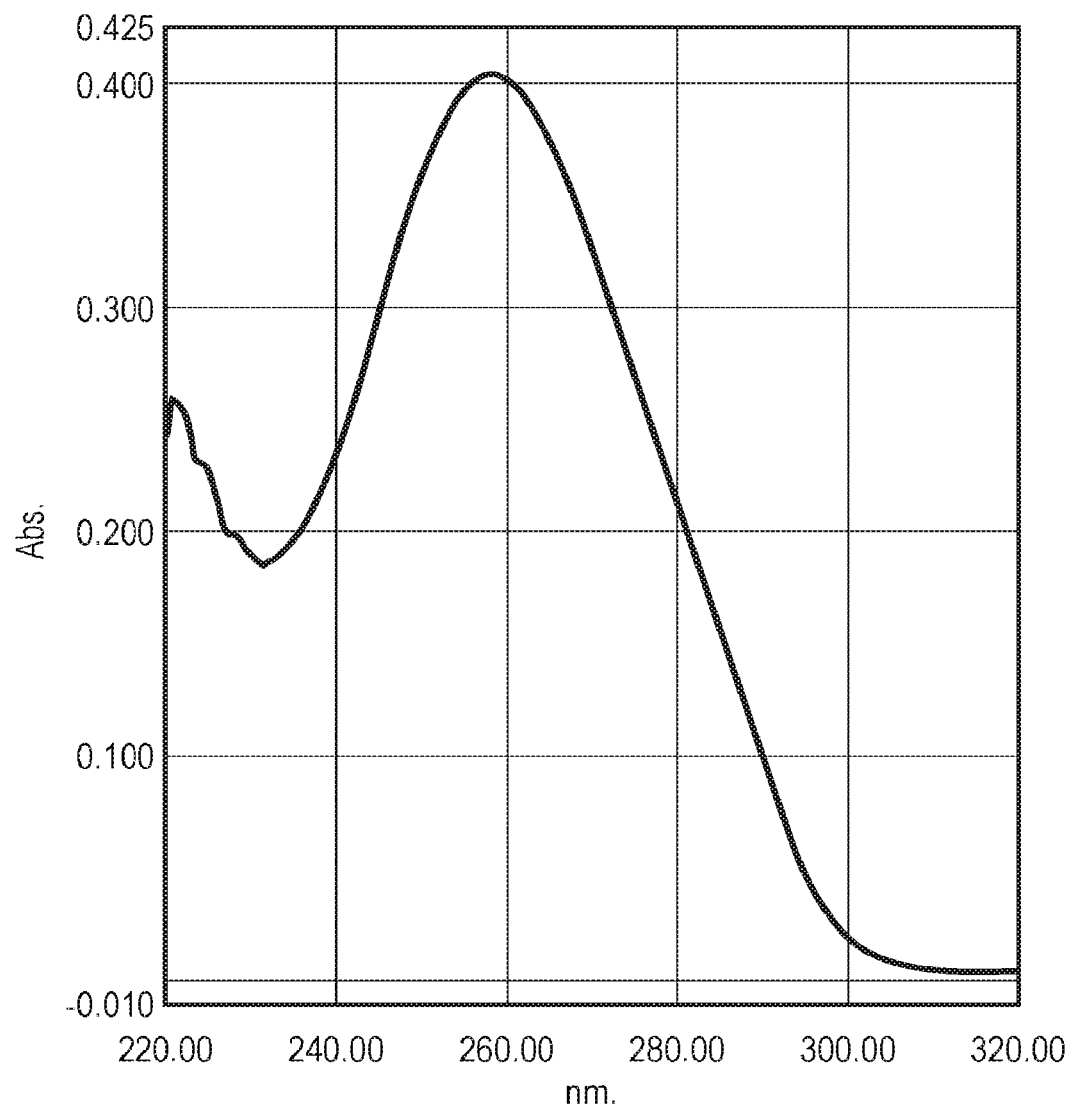

The purified plasmid was tested for plasmid identity and structural stability by XmnI endonuclease restriction digest and subsequent analysis by 0.8% agarose gel electrophoresis and 0.5 mg/mL ethidium bromide staining (FIG. 10). FIG. 11 clearly shows the expected restriction digest fragment pattern from a stable and structurally intact pAAV.RK.coRPGR plasmid, demonstrating stable maintenance and reproduction of the plasmid DNA during cell culture expansion and plasmid purification.

The purified plasmid was sequenced using Sanger sequencing (Sanger F et al. (1977) Proc. Natl. Acad. Sci. USA 74: 5463-5467), the resultant sequence analysis showed that the codon optimised RPGR sequence was retained with 100% fidelity when compared to the theoretical reference sequence of the codon optimised RPGR sequence.

Conclusion

Codon optimisation of the RPGR gene has led to an improvement in the stability of the RPGR gene resulting in the ability to generate high purity plasmid DNA in sufficient quantity (100 mg) and quality for further manufacturing processes for the production of rAAV vector Example 2c Production of rAAV2/8 Encoding Codon Optimised RPGR Sequence at Industrial Scale High Quality plasmid DNA manufactured in example 2b was used alongside helper plasmid pDP8.ape (PlasmidFactory, Bielefeld, Germany and Grimm D, Kay M A, Kleinschmidt J A. Helper virus-free, optically controllable, and two-plasmid-based production of adeno-associated virus vectors of serotypes 1 to 6. Mol Ther 2003; 7:839-850) to manufacture rAAV8/2 vector for use in-vivo use by large scale transient transfection and subsequent purification (Lock et al. 2010; Human Gene Therapy: 1259-1271). Briefly, HEK293 cells were grown in adherent culture in Dulbecco's modified Eagles media (DMEM) supplemented with 10% foetal bovine serum (FBS) at 37° C. and 5% $CO_2$, until sufficient cells were available to seed sufficient multi layered cell culture vessels. Unpurified AAV was produced by calcium phosphate transient transfection of the HEK293 cells growing adherently within multi-layered cell culture vessels using the pAAV.RK.coRPGR plasmid and pDP8.ape helper plasmid to produce rAAV particles secreted into the growth media. The rAAV particles were harvested by removal of the media from the cell culture vessels and filtered to remove cellular debris. rAAV was initially concentrated by tangential flow filtration (TFF) and ultrafiltration and partially purified by diafiltration using the same TFF equipment. The rAAV was further purified using iodixanol discontinuous gradient ultracentrifugation and column ion exchange chromatography. The purified rAAV was then formulated into the final formulation buffer at a concentration of $3.55 \times 10^{12}$ gp/ml by further TFF based ultrafiltration and diafiltration. A second lower rAAV concentration formulation of $1.00 \times 10^{12}$ gp/ml was manufactured by dilution of the higher dosage form into formulation buffer. Both dosage forms were vialled in 50 μL aliquots and stored at ≤60° C.

Conclusion

Codon optimisation of the RPGR gene has led to an improvement in the stability of the RPGR gene resulting in the ability to generate purified rAAV vector in sufficient quantity and quality for use in in-vivo dosing studies.

Example 2d

The aim of the studies was to establish in vivo delivery of the AAV8-RPGR gene therapy vector administered via sub-retinal dosing, the preferred clinical route of administration (ROA). The work was conducted with AAV8-RPGR in a GLP-compliant, sub-retinal injection, single-dose study in C57B/6J mice followed by analysis at 4-week and 26-week periods.

The C57B/6J pigmented mouse strain was selected as a relevant species for these in vivo delivery studies for the following reasons. Firstly, this strain has pigmented eyes allowing very close mimicking of the administration procedure applied in the clinical setting. Secondly, a transgenic variant of this strain, a RPGR knockout mouse model, demonstrated a biological response to the investigational AAV8-RPGR product similar to that expected in humans. Thirdly, the human and the mouse RPGR protein share a high amino acid sequence homology and successful AAV8-RPGR targeting and transduction of mouse retinal tissue has previously been demonstrated in the in vivo pharmacology studies.

Animals received a single sub-retinal 1 μL injection of vehicle (BSS Plus, Alcon Pharma) or AAV8-RPGR (at two different gp/eye dosages) in both eyes. Extensive evaluations of any toxic effects including the assessment of body weights, clinical signs of toxicity, including food consumption, clinical pathology and histopathology were performed as well as detailed and regular ophthalmic examinations of the eye globe, external ocular structures, the anterior segment of the eye, mainly of the cornea and lens and internal structures including the ocular fundus. Furthermore regular tonometric evaluations and electroretinography assessments were conducted. Electroretinography (ERG) records electric potentials that arise in the retina after light stimulation at different light intensities, wave lengths, and exposure duration. The electroretinogram represents the composite activity of millions of retinal cells, extending from the pigment epithelium to the inner nuclear layer. It was used as an assessment of retinal function and detection of early stages of the retinal degeneration.

The AAV8-RPGR gene therapy was well tolerated in the mice and no serious adverse reactions to the treatment were observed. Any observations were transient and consistent with the dosing and anaesthetic procedures that were also reported in the vehicle treated groups.

To understand the distribution of the delivered AAV8-RPGR vector, treated animal groups were divided into subgroups that were sacrificed on Days 8, 29 and 183 after injection. Additional, non-terminal blood samples were collected on Days 2, 15 and 92 in each of the subgroups for the determination of vector levels by an AAV8-RPGR specific quantitative PCR assay (qPCR). Animals received a single sub-retinal 1 µL injection of vehicle (BSS Plus, Alcon Pharma) or AAV8-RPGR in both eyes.

qPCR samples from several tissues/body fluids (blood, bone marrow, lacrimal fluid, brain, eye, heart, aqueous and vitreous humour, kidney, liver, lung, lymph node, optic nerve, retina, saliva, testis, spleen, urine) taken from the animals at necropsy on Days 8, 29 and 183 will be assayed for vector DNA quantification. Vector DNA quantification in these tissues/fluids will be performed via a qPCR method at the end of the study. These results will confirm the successful delivery of the gene therapy and map its distribution through the mice tissues.

Example 3

In Vitro Analysis of the coRPGR$^{ORF15}$ Transgene Product Protein

In this example, the effect of codon optimisation on the increase of RPGR expression levels and the improvement of splicing alternative forms synthesis was analysed. For this purpose, human embryonic kidney 293 cells (HEK293) and HEK293 expressing the simian virus 40 (SV40) T antigen (HEK293T) cells were used. These cells were transfected with CAG.coRPGR$^{ORF15}$ and CAG.wtRPGR$^{ORF15}$ plasmid constructs and processed for transgene detection as described below.

Material and Methods

HEK293 and HEK293T cells were seeded at 4 and $2.5 \times 10^5$ cells/ml, respectively, in 6-well plates and cultured in DMEM supplemented with 10% heat inactivated foetal bovine serum (FBS) and 1% penicillin/streptomycin at 37° C. and 5% $CO_2$ until they were over 70% confluent. One microgram of plasmid DNA (CAG.coRPGR$^{ORF15}$ and CAG.wtRPGR$^{ORF15}$) was delivered to the cells using the Mirus TransIT®-LT1 Transfection Reagent (Geneflow Ltd., Lichfield, UK) and serum/antibiotic free medium. Transfected cells were incubated at 37° C. for 48 hours.

Analysis of transgene expression was conducted at protein level. Forty-eight hours after transfection, cells were washed in phosphate-buffered saline (PBS) before proceeding with cell lysis and protein solubilisation with Radio-Immunoprecipitation Assay (RIPA) buffer (Sigma-Aldrich Company Ltd., Dorset, UK) with complete mini EDTA-free protease inhibitor cocktail tablet (Roche Products Ltd., Welwyn Garden City, UK). Cell pellets were disrupted by sonication using ultrasonic frequencies and cell fragments were removed by centrifugation at 13,000 g and 4° C. for 10 minutes. Total protein content was quantified in the supernatant using the Pierce™ bicinchoninic acid (BCA) Protein Assay Kit (Thermo Scientific) according to the manufacturer's instructions.

Protein expression was assessed by Western blot analysis. Thirty µg of total protein was denatured in 2×Laemmli buffer (Sigma-Aldrich) for 5 minutes at 95° C. and separated on a 7.5% sodium dodecyl sulfate polyacrylamide gels (Criterion™ TGX™ Precast Gels, Bio-Rad Laboratories Ltd., Hemel Hempstead, UK) for electrophoresis at 100 V for 2 hours. Protein samples separated in the SDS-PAGE were transferred onto polyvinylidene difluoride (PVDF) membranes (Trans-Blot Turbo™ Midi PVDF, Bio-Rad) using the Trans-Blot Turbo™ Transfer Starter System (Bio-Rad). The membranes were blocked with 3% bovine serum albumin (BSA) in PBS containing 0.1% Tween 20 for 45 minutes, and incubated with primary antibody at room temperature for 1 hour. RPGR, as target protein, and β-actin as loading control were identified with the following primary antibodies: rabbit polyclonal RPGR (1:500, Sigma-Aldrich) and mouse monoclonal β-actin (1:30000, Ambion Inc., Thermo Scientific, Nortumberland, UK). Bands were detected with horseradish peroxide conjugated secondary antibodies with the use of ECL detection reagent. RPGR protein levels were quantified by densitometry using Image Studio Lite (version 5.2) and normalised to β-actin.

Results

Western blot analysis on whole protein lysates showed a predominant band around 220 kDa, corresponding to RPGR$^{ORF15}$ protein (FIGS. 12A and 13A) in HEK293 and HEK293T cells transfected with CAG.coRPGR$^{ORF15}$ and CAG.wtRPGR$^{ORF15}$ plasmids. The quantitation of RPGR$^{ORF15}$ band intensity, normalised by the intensity of β-actin, revealed that the expression of RPGR is higher in HEK293 cells transfected with the codon optimised plasmid, 2.79 [1.1 to 17.0] arbitrary units (AU) (median [Q1 to Q3]) than in cells transfected with the wild type sequence, 0.36 [0.08 to 4.88] AU. Similarly, HEK293T cells transfected with the codon optimised sequence showed increased RPGR expression levels, 4.23±0.11 AU (mean±standard deviation) in comparison with the cells transfected with the wild type sequence, 3.01±0.07 AU (mean±standard deviation) (FIGS. 12B and 13B).

Besides the expression of the whole RPGR$^{ORF15}$ sequence with both plasmid constructs, an additional clear band of 80 kDa molecular weight was detected in HEK293 T cells transfected with the wild type RPGR$^{ORF15}$ sequence. This result showed that codon optimisation improves the sequence stability, thus reducing alternative spliced forms.

Conclusion

These results confirm that the increase of the codon adaptation index (CAI) of RPGR$^{ORF15}$ coding sequence through introducing synonymous major codons leads to higher transgene expression levels, while reducing the synthesis of truncated proteins by increasing the stability and the fidelity of the sequence.

Example 4

RPGR gene therapy aims to reconstitute RPGR expression in target cells, which harbour a disease causing mutation in RPGR leading to a complete loss of RPGR (null mutations) or a dysfunctional protein. One way of achieving this is by introducing a correct copy of RPGR-encoding nucleotide sequence, which is then translated to RPGR protein by the target cell's own translational machinery. Such a nucleotide sequence can be introduced by means of transduction with a recombinant AAV.

Here we present data from a pilot trial designed to explore the transduction efficiency of recombinant AAV vectors AAV2/8.RK.coRPGR and AAV2/8.RK.wtRPGR after subretinal injection in mice. To model RPGR gene therapy more closely to the clinical scenario, we used Rpgr−/y mice, which lack Rpgr expression.

Rpgr is the murine homologue of RPGR, the gene affected in most cases of X-linked retinitis pigmentosa and transgenic Rpgr−/y mice thus mimic null mutations in human patients on a genetic level. Codon optimised RPGR features higher expression levels then wild type RPGR and crucially provides greater sequence fidelity while leading to the identical RPGR protein product. Recombinant AAV vectors AAV2/8.RK.coRPGR and AAV2/8.RK.wtRPGR are able to transduce photoreceptor like cells in vitro.

The aim of this study was to explore whether RPGR would be expressed in vivo following subretinal injection of AAV2/8.RK.coRPGR or AAV2/8.RK.wtRPGR and whether RPGR would be localised to the connecting cilium in photoreceptor cells lacking inherent Rpgr expression.

Materials and Methods

Recombinant AAV solutions containing AAV2/8.RK.coRPGR and AAV2/8.RK.wtRPGR were produced and assessed for quality and titer. To control for the surgical intervention and photoreceptor transduction by AAV2/8, a third construct was used with GFP as reporter gene under control of the CAG promoter (AAV2/8.CAG.GFP). These vector solutions were quantified by qPCR to calculate the number of vector genomes/ml. Aliquots stored at −80° C. were thawed on ice immediately before application and diluted in balanced salt solution (BSS®) for vitreoretinal surgery (Alcon Laboratories, Camberley, UK) with 0.001% Pluronic® PF68 (BASF, Ludwigshafen, Germany) to allow subretinal delivery of 1×1010 vg in 20 µl volume.

Rpgr−/y mice were used for this pilot study as they lack Rpgr expression while maintaining a connecting cilium for the potential localisation of the transgene product RPGR. Mice were anaesthetised for subretinal injection of 20 AAV solution under the superior hemiretina.

Three weeks following the surgery, treated Rpgr−/y mice were again anaesthetised for in vivo retinal imaging using confocal scanning laser ophthalmoscopy (cSLO) to investigate autofluorescence pattern in the animals, which had received AAV2/8.RK.coRPGR, AAV2/8.RK.wtRPGR, and GFP fluorescence as readout of transduction efficiency in the animals treated with AAV2/8.CAG.eGFP.

Immediately after imaging, mice were sacrificed and quickly enucleated. Whole eyes were rapidly processed for immunohistochemistry without fixation. Briefly, 16µm sections of unfixed retinal samples were stained with Hoechst 33342 dye and a polyclonal antibody directed against amino acids 379-509 of RPGR (Sigma, HPA001593). Donkey anti-rabbit with conjugated AlexaFluor 488 (Invitrogen) was used as secondary antibody to indicated RPGR detection. High powered (×63 with oil immersion) optical sections were recorded on a confocal microscope (Zeiss LSM710) to investigate RPGR expression and localisation in photoreceptor cells of treated Rpgr−/y mice. Untreated mice served as negative control to test the specificity of the assay.

Surgical Outcome

All animals received the intended dose of AAV solution in the subretinal space and recovered well from anaesthesia. This was made possible by the surgical procedure, which first reduces the intraocular pressure (TOP) by an anterior paracentesis before creating a hemiretinal detachment with the vector suspension. This technique allowed delivery of up to 20 µl volume without developing corneal edema and/or limiting the intraocular circulation due to high IOP. At the same time, the lowered TOP reduced the risk of reflux of subretinal fluid through the injection canal (i.e. into the choroidal circulation or orbit).

Fundoscopic evaluation of treated mice 24 h after the surgery showed complete reattached retinae in all cases. Retinal imaging shows safe delivery and reporter gene expression. After three weeks, cSLO imaging revealed good optical media with clear view of the fundus in infrared imaging. Autofluorescence imaging showed hyperfluorescent dots in treated and untreated eyes of Rpgr−/y mice treated with AAV2/8.RK.coRPGR or AAV2/8.RK.wtRPGR. Mice with AAV2/8.CAG.GFP vector application demonstrated strong and ubiquitous GFP derived fluorescence. This indicated robust transgene expression and made it likely that the other recombinant AAV vectors would have had enough time to lead to transgene expression.

Confocal scanning laser ophthalmoscopy in (un-)treated Rpgr−/y mice was done. Infrared recordings with focal plane on the inner retina were done. Recordings in the autofluorescence mode were made. Untreated and mice treated with AAV.RK.wtRPGR or AAV.RK.coRPGR all showed a punctuate pattern of hyperfluorescence. At the same sensitivity setting, the eye treated with AAV.CAG.GFP demonstrated widespread and strong GFP fluorescence beyond the superior hemiretinal detachment indicating successful transduction of cells beyond the site of subretinal vector delivery.

Immunohistochemistry Shows RPGR Expression

Specific signal were observed in sections from treated but not in those from untreated mice. This signal stems from antibody binding to the RPGR epitope and is consistent with RPGR expression due to transduction with an AAV carrying RPGR as transgene. The more robust signal was seen in sections from eyes treated with AAV2/8.RK.coRPGR, the AAV carrying the codon optimised coRPGR.

Immunohistochemistry showed RPGR in treated Rpgr−/y mice. Untreated eye of an Rpgr−/y animal showed absence of RPGR staining. Single treatment with AAV.RK.wtRPGR results in detected signal, most of which was localised to the region between inner and outer segments. Rpgr−/y mice treated with codon optimised vector showed the most RPGR expression with the typical comma-type staining pattern of a connecting cilium marker.

Discussion

The surgical technique applied here allowed safe application of up to 2 µl into the subretinal space of mice. The resulting hemiretinal detachment spontaneously reattached within 24 h in all animals and no ocular sequelae were observed. At the same time it prevented (temporary) corneal oedema formation and/or cessation of intraocular circulation as can be observed after subretinal injections without prior paracentesis. Optical media remained clear for the following 3 weeks and there was no indication of intraocular pathology such as cellular infiltrates, anterior/posterior synechiae of the iris or cataract formation. Retinal imaging demonstrated robust levels of GFP transgene expression in the control group, which had received AAV2/8.CAG.GFP. Interestingly, the reporter protein GFP was evident across the whole retina, even though the immediate application was limited to the superior hemiretina. This indicates at least some degree of transduction of cells outside the detachment area. GFP expression was driven by the unspecific CAG promoter, which leads to ubiquitous transgene expression not limited to photoreceptors. This is in contrast to the vectors carrying the coRPGR of the present invention, in which the rhodopsin kinase promoter drives photoreceptor specific expression of coRPGR.

Eyes treated with AAV2/8.RK.coRPGR or AAV2/8.RK.wtRPGR showed normal retinal vasculature and nerve fibre layer as indicated by the infrared images focused on the inner retina. In contrast, mice treated with AAV2/8.CAG.eGFP vector demonstrated strong and ubiquitous GFP derived fluorescence. Unfixed sections showed RPGR expression and localisation to the connecting cilium in Rpgr−/y mice.

This is the first evidence for a successful delivery of a codon optimised RPGR vector sequence via AAV as a gene therapy in a RP animal model. In contrast to previous studies wherein mutations during the development of the vector used for transgene expression caused alternative protein products, this work demonstrates expression and correct localisation of RPGR based on a codon optimised sequence, which translates into a wild type RPGR protein product.

Example 5

Safety and Efficacy of coRPGR Gene Therapy

Developing gene therapy for XLRP has remained a challenge for a number of reasons. One is the purine rich, repetitive sequence of RPGRORF15, which makes it difficult to clone without encountering spontaneous mutations. Confirming the integrity of the sequence by Sanger sequencing is also problematic as the frequent poly-guanine runs cause DNA polymerases to stall or stop.

A second problem is the mild phenotype in murine disease models such as Rpgr/y and C57BL/6JRd9/Boc mice. With relatively small structural and functional differences between these disease models and wild type controls, it is difficult to reach a statistical significance level in a treatment cohort.

To address the first point, we applied the principle of codon optimisation to change the primary nucleotide sequence of the RPGRORF15 coding sequence. Because only synonymous codons were used, the resulting amino acid sequence remained unchanged while the codon optimised RPGR construct featured superior sequence stability and translational efficiency compared to the wild type RPGR construct. This benefit was evident in vitro when using plasmid transfections and transduction experiments with AAV constructs. The same AAV constructs were then used in a pilot trial to demonstrate their potential to transduce photoreceptors (Example 4). Resulting RPGR protein was localised to the connecting cilium, its physiological compartment in photoreceptors.

To address the second issue with small differences between cohorts with and without disruptive Rpgr mutations, we performed a sample size and power calculation based on relevant, objective and quantitative outcome measures.

The aim of this work was to test the efficacy of AAV.RK-.coRPGR as gene therapeutic agent for XLRP3 in two relevant animal models (Rpgr−/y and C57BL/6JRd9/Boc mice) and to explore any potential toxic effects in wild type animals (C57BL/6J). The study design was chosen to provide robust statistical evidence with the potential to serve as a basis for regulatory approval of a clinical phase I trial.
Materials and Methods
Sample Size and Power Calculations Sample size and power calculations were performed using a JavaScript based algorithm provided by Rollin Brant from the University of California, San Francisco Department of Epidemiology & Biostatistics, Division of Biostatistics. Primary outcome measure used for this was the a-wave amplitude [μV] after a dark-adapted single flash stimulus at 0.01 cd·s/m2, which reflects the physiology of the vast majority of photoreceptors in the mouse retina, the target cell population in this study. These electroretinographic (ERG) responses were measured and mean and standard deviations for n=4 per cohort (C57BL/6J, C57BL/6JRd9/Boc, and Rpgr−/y mice) calculated in Excel. Before calculating the sample size, difference of mean a-wave amplitude between C57BL/6J (target normal value) and C57BL/6JRd9/Boc (baseline before treatment) and between C57BL/6J and Rpgr−/y was calculated and ½ of this added to the current mean of the respective disease models assuming a 50% gain due to treatment. This provided values for μ0 (mean of untreated cohort) and μl (mean of treated cohort). Value for a (standard deviation of the sampled population) was set to the standard deviation of the a-wave amplitude in the respective disease model. A one-sided test design was assumed, the type I error rate set to α=0.05 and the desired power defined as 90% for the sample size calculation.

A comparable sample size was then used to calculate the power to detect toxic effects in C57BL/6J mice. For this, a loss of 10% of the mean a-wave amplitude at baseline was assumed as toxic effect and the baseline standard deviation entered as a.
Trial Design ERG responses were chosen as primary outcome measure as objective and quantitative biomarker of retinal function that is relevant to the disease process and an appropriate readout for potential therapeutic and/or toxic effect of the test item, AAV.RK.coRPGR. Due to relatively high inter-individual variability within cohorts, a intra-individual testing paradigm was chosen: one eye would be treated with AAV.RK.coRPGR (verum) while the contralateral eye would serve as control. In order to capture the natural disease process and have a control injection with an inactive substance (AAV. control) in such a design, two parallel trials were run: one (necessarily) open label trial with unilateral treatment of randomised eyes with AAV.RK.coRPGR was used to compare treatment effect vs. natural disease process.

The second design was a masked trial with a random selection of eyes receiving AAV.RK.coRPGR or AAV.control. The latter trial was used to control for the effect of surgery and AAV exposure. All 129 animals were treated with weaning at postnatal day P22±2 and tested at three subsequent time points: postnatal month 2 (PM2), PM4 and PM6 before sacrifice. ERG was recorded at all three time points and the cSLO was performed additionally at the last time point PM6.
Design of the Efficacy and Toxicology Study Rpgr−/y, C57BL/6JRd9/Boc, and C57BL/6J, mice were subjected to either a masked bilateral treatment testing AAV.RK.coRPGR vs. AAV.control (top) or an unilateral treatment with AAV.RK.coRPGR alone. All eyes were randomly assigned to verum vs. sham treatment or treatment vs. no treatment. Surgery was performed at postnatal day 22 (P22) and followed up at postnatal month 2 (PM2), PM4 and PM6 with electroretinography (ERG). At PM6, scanning laser ophthalmoscopy (SLO) was performed before sacrifice and processing of eyes for histology or Western blotting.
C57BL/6J Wild Type Mice A total of n=47 C57BL/6J mice were treated in the two trials to explore potential toxic effects of subretinal AAV2/8.RK.coRPGR delivery. 24 animals received unmasked unilateral treatment, where the eye was chosen in a randomised fashion. Treatment consisted of a single subretinal injection of $1.5 \times 10^9$ vg AAV2/8.RK.coRPGR diluted in BSS® with 0.001% PF-68. The remaining 23 animals received bilateral injections in a masked and randomised fashion. Treatment in the verum group was as above, while the control group received 1.5×109 vg AAV2/8. control diluted in the same vehicle (BSS® with 0.001% PF-68). Both vectors are described in detail in Example 4.

Subretinal injections were performed with weaning at 3 weeks of age. A grading system (0-10) was used by the surgeon to indicate quality of the subretinal injection, where 0/10 denotes no vector delivery and 10/10 full vector delivery without any form of complication such external (e.g. subconjunctival) or internal (e.g. intra-retinal/-vitreal) haemorrhage during or after the subretinal injection. A grade 9/10 was for example given in case of complete vector delivery, but minor subconjunctival bleed. Poor injections were defined as a grade ≤7 and were excluded from the trial.

Surgical intervention was followed by longitudinal observation of intraindividual changes in ERG recordings at postnatal month two (PM2) and PM4. At PM6, additional SLO imaging of the retina was performed immediately after ERG recordings. Mice were sacrificed at the last time point (PM6), and eyes dissected for transgene detection by Western blot or immunohistochemistry.

C57BL/6JRd9/Boc Mice

A total of n=36 C57BL/6JRd9/Boc mice were treated in both trials. 19 animals received unmasked unilateral treatment, while 17 animals were enrolled to receive masked and randomised bilateral injections with verum or control as described above for C57BL/6J mice. This was done to assess efficacy of AAV based RPGR gene replacement gene therapy. Follow-up was scheduled as above.

Rpgr−/y Mice

Rpgr−/y mice were used to assess efficacy of AAV based RPGR gene replacement gene therapy in a second animal model of XLRP. For this, a total of n=46 were treated in the two separate trials described above. 25 animals received unmasked unilateral treatment, while 21 animals were treated in both eyes (verum and control) as described above. Post-interventional readout was scheduled as above for C57BL/6J mice.

Results

Sample Size and Power Calculations

Calculated sample size was based on ERG data collected from four eyes (two animals) per cohort (C57BL/6J, C57BL/6JRd9/Boc, and Rpgr−/y mice). The average a-wave amplitude of n=9 trials was recorded for each eye.

After calculating the µ0, µ1 and sigma values from the data above, the suggested sample sizes ranged from 16 to 21. The C57BL/6JRd9/Boc mice featured the smallest amplitude (65±11 µN; mean±standard deviation) compared to the wild type control (81±7 µV) and therefore only required an estimated sample size of n=16. The suggested sample size for Rpgr−/y was n=21 due to its higher amplitude at baseline (728 µV). Power calculations showed that a loss of 10% amplitude from baseline in wild type mice would be detected with a power of 100% using a cohort size of n=20.

C57BL/6J Wild Type Mice

Six eyes were excluded from the trial due to poor surgery and one was excluded due to preexisting anterior segment changes. This resulted in an overall cohort size of n=19 for the unilateral trial and n=22 for the bilateral trial. The average [and range] of the documented surgical quality was very similar in all groups: 9.0 [8-10] for the open label, 9.5 [8-10] for the verum and 9.3 [8-10] in the control group. All mice recovered quickly after surgery.

None of the recorded signal intensity series either under dark or light adapted conditions showed a significant difference between treated vs. untreated or between verum vs. control group at any time point. Retinal imaging with scanning laser ophthalmoscopy (SLO) also confirmed that there was no toxic effect to be observed on retinal structure up to 6 month after subretinal application of AAV.RK.coR-PGR.

ERG recordings in C57BL/6J mice after bilateral subretinal injection of AAV.RK.coRPGR or AAV. control provided data from PM2, from PM4 and from PM6, the last time point tested. Factorial ANOVA for repeated measures retained the null hypothesis (no difference) in all analyses.

Western blot of whole retinal lysate confirmed RPGR transgene expression in the treated, but not in the control eye. The band showed the predicted molecular weight and no extra bands were apparent. Immunohistochemistry of unfixed cryosections also demonstrated RPGR transgene expression and co-localisation with native Rpgrip in the treated eye, but not the untreated control eye.

Hematoxylin and eosin (H&E) staining in retinal sections from treated eyes (TE) and untreated eyes (UE) revealed normal retinal anatomy in both cohorts. Neither of the cohorts showed any sign of inflammation or degeneration in any of the sections.

Western blot of whole retinal lysates from treated vs. untreated eyes of C57BL/6J, C57BL/6JRd9/Boc, and Rpgr−/y mice was done. RpgrORF15 expression was limited to the treated eyes and showed a band at ca. 200 kDa. The strongest band was visible in C57BL/6JRd9/Boc, followed by C57BL/6J, while the Rpgr−/y sample showed weakest expression. GAPDH was used as loading control (red). Naive HEK293T cells were used as negative control (nc) and HEK293T cells transfected with a coRPGR expression plasmid as positive control.

Immunohistochemistry in C57BL/6J mice. No RPGR expression in a control treated eye was seen. Treatment with AAV.coRPGR resulted in RPGR expression and co-localisation of human RPGR with Rpgrip.

Haematoxylin and eosin staining in C57BL/6J mice showed there were no signs of inflammation or degeneration visible in any section. Normal anatomy was observed.

C57BL/6JRd9/Boc Mice

One mouse of the unilateral open label trial had to be excluded due to a preexisting corneal infiltrate with associated microphthalmus in the untreated control eye. The microphthalmus may have led to false low ERG recordings in the untreated eye. This resulted in a total of n=18 for the unilateral trial, and n=17 animals for bilateral injections. None of the treated animals had to be excluded due to surgical complications and all animals received injections rated good or excellent with mean (range was 8-10 in all groups) of 9.7 for the open label, 9.1 for the verum and 9.0 in the control group.

In the longitudinal follow up, two animals from the unilateral trial did not recover from anaesthesia at PM4. A total of 102 bilateral ERG data sets from three time points were successfully recorded and saved for further analysis. In the open label, unilateral trial, factorial ANOVA for repeated measures retained the null hypothesis (no difference) at the first time point (PM2), but showed a trend for larger amplitudes for the treated eyes at higher intensities in both dark- and light adapted intensity series. At PM4, the treated eyes responded with significantly higher amplitudes across the dark adapted intensity series regarding both a-wave ($p=0.001$) and b-wave ($p=0.002$). The light adapted responses were not significantly different. This pattern was sustained until the last time point (PM6).

In the masked bilateral trial null hypothesis was retained at all time points. However, verum treated eyes always showed a trend for higher amplitudes again especially at higher stimulus intensities.

Retinal imaging with scanning laser ophthalmoscopy (SLO) also confirmed that there was no toxic effect to be observed on retinal structure up to 6 month after subretinal application of AAV.RK.coRPGR. However, autofluorescence imaging revealed a change in the disease presentation in treated C57BL/6JRd9/Boc mice: We showed previously that lack of Rpgr expression in mice is associated with hyperfluorescent dots across the retina visible in autofluorescence, while wild type mice only have minimal, homogenous autofluorescence signal. Interestingly, imaging in the verum treated eyes at PM6 showed a reduction of these hyperfluorescent dots in the superior hemiretina, where the vector was initially applied. Hemiretinal fields were significantly different within the treated eyes: 13±14 (meanistandard deviation) in the treated superior hemiretina vs. 59±40 in the ipsilateral inferior retina (p=0.005; n=6, paired t-test). Comparing the superior hemiretina of the treated vs. the contralateral untreated retina produced a similar result (p=0.037; n=6, paired ttest).

Western blot of whole retinal lysate confirmed RPGR transgene expression in the treated, but not in the control eye. The band showed the predicted molecular weight and no extra bands were apparent. Immunohistochemistry of unfixed cryosections also demonstrated RPGR transgene expression and co-localisation with native Rpgrip in the treated eye, but not the control eye.

Rpgr−/y Mice

One mouse of the unilateral open label trial had to be excluded due to preexisting microphthalmus in the untreated eye that was noticed only after surgical intervention of the contralateral eye and would have led to false low ERG recordings in the untreated eye. Additionally, one animal from the bilateral trial of the treated animals had to be excluded due to surgical complications (part intravitreal injection with intravitreal haemorrhage). This resulted in a total of n=24 for the unilateral trial, and n=20 animals for bilateral injections. The surgical success rate was high in all cohorts: Mean [range] ratings were 9.3 [8-10] for the open label, 9.5 [9-10] for the verum and Immunohistochemistry in C57BL/6JRd9/Boc mice. Top panels show no RPGR expression in a control-treated eye. Treatment with AAV.coRPGR resulted in RPGR expression and its co-localisation with Rpgrip. Scale bar indicates 20 μm. 9.4 [8-10] in the control group. In the longitudinal follow up, one bilaterally injected animal at PM2 and two animals with unilateral injections at PM4 did not recover from anaesthesia. A total of 128 bilateral ERG data sets from three time points were successfully recorded and saved for further analysis.

In the open label, unilateral trial, there was no apparent difference between eyes at the earliest time point (PM2), but a robust treatment effect visible in the dark adapted ERG responses at PM4 (p<0.001) and PM6 (p<0.001) in both a- and b-wave amplitudes. Photopic b-wave responses were significantly greater at PM6 (p=0.004). The masked bilateral trial showed significantly increased amplitudes of dark adapted b-wave responses at PM6, and light adapted b-wave amplitude was significantly increased at PM4 (but not at PM6).

Eyes of Rpgr−/y mice treated with AAV.RK.coRPGR showed a reduction of hyperfluorescent dots in the superior hemiretina, as also seen in treated C57BL/6JRd9/Boc mice. In contrast, untreated or sham treated eyes of Rpgr−/y mice showed the ubiquitous pattern of hyperfluorescent dots associated with Rpgr-null mutations.

Western blot of whole retinal lysate confirmed RPGR transgene expression in the treated, but not in the control eye. The band showed the predicted molecular weight and no extra bands were apparent. Immunohistochemistry of unfixed cryosections also demonstrated RPGR transgene expression and co-localisation with native Rpgrip in the treated eye, but not the control eye. ERG recordings in Rpgr−/y mice after unilateral subretinal injection of AAV.RK.coRPGR.

ERG recordings in Rpgr−/y mice after bilateral subretinal injection of AAV.RK.coRPGR or AAV. control. Treatment with AAV.RK.coRPGR led to significant improvement of dark adapted ERG amplitudes. The treatment effect in the light adapted b-wave amplitudes was not sustained at PM6.

Using scanning laser ophthalmoscopy imaging in the infrared mode, focal plane was set to inner retina or outer retina. A distinctly different autofluorescence pattern between the treated and sham or control eyes: The treated eye shows fewer hyperfluorescent dots in the superior hemiretina—the area of AAV.RK.coRPGR application.

Immunohistochemistry in Rpgr−/y mice. No RPGR expression in a control treated eye was seen. Treatment with AAV.coRPGR resulted in RPGR expression and co-localisation of human RPGR with Rpgrip. Scale bar indicates 20μηι.

Discussion

RPGR replacement therapy has attracted interest since the characterisation RPGR as the genetic cause for XLRP3. The fact that it still is a goal that has not translated into a clinical trial is mainly due to the fact that RPGR is a complex gene with high propensity for mutational changes. This has caused serious delays in the development of datasets for the support of clinical trial applications. And even with regulatory approval for a safety trial, production of clinical grade AAV for RPGR gene therapy will be a significant challenge.

These data show no toxic effects in wild type animals, C57BL/6J, and show efficacy of a new type of vector construct for RPGR gene therapy in two relevant animal models (Rpgr−/y and C57BL/6JRd9/Boc mice). This AAV based vector features a codon optimised coding sequence of RPGRORF15, which makes the construct more genetically stable while leading to the identical protein product, RPGRORF15. After extensive in vitro analyses and a pilot trial in Rpgr−/y mice (Example 4), the present invention shows that a single subretinal application of AAV.RK.coRPGR is safe and may stop or slow down the progression of retinal degeneration due to mutations in Rpgr.

Safety

To explore potential toxic effects of AAV.RK.coRPGR, we tested the same dose (1.5×109 vg in 1.5 μl) in forty-one C57BL/6J mice. Nineteen mice were treated in one eye only, while 22 received masked bilateral treatment with either AAV.RK.coRPGR or AAV.control. There were no significant differences between measures of retinal function in ERG at any time point of either trial between the verum group and the control or untreated group. Additionally, in vivo retinal imaging suggests that there was no impact of AAV.RK.coRPGR treatment on retinal structure. H&E staining showed no toxic effects of the treatment and immunohistochemistry and Western blotting demonstrated RPGRORF15 expression and localisation in treated animals, but not in untreated or control treated animals. Taken together, a single treatment of wild type mice with AAV.RK.coRPGR did not induce any toxic effects and showed a good safety profile. We therefore concluded that treatment with AAV.RK.coRPGR was safe.

Efficacy

The therapeutic effect of AAV.RK.coRPGR was demonstrated in two well characterised mouse models of XLRP3: The transgenic model Rpgr−/y and C57BL/6JRd9/Boc featuring a naturally occurring mutation in Rpgr. Both models have been shown to lack RpgrORF15 expression in the retina and hence were chosen as relevant animal models for XLRP3. However, there are some caveats with using these animal models. Most importantly, the disease phenotype is surprisingly mild, which necessitates relatively large cohorts in a trial to gain the necessary statistical power. As a consequence, we conducted trials in a total of c. 80 animals and provided robust evidence of efficacy as indicated by significant rescue of electrophysiological measurements in Rpgr−/y and C57BL/6JRd9/Boc mice.

The treatment did not become evident at the first time point most likely due to the slow disease progression in both animal models. However, AAV.RK.coRPGR treatment was associated with significant ERG rescue in both animal models at PM4 and PM6. This rescue was more evident in the dark adapted intensity series, which reflects the sum potential of rod photoreceptors in the lower intensity range (single flashes up to c. 0.01cd./m2). Higher flash intensities are thought to stimulate a mixed cone-rod response. The biggest difference between the treated and sham-/untreated eyes were seen at intensities around 1 cd·s/m2 indicating that both rod and cone photoreceptors might have gained from AAV.RK.coRPGR transduction.

Taken together, treatment with AAV.RK.coRPGR was safe and effective. Successful transduction of photoreceptors with AAV.RK.coRPGR in wild type mice did not lead to toxic effects that are associated with the expression of RPGRORF15. Furthermore, treatment of animal models of XLRP3 showed a statistically significant rescue of ERG responses in the treated, but not in the untreated eyes. These data demonstrated that the codon optimised coding sequence of RPGRORF15 of the present invention can be used to safely treat eyes.

What is claimed is:

1. A composition comprising a nucleic acid comprising
   (a) a sequence encoding a rhodopsin kinase promoter, and
   (b) a sequence encoding a retinitis pigmentosa GTPase regulator ORF15 isoform (RPGR$^{ORF15}$) and comprising a nucleotide sequence that has at least 80% identity to the nucleic acid sequence of SEQ ID NO: 3.

2. The composition of claim 1, wherein the sequence encoding the promoter has at least 80% identity to the nucleic acid sequence of SEQ ID NO: 7.

3. The composition of claim 1, wherein the sequence encoding the promoter has at least 90% identity to the nucleic acid sequence of SEQ ID NO: 7.

4. The composition of claim 1, wherein the sequence encoding the promoter comprises the nucleic acid sequence of SEQ ID NO: 7.

5. The composition of claim 1, wherein the sequence encoding the promoter consists of the nucleic acid sequence of SEQ ID NO: 7.

6. The composition of claim 1, wherein the sequence encoding the RPGR$^{ORF15}$ comprises a nucleotide sequence encoding an amino acid sequence that has at least 80% identity to the amino acid sequence of SEQ ID NO: 1.

7. The composition of claim 2, wherein the sequence encoding the RPGR$^{ORF15}$ comprises a nucleotide sequence encoding an amino acid sequence that has at least 80% identity to the amino acid sequence of SEQ ID NO: 1.

8. The composition of claim 3, wherein the sequence encoding the RPGR$^{ORF15}$ comprises a nucleotide sequence encoding an amino acid sequence that has at least 80% identity to the amino acid sequence of SEQ ID NO: 1.

9. The composition of claim 4, wherein the sequence encoding the RPGR$^{ORF15}$ comprises a nucleotide sequence encoding an amino acid sequence that has at least 80% identity to the amino acid sequence of SEQ ID NO: 1.

10. The composition of claim 5, wherein the sequence encoding the RPGR$^{ORF15}$ comprises a nucleotide sequence encoding an amino acid sequence that has at least 80% identity to the amino acid sequence of SEQ ID NO: 1.

11. The composition of claim 1, wherein the sequence encoding the RPGR$^{ORF15}$ comprises a nucleotide sequence that has at least 97% identity to the nucleic acid sequence of SEQ ID NO: 3.

12. The composition of claim 2, wherein the sequence encoding the RPGR$^{ORF15}$ comprises a nucleotide sequence that has at least 97% identity to the nucleic acid sequence of SEQ ID NO: 3.

13. The composition of claim 3, wherein the sequence encoding the RPGR$^{ORF15}$ comprises a nucleotide sequence that has at least 97% identity to the nucleic acid sequence of SEQ ID NO: 3.

14. The composition of claim 4, wherein the sequence encoding the RPGR$^{ORF15}$ comprises a nucleotide sequence that has at least 97% identity to the nucleic acid sequence of SEQ ID NO: 3.

15. The composition of claim 5, wherein the sequence encoding the RPGR$^{ORF15}$ comprises a nucleotide sequence that has at least 97% identity to the nucleic acid sequence of SEQ ID NO: 3.

* * * * *

```
                          SEQUENCE LISTING

<160> NUMBER OF SEQ ID NOS: 14

<210> SEQ ID NO 1
<211> LENGTH: 1152
<212> TYPE: PRT
<213> ORGANISM: Homo sapiens

<400> SEQUENCE: 1

Met Arg Glu Pro Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
    210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255
```

```
Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
            275                 280                 285

Ile Glu Asn Ile Arg Asp Gln Thr Ile Ser Tyr Ile Ser Cys Gly Glu
            290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
            370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
            405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
            450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Thr
            515                 520                 525

Ile Gly Glu Leu Thr Gln Asp Thr Ala Leu Thr Glu Asn Asp Asp Ser
            530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
            580                 585                 590

Ala Glu Asp Ser Lys Gly Asn Gly Ile Glu Glu Gln Glu Val Glu Ala
            595                 600                 605

Asn Glu Glu Asn Val Lys Val His Gly Gly Arg Lys Glu Lys Thr Glu
            610                 615                 620

Ile Leu Ser Asp Asp Leu Thr Asp Lys Ala Glu Val Ser Glu Gly Lys
625                 630                 635                 640

Ala Lys Ser Val Gly Glu Ala Glu Asp Gly Pro Glu Gly Arg Gly Asp
                645                 650                 655

Gly Thr Cys Glu Glu Gly Ser Ser Gly Ala Glu His Trp Gln Asp Glu
            660                 665                 670
```

-continued

```
Glu Arg Glu Lys Gly Glu Lys Asp Lys Gly Arg Gly Met Glu Arg
            675                 680                 685

Pro Gly Glu Gly Glu Lys Glu Leu Ala Glu Lys Glu Glu Trp Lys Lys
    690                 695                 700

Arg Asp Gly Glu Glu Gln Glu Gln Lys Glu Arg Glu Gln Gly His Gln
705                 710                 715                 720

Lys Glu Arg Asn Gln Glu Met Glu Glu Gly Glu Glu His Gly
                725                 730                 735

Glu Gly Glu Glu Glu Gly Asp Arg Glu Glu Glu Glu Lys Glu
                740                 745                 750

Gly Glu Gly Lys Glu Glu Gly Glu Glu Val Glu Gly Glu Arg
                755                 760                 765

Glu Lys Glu Glu Gly Glu Arg Lys Lys Glu Glu Arg Ala Gly Lys Glu
    770                 775                 780

Glu Lys Gly Glu Glu Glu Gly Asp Gln Gly Glu Gly Glu Glu Glu
785                 790                 795                 800

Thr Glu Gly Arg Gly Glu Glu Lys Glu Glu Gly Gly Glu Val Glu Gly
                805                 810                 815

Gly Glu Val Glu Glu Gly Lys Gly Glu Arg Glu Glu Glu Glu Glu
                820                 825                 830

Gly Glu Gly Glu Glu Glu Glu Gly Glu Glu Glu Glu Gly Glu
                835                 840                 845

Gly Glu Glu Glu Glu Gly Glu Lys Gly Glu Glu Glu Glu Glu Glu
                850                 855                 860

Gly Glu Gly Glu Glu Gly Glu Glu Gly Glu Gly Glu Gly Glu Gly Glu
865                 870                 875                 880

Glu Glu Gly Glu Gly Glu Gly Glu Glu Gly Glu Gly Glu Gly Glu
                885                 890                 895

Glu Glu Glu Gly Glu Gly Glu Gly Glu Glu Gly Glu Gly Glu Gly
                900                 905                 910

Glu Glu Glu Glu Gly Glu Gly Lys Gly Glu Glu Glu Gly Glu Glu Gly
                915                 920                 925

Glu Gly Glu Gly Glu Glu Glu Gly Glu Gly Glu Gly Glu Asp Gly
    930                 935                 940

Glu Gly Glu Gly Glu Glu Glu Gly Glu Trp Glu Gly Glu Glu Glu
945                 950                 955                 960

Glu Gly Glu Gly Glu Gly Glu Glu Gly Glu Gly Glu Gly Glu Glu
                965                 970                 975

Gly Glu Gly Glu Gly Glu Glu Glu Gly Glu Gly Glu Gly Glu Glu
                980                 985                 990

Glu Glu Gly Glu Gly Glu Gly Glu Glu Glu Gly Glu Gly Glu Glu Glu
                995                 1000                1005

Gly Glu Gly Glu Gly Glu Glu Glu Glu Glu Gly Glu Val Glu Gly
    1010                1015                1020

Glu Val Glu Gly Glu Glu Gly Glu Gly Glu Gly Glu Glu Glu Glu
    1025                1030                1035

Gly Glu Glu Glu Gly Glu Glu Arg Glu Lys Glu Gly Glu Gly Glu
    1040                1045                1050

Glu Asn Arg Arg Asn Arg Glu Glu Glu Glu Glu Glu Glu Gly Lys
    1055                1060                1065

Tyr Gln Glu Thr Gly Glu Glu Glu Asn Glu Arg Gln Asp Gly Glu
    1070                1075                1080

Glu Tyr Lys Lys Val Ser Lys Ile Lys Gly Ser Val Lys Tyr Gly
```

```
              1085                1090                1095
Lys His Lys Thr Tyr Gln Lys Lys Ser Val Thr Asn Thr Gln Gly
     1100                1105                1110

Asn Gly Lys Glu Gln Arg Ser Lys Met Pro Val Gln Ser Lys Arg
     1115                1120                1125

Leu Leu Lys Asn Gly Pro Ser Gly Ser Lys Lys Phe Trp Asn Asn
     1130                1135                1140

Val Leu Pro His Tyr Leu Glu Leu Lys
     1145                1150

<210> SEQ ID NO 2
<211> LENGTH: 3459
<212> TYPE: DNA
<213> ORGANISM: Homo sapiens

<400> SEQUENCE: 2 atgggagc cggaagagct gatgcccgat tcgggtgctg tgtttacatt tgggaaaagt        60
aaatttgctg aaaataatcc cggtaaattc tggtttaaaa atgatgtccc tgtacatctt    120
tcatgtggag atgaacattc tgctgttgtt accggaaata taaacttta catgtttggc     180 agtaacaact ggggtcagtt aggattagga tcaaagtcag ccatcagcaa gccaacatgt    240
gtcaaagctc taaaacctga aaaagtgaaa ttagctgcct gtggaaggaa ccacaccctg    300
gtgtcaacag aaggaggcaa tgtatatgca actggtggaa ataatgaagg acagttgggg    360
cttggtgaca ccgaagaaag aaacactttt catgtaatta gctttttttac atccgagcat    420 aagattaagc agctgtctgc tggatctaat acttcagctg ccctaactga ggatggaaga    480 cttttttatgt ggggtgacaa ttccgaaggg caaattggtt taaaaaatgt aagtaatgtc    540
tgtgtccctc agcaagtgac cattgggaaa cctgtctcct ggatctcttg tggatattac    600
cattcagctt ttgtaacaac agatggtgag ctatatgtgt ttggagaacc tgagaatggg    660
aagttaggtc ttcccaatca gctcctgggc aatcacagaa cacccagct ggtgtctgaa      720 attccggaga aggtgatcca agtagcctgt ggtggagagc atactgtggt tctcacggag    780
aatgctgtgt atacctttgg gctgggacaa tttggtcagc tgggtcttgg cacttttctt    840
tttgaaactt cagaacccaa agtcattgag aatattaggg atcaaacaat aagttatatt    900
tcttgtggag aaaatcacac agctttgata acagatatcg gccttatgta acttttgga    960 gatggtcgcc acggaaaatt aggacttgga ctggagaatt ttaccaatca cttcattcct    1020
actttgtgct ctaatttttt gaggtttata gttaaattgg ttgcttgtgg tggatgtcac    1080
atggtagttt ttgctgctcc tcatcgtggt gtggcaaaag aaattgaatt cgatgaaata    1140
aatgatactt gcttatctgt ggcgactttt ctgccgtata gcagtttaac ctcaggaaat    1200
gtactgcaga ggactctatc agcacgtatg cggcgaagag agagggagag gtctccagat    1260 tcttttttcaa tgaggagaac actacctcca atagaaggga ctcttggcct ttctgcttgt    1320
tttctcccca attcagtctt tccacgatgt tctgagagaa acctccaaga gagtgtctta    1380
tctgaacagg acctcatgca gccagaggaa ccagattatt tgctagatga aatgaccaaa    1440
gaagcagaga tagataattc ttcaactgta gaaagccttg gagaaactac tgatatctta    1500
aacatgacac acatcatgag cctgaattcc aatgaaaagt cattaaaatt atcaccagtt    1560
cagaaacaaa agaaacaaca acaattgggg gaactgacgc aggatacagc tcttactgaa    1620
aacgatgata gtgatgaata tgaagaaatg tcagaaatga agaagggaa agcatgtaaa    1680 caacatgtgt cacaagggat tttcatgacg cagccagcta cgactatcga agcattttca    1740
```

```
gatgaggaag tagagatccc agaggagaag gaaggagcag aggattcaaa aggaaatgga    1800
atagaggagc aagaggtaga agcaaatgag gaaaatgtga aggtgcatgg aggaagaaag    1860
gagaaaacag agatcctatc agatgacctt acagacaaag cagaggtgag tgaaggcaag    1920
gcaaaatcag tgggagaagc agaggatggg cctgaaggta gaggggatgg aacctgtgag    1980
gaaggtagtt caggagcaga acactggcaa gatgaggaga gggagaaggg ggagaaagac    2040
aagggtagag gagaaatgga gaggccagga gaggagagaga aggaactagc agagaaggaa    2100
gaatggaaga gagggatggg gaagagcag gagcaaaagg agagggagca gggccatcag    2160
aaggaaagaa accaagagat ggaggaggga ggggaggagg agcatggaga aggagaagaa    2220
gaggagggag acagagaaga ggaagaagag aaggagggag aagggaaaga ggaaggagaa    2280
ggggaagaag tggagggaga acgtgaaaag gaggaaggag agaggaaaaa ggaggaaaga    2340
gcggggaagg aggagaaagg agaggaagaa ggagaccaag gagaggggga gaggaggaa    2400 acagagggga gaggggagga aaaagaggag ggagggggaag tagagggagg ggaagtagag    2460
gaggggaaag gagagagggga agaggaagag gaggagggtg agggggaaga ggaggaaggg    2520 gaggggggaag aggaggaagg ggaggggaa gaggaggaag gagaagggaa aggggaggaa    2580
gaaggggaag aaggagaagg ggaggaagaa ggggaggaag gagaagggga ggggggaagag    2640 gaggaaggag aagggaggg agaagaggaa ggagaagggg agggagaaga ggaggaagga    2700
gaaggggagg gagaagagga aggagaaggg gaggagaag aggaggaagg agaagggaaa    2760
gggaaggagg aaggagagga aggagaaggg gaggggggaag aggaggaagg agaaggggaa    2820
ggggaggatg gagaaggga ggggggaagag gaggaaggag aatgggaggg ggaagaggag    2880
gaaggagaag gggaggggga agaggaagga gaaggggaag gggaggaagg agaaggggag    2940
ggggaagagg aggaaggaga aggggagggg gaagaggagg aaggggaaga gaagggggag    3000
gaagaaggag agggagagga agaaggggag ggagaagggg aggaagaaga ggaagggaa    3060 gtggaagggg aggtggaagg ggaggaagga gaggggggaag gagaggaaga ggaaggagag    3120
gaggaaggag aagaaaggga aaaggagggg gaaggagaag aaaacaggag gaacagagaa    3180
gaggaggagg aagaaagagggg gaagtatcag gagacaggcg aagaagagaa tgaaaggcag    3240
gatggagagg agtacaaaaaa agtgagcaaa ataaaaggat ctgtgaaata tggcaaacat    3300
aaaacatatc aaaaaaagtc agttactaac acacaggaa atgggaaga gcagaggtcc    3360 aaaatgccag tccagtcaaa acgactttta aaaacgggc catcaggttc caaaaagttc    3420
tggaataatg tattaccaca ttacttggaa ttgaagtaa                          3459

<210> SEQ ID NO 3
<211> LENGTH: 3459
<212> TYPE: DNA
<213> ORGANISM: Artificial Sequence
<220> FEATURE:
<223> OTHER INFORMATION: codon-optimised sequence of RPGRORF15

<400> SEQUENCE: 3
atgagagagc cagaggagct gatgccagac agtggagcag tgtttacatt cggaaaatct     60
aagttcgctg aaaataaccc aggaaagttc tggtttaaaa acgacgtgcc cgtccacctg    120
tcttgtggcg atgagcatag tgccgtggtc actgggaaca ataagctgta catgttcggg    180
tccaacaact ggggacagct ggggctggga tccaaatctg ctatctctaa gccaacctgc    240
gtgaaggcac tgaaacccga aaggtcaaa ctggccgctt gtggcagaaa ccacactctg    300
```

```
gtgagcaccg agggcgggaa tgtctatgcc accggaggca caatgaggg acagctggga    360 ctggggaca ctgaggaaag gaatacccttt cacgtgatct ccttctttac atctgagcat    420
aagatcaagc agctgagcgc tggctccaac acatctgcag ccctgactga ggacgggcgc    480
ctgttcatgt ggggagataa ttcagagggc cagattgggc tgaaaaacgt gagcaatgtg    540
tgcgtccctc agcaggtgac catcggaaag ccagtcagtt ggatttcatg tggctactat    600
catagcgcct tcgtgaccac agatggcgag ctgtacgtct ttggggagcc cgaaaacgga    660
aaactgggcc tgcctaacca gctgctgggc aatcaccgga caccccagct ggtgtccgag    720
atccctgaaa aagtgatcca ggtcgcctgc gggggagagc atacagtggt cctgactgag    780
aatgctgtgt ataccttcgg actgggccag tttggccagc tggggctggg aaccttcctg    840
tttgagacat ccgaaccaaa agtgatcgag aacattcgcg accagactat cagctacatt    900
tcctgcggag agaatcacac cgcactgatc acagacattg gcctgatgta ccctttggc    960 gatggacgac acgggaagct gggactggga ctggagaact tcactaatca tttatcccc    1020 accctgtgtt ctaacttcct gcggttcatc gtgaaactgg tcgcttgcgg cgggtgtcac    1080
atggtggtct cgctgcacc tcataggggc gtggctaagg agatcgaatt tgacgagatt    1140
aacgatacat gcctgagcgt ggcaactttc ctgcccatca gctccctgac ttctggcaat    1200
gtgctgcaga gaaccctgag tgcaaggatg cggagaaggg agaggaacg ctctcctgac    1260 agtttctcaa tgcgacgaac cctgccacct atcgagggaa cactgggact gagtgcctgc    1320
ttcctgccta actcagtgtt tccacgatgt agcgagcgga atctgcagga gtctgtcctg    1380
agtgagcagg atctgatgca gccagaggaa cccgactacc tgctggatga gatgaccaag    1440
gaggccgaaa tcgacaactc tagtacagtg gagtccctgg gcgagactac cgatatcctg    1500
aatatgacac acattatgtc actgaacagc aatgagaaga gtctgaaact gtcaccagtg    1560
cagaagcaga agaaacagca gactattggc gagctgactc aggacaccgc cctgacagag    1620
aacgacgata gcgatgagta tgaggaaatg tccgagatga aggaaggcaa agcttgtaag    1680
cagcatgtca gtcaggggat cttcatgaca cagccagcca caactattga ggctttttca    1740
gacgaggaag tggagatccc cgaggaaaaa gaggggcgcag aagattccaa ggggaatgga    1800
attgaggaac aggaggtgga agccaacgag gaaaatgtga agtccacgg aggcaggaag    1860 gagaaaacag aaatcctgtc tgacgatctg actgacaagg ccgaggtgtc cgaaggcaag    1920
gcaaaatctg tcggagaggc agaagacgga ccagagggac gaggggatgg aacctgcgag    1980
gaaggctcaa gcggggctga gcattggcag gacgaggaac gagagaaggg cgaaaaggat    2040
aaaggccgcg gggagatgga acgacctgga gagggcgaaa aagagctggc agagaaggag    2100
gaatggaaga aaagggacgg cgaggaacag gagcagaaaa aaagggagca gggccaccag    2160
aaggagcgca accaggagat ggaagagggc ggcgaggaag agcatggcga gggagaagag    2220
gaagagggcg atagaagaga ggaagaggaa aaagaaggcg aagggaagga ggaaggagag    2280
ggcgaggaag tggaaggcga gagggaaaag gaggaaggag aacggaagaa agaggaaaga    2340
gccggcaaag aggaaaaggg cgaggaagag ggcgatcagg gcgaaggcga ggaggaagag    2400
accgagggcc gcggggaaga gaagaggag ggaggagagg tggagggcgg agaggtcgaa    2460
gagggaaagg gcgagcgcga agaggaagag gaagagggcg agggcgagga agaagagggc    2520
gagggggaag aagaggaggg agagggcgaa gaggaagagg gggagggaaa gggcgaagag    2580
gaaggagagg aaggggaggg agaggaagag ggggaggagg gcgaggggga aggcgaggag    2640
gaagaaggag aggggggaagg cgaagaggaa ggcgaggggg aaggagagga ggaagaaggg    2700
```

```
gaaggcgaag gcgaagagga gggagaagga gaggggagg aagaggaagg agaagggaag    2760
ggcgaggagg aaggcgaaga gggagagggg gaaggcgagg aagaggaagg cgagggcgaa    2820
ggagaggacg gcgagggcga gggagaagag gaggaagggg aatgggaagg cgaagaagag    2880
gaaggcgaag gcgaaggcga agaagagggc gaaggggagg gcgaggaggg cgaaggcgaa    2940
ggggaggaag aggaaggcga aggagaaggc gaggaagaag agggagagga ggaaggcgag    3000
gaggaaggag aggggagga ggaggagaa ggcgagggcg aagaagaaga agagggagaa    3060
gtggagggcg aagtcgaggg ggaggaggga gaaggggaag gggaggaaga agagggcgaa    3120
gaagaaggcg aggaaagaga aaagagggga gaaggcgagg aaaaccggag aaatagggaa    3180
gaggaggaag aggaagaggg aaagtaccag gagacaggcg aagaggaaaa cgagcggcag    3240
gatggcgagg aatataagaa agtgagcaag atcaaaggat ccgtcaagta cggcaagcac    3300
aaaacctatc agaagaaaag cgtgaccaac acacagggga atggaaaaga gcagaggagt    3360
aagatgcctg tgcagtcaaa acggctgctg aagaatggcc catctggaag taaaaaattc    3420
tggaacaatg tgctgcccca ctatctggaa ctgaaataa                          3459

<210> SEQ ID NO 4
<211> LENGTH: 934
<212> TYPE: DNA
<213> ORGANISM: Artificial Sequence
<220> FEATURE:
<223> OTHER INFORMATION: promoter sequence

<400> SEQUENCE: 4
attgacgtca ataatgacgt atgttcccat agtaacgcca tagggactt tccattgacg      60 tcaatgggtg gagtatttac ggtaaactgc ccacttggca gtacatcaag tgtatcatat    120
gccaagtacg cccctattg acgtcaatga cggtaaatgg cccgcctggc attatgccca    180
gtacatgacc ttatgggact ttcctacttg gcagtacatc tacgtattag tcatcgctat    240
taccatggtc gaggtgagcc ccacgttctg cttcactctc cccatctccc cccctcccc    300 accccaatt ttgtatttat ttattttta attatttttgt gcagcgatgg gggcgggggg    360
gggggggggg cgcgcgccag gcggggcggg gcggggcgag gggcggggcg gggcgaggcg    420
gagaggtgcg gcggcagcca atcagagcgg cgcgctccga aagtttcctt ttatggcgag    480
gcggcggcgg cggcggccct ataaaaagcg aagcgcgcgg cgggcgggag tcgctgcgcg    540
ctgccttcgc cccgtgcccc gctccgccgc cgcctcgcgc cgcccgcccc ggctctgact    600
gaccgcgtta ctcccacagg tgagcgggcg gacggcccct tctcctccgg gctgtaatta    660
gcgcttggtt taatgacggc ttgtttcttt tctgtggctg cgtgaaagcc ttgaggggct    720 ccggggggc cctttgtgcg gggggagcgg ctcgggctg tccgcggggg acggctgcc      780 ttcgggggg acgggcagg gcggggttcg gcttctggcg tgtgaccggc ggctctagag     840
cctctgctaa ccatgttcat gccttcttct ttttcctaca gctcctgggc aacgtgctgg    900
ttattgtgct gtctcatcat tttggcaaag aatt                                934

<210> SEQ ID NO 5
<211> LENGTH: 270
<212> TYPE: DNA
<213> ORGANISM: Artificial Sequence
<220> FEATURE:
<223> OTHER INFORMATION: Bovine Growth Hormone poly-A signal sequence

<400> SEQUENCE: 5
```

```
tcgctgatca gcctcgactg tgccttctag ttgccagcca tctgttgttt gcccctcccc      60
cgtgccttcc ttgaccctgg aaggtgccac tcccactgtc ctttcctaat aaaatgagga     120
aattgcatcg cattgtctga gtaggtgtca ttctattctg gggggtgggg tggggcagga     180
cagcaagggg gaggattggg aagacaatag caggcatgct ggggatgcgg tgggctctat     240
ggcttctgag gcggaaagaa ccagctgggg                                      270

<210> SEQ ID NO 6
<211> LENGTH: 588
<212> TYPE: DNA
<213> ORGANISM: Artificial Sequence
<220> FEATURE:
<223> OTHER INFORMATION: woodchuck hepatitis postregulatory element
      (WPRE) example sequence

<400> SEQUENCE: 6
atcaacctct ggattacaaa atttgtgaaa gattgactgg tattcttaac tatgttgctc      60
cttttacgct atgtggatac gctgctttaa tgcctttgta tcatgctatt gcttcccgta     120
tggctttcat tttctcctcc ttgtataaat cctggttgct gtctctttat gaggagttgt     180
ggcccgttgt caggcaacgt ggcgtggtgt gcactgtgtt tgctgacgca acccccactg     240 gttgggcat tgccaccacc tgtcagctcc tttccgggac tttcgctttc cccctcccta     300
ttgccacggc ggaactcatc gccgcctgcc ttgcccgctg ctggacaggg gctcggctgt     360
tgggcactga caattccgtg tgttgtcgg ggaaatcatc gtccttttcct tggctgctcg     420 cctgtgttgc cacctggatt ctgcgcggga cgtccttctg ctacgtccct tcggccctca     480
atccagcgga ccttccttcc cgcggcctgc tgccggctct gcggcctctt ccgcgtcttc     540
gccttcgccc tcagacgagt cggatctccc tttgggccgc ctccccgc                  588

<210> SEQ ID NO 7
<211> LENGTH: 199
<212> TYPE: DNA
<213> ORGANISM: Artificial Sequence
<220> FEATURE:
<223> OTHER INFORMATION: rhodopsin kinase (GRK1) promoter sequence

<400> SEQUENCE: 7
gggccccaga agcctggtgg ttgtttgtcc ttctcagggg aaaagtgagg cggccccttg      60
gaggaagggg ccgggcagaa tgatctaatc ggattccaag cagctcaggg gattgtcttt     120
ttctagcacc ttcttgccac tcctaagcgt cctccgtgac cccggctggg atttagcctg     180
gtgctgtgtc agccccggg                                                  199

<210> SEQ ID NO 8
<211> LENGTH: 235
<212> TYPE: DNA
<213> ORGANISM: Artificial Sequence
<220> FEATURE:
<223> OTHER INFORMATION: interphotoreceptor retinoid-binding protein
      (IRBP) promoter sequence

<400> SEQUENCE: 8
agcacagtgt ctggcatgta gcaggaacta aaataatggc agtgattaat gttatgatat      60
gcagacacaa cacagcaaga taagatgcaa tgtaccttct gggtcaaacc accctggcca     120
ctcctccccg atacccaggg ttgatgtgct tgaattagac aggattaaag gcttactgga     180
gctggaagcc ttgccccaac tcaggagttt agccccagac cttctgtcca ccagc          235
```

```
<210> SEQ ID NO 9
<211> LENGTH: 3003
<212> TYPE: DNA
<213> ORGANISM: Artificial Sequence
<220> FEATURE:
<223> OTHER INFORMATION: a preferred RPGRORF15-encoding nucleotide
      sequence

<400> SEQUENCE: 9
```

| | | | | | |
|---|---|---|---|---|---|
| atgagagagc | cagaggagct | gatgccagac | agtggagcag | tgtttacatt | cggaaaatct | 60 |
| aagttcgctg | aaaataaccc | aggaaagttc | tggtttaaaa | acgacgtgcc | cgtccacctg | 120 |
| tcttgtggcg | atgagcatag | tgccgtggtc | actgggaaca | ataagctgta | catgttcggg | 180 |
| tccaacaact | ggggacagct | ggggctggga | tccaaatctg | ctatctctaa | gccaacctgc | 240 |
| gtgaaggcac | tgaaacccga | aaggtcaaa | ctggccgctt | gtggcagaaa | ccacactctg | 300 |
| gtgagcaccg | agggcgggaa | tgtctatgcc | accggaggca | caatgaggg | acagctggga | 360 |
| ctggggaca | ctgaggaaag | gaataccttt | cacgtgatct | ccttctttac | atctgagcat | 420 |
| aagatcaagc | agctgagcgc | tggctccaac | acatctgcag | ccctgactga | ggacgggcgc | 480 |
| ctgttcatgt | ggggagataa | ttcagagggc | cagattgggc | tgaaaaacgt | gagcaatgtg | 540 |
| tgcgtccctc | agcaggtgac | catcggaaag | ccagtcagtt | ggatttcatg | tggctactat | 600 |
| catagcgcct | tcgtgaccac | agatggcgag | ctgtacgtct | tggggagcc | gaaaacgga | 660 |
| aaactgggcc | tgcctaacca | gctgctgggc | aatcaccgga | cccccagct | ggtgtccgag | 720 |
| atccctgaaa | aagtgatcca | ggtcgcctgc | ggggagagc | atacagtggt | cctgactgag | 780 |
| aatgctgtgt | ataccttcgg | actgggccag | tttggccagc | tggggctggg | aaccttcctg | 840 |
| tttgagacat | ccgaaccaaa | agtgatcgag | aacattcgcg | accagactat | cagctacatt | 900 |
| tcctgcggag | agaatcacac | cgcactgatc | acagacattg | gcctgatgta | tacctttggc | 960 |
| gatggacgac | acgggaagct | gggactggga | ctggagaact | tcactaatca | ttttatcccc | 1020 |
| accctgtgtt | ctaacttcct | gcggttcatc | gtgaaactgg | tcgcttgcgg | cgggtgtcac | 1080 |
| atggtggtct | tcgctgcacc | tcatagggc | gtggctaagg | agatcgaatt | tgacgagatt | 1140 |
| aacgatacat | gcctgagcgt | ggcaactttc | ctgccataca | gctccctgac | ttctggcaat | 1200 |
| gtgctgcaga | gaaccctgag | tgcaaggatg | cggagaaggg | agagggaacg | ctctcctgac | 1260 |
| agtttctcaa | tgcgacgaac | cctgccacct | atcgagggaa | cactgggact | gagtgcctgc | 1320 |
| ttcctgccta | actcagtgtt | tccacgatgt | agcgagcgga | atctgcagga | gtctgtcctg | 1380 |
| agtgagcagg | atctgatgca | gccagaggaa | cccgactacc | tgctggatga | gatgaccaag | 1440 |
| gaggccgaaa | tcgacaactc | tagtacagtg | gagtccctgg | gcgagactac | cgatatcctg | 1500 |
| aatatgacac | acattatgtc | actgaacagc | aatgagaaga | gtctgaaact | gtcaccagtg | 1560 |
| cagaagcaga | gaaacagca | gactattggc | gagctgactc | aggacaccgc | cctgacagag | 1620 |
| aacgacgata | gcgatgagta | tgaggaaatg | tccgagatga | aggaaggcaa | agcttgtaag | 1680 |
| cagcatgtca | gtcagggat | cttcatgaca | cagccagcca | caactattga | ggcttttca | 1740 |
| gacgaggaag | tggagatccc | cgaggaaaaa | gagggcgcag | aagattccaa | ggggaatgga | 1800 |
| attgaggaac | aggaggtgga | agccaacgag | gaaaatgtga | agtccacgg | aggcaggaag | 1860 |
| gagaaaacag | aaatcctgtc | tgacgatctg | actgacaagg | ccgaggtgtc | cgaaggcaag | 1920 |
| gcaaaatctg | tcggagaggc | agaagacgga | ccagagggac | gaggggatgg | aacctgcgag | 1980 |
| gaaggctcaa | gcgggctga | gcattggcag | gacgaggaac | gagagaaggg | cgaaaaggat | 2040 |
| aaaggccgcg | gggagatgga | acgacctgga | gagggcgaaa | aagagctggc | agagaaggag | 2100 |

```
gaatggaaga aaagggacgg cgaggaacag gagcagaaag aaagggagca gggccaccag    2160
aaggagcgca accaggagat ggaagagggc ggcgaggaag agcatggcga gggagaagag    2220
gaagagggcg atagagaaga ggaagaggaa aaagaaggcg aagggaagga ggaaggagag    2280
ggcgaggaag tggaaggcga gagggaaaag gaggaaggag aacggaagaa agaggaaaga    2340
gccggcaaag aggaaaaggg cgaggaagag ggcgatcagg gcgaaggcga ggaggaagag    2400
accgagggcc gcggggaaga gaaagaggag ggaggagagg tggagggcgg agaggtcgaa    2460
gagggaaagg gcgagcgcga agagggggag gaagaggaag gcgaaggaga aggcgaggaa    2520
gaagagggag aggaggaagg cgaggaggaa ggagaggggg aggaggaggg agaaggcgag    2580
ggcgaagaag aagaagaggg agaagtggag ggcgaagtcg aggggaggga gggagaaggg    2640
gaaggggagg aagaagaggg cgaagaagaa ggcgaggaaa gagaaaaaga gggagaaggc    2700
gaggaaaacc ggagaaatag ggaagaggag gaagaggaag agggaaagta ccaggagaca    2760
ggcgaagagg aaaacgagcg gcaggatggc gaggaatata agaaagtgag caagatcaaa    2820
ggatccgtca agtacggcaa gcacaaaacc tatcagaaga aaagcgtgac caacacacag    2880
gggaatggaa aagagcagag gagtaagatg cctgtgcagt caaaacggct gctgaagaat    2940
ggcccatctg gaagtaaaaa attctggaac aatgtgctgc cccactatct ggaactgaaa    3000
taa                                                                 3003

<210> SEQ ID NO 10
<211> LENGTH: 456
<212> TYPE: DNA
<213> ORGANISM: Artificial Sequence
<220> FEATURE:
<223> OTHER INFORMATION: deletion sequence

<400> SEQUENCE: 10
gaagaggaag agggcgaggg cgaggaagaa gagggcgagg gggaagaaga ggagggagag      60
ggcgaagagg aagaggggga gggaaagggc gaagaggaag gagaggaagg ggaggagag     120 gaagaggggg aggagggcga gggggaaggc gaggaggaag aaggagaggg ggaaggcgaa     180
gaggaaggcg aggggggaagg agaggaggaa gaagggggaag gcgaaggcga agaggaggga   240
gaaggagagg gggaggaaga ggaaggagaa ggggaagggcg aggaggaagg cgaagaggga   300 gaggggggaag gcgaggaaga ggaaggcgag ggcgaaggag aggacggcga gggcgaggga   360
gaagaggagg aagggggaatg ggaaggcgaa gaagaggaag gcgaaggcga aggcgaagaa   420
gagggcgaag gggagggcga ggagggcgaa ggcgaa                             456

<210> SEQ ID NO 11
<211> LENGTH: 2517
<212> TYPE: DNA
<213> ORGANISM: Artificial Sequence
<220> FEATURE:
<223> OTHER INFORMATION: a preferred RPGRORF15-encoding nucleotide
      sequence

<400> SEQUENCE: 11
atgagagagc cagaggagct gatgccagac agtggagcag tgtttacatt cggaaaatct     60
aagttcgctg aaaataaccc aggaaagttc tggtttaaaa cgacgtgcc cgtccacctg     120 tcttgtggcg atgagcatag tgccgtggtc actgggaaca ataagctgta catgttcggg    180
tccaacaact ggggacagct ggggctggga tccaaatctg ctatctctaa gccaacctgc    240
gtgaaggcac tgaaacccga gaaggtcaaa ctggccgctt gtggcagaaa ccacactctg    300
```

```
gtgagcaccg agggcgggaa tgtctatgcc accggaggca acaatgaggg acagctggga    360
ctgggggaca ctgaggaaag gaatacctttt cacgtgatct ccttctttac atctgagcat   420
aagatcaagc agctgagcgc tggctccaac acatctgcag ccctgactga ggacgggcgc    480
ctgttcatgt ggggagataa ttcagagggc cagattgggc tgaaaaacgt gagcaatgtg    540
tgcgtccctc agcaggtgac catcggaaag ccagtcagtt ggatttcatg tggctactat    600
catagcgcct tcgtgaccac agatggcgag ctgtacgtct ttggggagcc cgaaaacgga    660
aaactgggcc tgcctaacca gctgctgggc aatcaccgga caccccagct ggtgtccgag    720
atccctgaaa aagtgatcca ggtcgcctgc ggggagagc atacagtggt cctgactgag     780
aatgctgtgt ataccttcgg actgggccag tttggccagc tggggctggg aaccttcctg    840
tttgagacat ccgaaccaaa agtgatcgag aacattcgcg accagactat cagctacatt    900
tcctgcggag agaatcacac cgcactgatc acagacattg gcctgatgta tacctttggc    960
gatggacgac acgggaagct gggactggga ctggagaact tcactaatca ttttatcccc    1020
accctgtgtt ctaacttcct gcggttcatc gtgaaactgg tcgcttgcgg cgggtgtcac    1080
atggtggtct tcgctgcacc tcataggggc gtggctaagg agatcgaatt tgacgagatt    1140
aacgatacat gcctgagcgt ggcaactttc ctgccataca gctccctgac ttctggcaat    1200
gtgctgcaga gaaccctgag tgcaaggatg cggagaaggg agaggaacg ctctcctgac     1260 agtttctcaa tgcgacgaac cctgccacct atcgagggaa cactgggact gagtgcctgc    1320
ttcctgccta actcagtgtt tccacgatgt agcgagcgga atctgcagga gtctgtcctg    1380
agtgagcagg atctgatgca gccagaggaa cccgactacc tgctggatga gatgaccaag    1440
gaggccgaaa tcgacaactc tagtacagtg gagtccctgg gcgagactac cgatatcctg    1500
aatatgacac acattatgtc actgaacagc aatgagaaga gtctgaaact gtcaccagtg    1560
cagaagcaga agaaacagca gactattggc gagctgactc aggacaccgc cctgacagag    1620
aacgacgata gcgatgagta tgaggaaatg tccgagtga aggaaggcaa agcttgtaag     1680
cagcatgtca gtcagggat cttcatgaca cagccagcca caactattga ggcttttttca   1740 gacgaggaag tggagatccc cgaggaaaaa gagggcgcag aagattccaa ggggaatgga    1800
attgaggaac aggaggtgga agccaacgag gaaaatgtga agtccacgg aggcaggaag     1860 gagaaaacag aaatcctgtc tgacgatctg actgacaagg ccgaggtgtc cgaaggcaag    1920
gcaaaatctg tcggagaggc agaagacgga ccagagggac gagggatgg aacctgcgag     1980 gaaggctcaa gcgggctgaa gcattggcag gacgaggaac gagagaaggg cgaaaaggat    2040
aaaggccgcg gggagatgga acgacctgga gagggcgaaa agaggaagg cgagggcgaa     2100 gaagaagaag agggagaagt ggagggcgaa gtcgagggg aggagggaga aggggaaggg     2160
gaggaagaag agggcgaaga agaaggcgag gaaagagaaa agagggagag aggcgaggaa    2220
aaccggagaa ataggaagga ggaggaagag gaagaggaa agtaccagga gacaggcgaa     2280
gaggaaaacg agcggcagga tggcgaggaa tataagaaag tgagcaagat caaaggatcc    2340
gtcaagtacg gcaagcacaa aacctatcag aagaaaagcg tgaccaacac acaggggaat    2400
ggaaaagagc agaggagtaa gatgcctgtg cagtcaaaac ggctgctgaa gaatggccca    2460
tctggaagta aaaaattctg gaacaatgtg ctgcccact atctggaact gaaataa       2517
```

<210> SEQ ID NO 12
<211> LENGTH: 942
<212> TYPE: DNA

<213> ORGANISM: Artificial Sequence
<220> FEATURE:
<223> OTHER INFORMATION: deletion sequence

<400> SEQUENCE: 12

```
ctggcagaga aggaggaatg gaagaaaagg gacggcgagg aacaggagca gaaagaaagg      60
gagcagggcc accagaagga gcgcaaccag gagatggaag agggcggcga ggaagagcat     120
ggcgagggag aagaggaaga gggcgataga gaagaggaag aggaaaaaga aggcgaaggg     180
aaggaggaag gagagggcga ggaagtggaa ggcgagaggg aaaaggagga aggagaacgg     240
aagaaagagg aaagagccgg caaagaggaa aagggcgagg aagagggcga tcagggcgaa     300
ggcgaggagg aagagaccga gggccgcggg gaagagaaag aggagggagg agaggtggag     360 ggcgagagg tcgaagaggg aaagggcgag cgcgaagagg aagaggaaga gggcgagggc     420
gaggaagaag agggcgaggg ggaagaagag gagggagagg gcgaagagga agaggggag     480 ggaaagggcg aagaggaagg agaggaaggg gagggagagg aagagggga ggagggcgag     540 ggggaaggcg aggaggaaga aggagagggg gaaggcgaag aggaaggcga gggggaagga    600
gaggaggaag aaggggaagg cgaaggcgaa gaggagggag aaggagaggg ggaggaagag    660
gaaggagaag ggaagggcga ggaggaaggc gaagagggag aggggaagg cgaggaagag    720 gaaggcgagg gcgaaggaga ggacggcgag ggcgagggag aagaggagga aggggaatgg   780
gaaggcgaag aagaggaagg cgaaggcgaa ggcgaagaag agggcgaagg ggagggcgag    840
gagggcgaag gcgaagggga ggaagaggaa ggcgaaggag aaggcgagga agaagaggga    900
gaggaggaag gcgaggagga aggagagggg gaggaggagg ga                      942
```

<210> SEQ ID NO 13
<211> LENGTH: 3081
<212> TYPE: DNA
<213> ORGANISM: Artificial Sequence
<220> FEATURE:
<223> OTHER INFORMATION: a preferred RPGRORF15-encoding nucleotide sequence

<400> SEQUENCE: 13

```
atgagagagc cagaggagct gatgccagac agtggagcag tgtttacatt cggaaaatct      60
aagttcgctg aaaataaccc aggaaagttc tggtttaaaa acgacgtgcc cgtccacctg     120
tcttgtggcg atgagcatag tgccgtggtc actgggaaca ataagctgta catgttcggg     180
tccaacaact ggggacagct ggggctggga tccaaatctg ctatctctaa gccaacctgc     240
gtgaaggcac tgaaacccga gaaggtcaaa ctggccgctt gtggcagaaa ccacactctg     300
gtgagcaccg agggcgggaa tgtctatgcc accggaggca caatgaggg acagctggga     360 ctgggggaca ctgaggaaag gaataccttt cacgtgatct ccttctttac atctgagcat     420
aagatcaagc agctgagcgc tggctccaac acatctgcag ccctgactga ggacgggcgc     480
ctgttcatgt ggggagataa ttcagagggc cagattgggc tgaaaaacgt gagcaatgtg     540
tgcgtccctc agcaggtgac catcggaaag ccagtcagtt ggatttcatg tggctactat     600
catagcgcct tcgtgaccac agatggcgag ctgtacgtct ttggggagcc cgaaaacgga     660
aaactgggcc tgcctaacca gctgctgggc aatacccgga cacccagct ggtgtccgag     720 atccctgaaa agtgatcca ggtcgcctgc ggggagagc atacagtggt cctgactgag     780
aatgctgtgt ataccttcgg actgggccag tttggccagc tggggctggg aaccttcctg     840
tttgagacat ccgaaccaaa agtgatcgag aacattcgcg accagactat cagctacatt     900
```

```
tcctgcggag agaatcacac cgcactgatc acagacattg gcctgatgta tacctttggc    960
gatggacgac acgggaagct gggactggga ctggagaact tcactaatca ttttatcccc   1020
accctgtgtt ctaacttcct gcggttcatc gtgaaactgg tcgcttgcgg cgggtgtcac   1080
atggtggtct tcgctgcacc tcatagggc gtggctaagg agatcgaatt tgacgagatt    1140
aacgatacat gcctgagcgt ggcaactttc ctgccataca gctccctgac ttctggcaat   1200
gtgctgcaga gaaccctgag tgcaaggatg cggagaaggg agagggaacg ctctcctgac   1260
agtttctcaa tgcgacgaac cctgccacct atcgagggaa cactgggact gagtgcctgc   1320
ttcctgccta actcagtgtt tccacgatgt agcgagcgga atctgcagga gtctgtcctg   1380
agtgagcagg atctgatgca gccagaggaa cccgactacc tgctggatga gatgaccaag   1440
gaggccgaaa tcgacaactc tagtacagtg gagtccctgg gcgagactac cgatatcctg   1500
aatatgacac acattatgtc actgaacagc aatgagaaga gtctgaaact gtcaccagtg   1560
cagaagcaga gaaacagca gactattggc gagctgactc aggacaccgc cctgacagag    1620
aacgacgata gcgatgagta tgaggaaatg tccgagatga aggaaggcaa agcttgtaag   1680
cagcatgtca gtcaggggat cttcatgaca cagccagcca caactattga ggcttttca    1740
gacgaggaag tggagatccc cgaggaaaaa gagggcgcag aagattccaa ggggaatgga   1800
attgaggaac aggaggtgga agccaacgag gaaaatgtga agtccacgg aggcaggaag    1860
gagaaaacag aaatcctgtc tgacgatctg actgacaagg ccgaggtgtc cgaaggcaag   1920
gcaaaatctg tcggagaggc agaagacgga ccagagggac gaggggatgg aacctgcgag   1980
gaaggctcaa gcggggctga gcattggcag gacgaggaac gagagaaggg cgaaaaggat   2040
aaaggccgcg gggagatgga acgacctgga gagggcgaaa aagagctggc agagaaggag   2100
gaatggaaga aaagggacgg cgaggaacag gagcagaaa aaagggagca gggccaccag    2160
aaggagcgca accaggagat ggaagagggc ggcgaggaag agcatggcga gggagaagag   2220
gaagagggcg atagaagag ggaagaggaa aagaaggcg aagggaagga ggaaggagag     2280
ggcgaggaag tggaaggcga gagggaaaag gaggaaggag aacggaagaa agaggaaaga   2340
gccggcaaag aggaaaaggg cgaggaagag ggcgatcagg gcgaaggcga ggaggaagag   2400
accgagggcc gcggggaaga gaaagaggag ggaggagagg tggagggcgg agaggtcgaa   2460
gagggaaagg gcgagcgcga agaggaagag gaagagggcg agggcgagga agaagagggc   2520
gagggggaag aagaggaggg agagggcgaa gaggaagagg ggagggaaa gggcgaagag   2580
gaaggagaag gcgaggaaga agagggagag gaggaaggcg aggaggaagg agaggggga    2640
gaggagggag aaggcgaggg cgaagaagaa gaagagggag aagtggaggg cgaagtcgag   2700
ggggaggagg gagaagggga agggggaggaa gaagagggcg aagaagaagg cgaggaaaga   2760
gaaaagagg gagaaggcga ggaaaaccgg agaaatgggg aagaggagga gaggaagag    2820
ggaaagtacc aggagacagg cgaagaggaa acgagcggc aggatggcga ggaatataag   2880
aaagtgagca agatcaaagg atccgtcaag tacggcaagc acaaaaccta tcagaagaaa   2940
agcgtgacca acacacaggg gaatggaaaa gagcagagga gtaagatgcc tgtgcagtca   3000
aaacggctgc tgaagaatgg cccatctgga agtaaaaaat tctggaacaa tgtgctgccc   3060
cactatctgg aactgaaata a                                             3081
```

<210> SEQ ID NO 14
<211> LENGTH: 378
<212> TYPE: DNA
<213> ORGANISM: Artificial Sequence

```
<220> FEATURE:
<223> OTHER INFORMATION: deletion sequence

<400> SEQUENCE: 14
ggagaggaag gggagggaga ggaagagggg gaggagggcg aggggggaagg cgaggaggaa      60 gaaggagagg gggaaggcga agaggaaggc gaggggggaag gagaggagga agaaggggaa     120
ggcgaaggcg aagaggaggg agaaggagag ggggaggaag aggaaggaga agggaagggc     180
gaggaggaag gcgaagaggg agaggggggaa ggcgaggaag aggaaggcga gggcgaagga     240
gaggacggcg agggcgaggg agaagaggag gaagggggaat gggaaggcga agaagaggaa     300
ggcgaaggcg aaggcgaaga agagggcgaa ggggagggcg aggagggcga aggcgaaggg     360
gaggaagagg aaggcgaa                                                    378
```